(12) United States Patent
Steuernagel et al.

(10) Patent No.: US 8,828,934 B2
(45) Date of Patent: *Sep. 9, 2014

(54) MNK KINASE HOMOLOGOUS PROTEINS INVOLVED IN THE REGULATION OF ENERGY HOMEOSTASIS AND ORGANELLE METABOLISM

(75) Inventors: Arnd Steuernagel, Goettingen (DE); Karsten Eulenberg, Bovenden (DE); Guenter Broenner, Goettingen (DE); Thomas Ciossek, Ravensburg (DE); Bettina Rudolph, Hannover (DE); Dorothea Rudolph, Vienna (AT); Funmi Belgore, London (GB); Stefan Jaekel, Goettingen (DE); Christoph Meyer, Goettingen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/245,188

(22) Filed: Sep. 26, 2011

(65) Prior Publication Data
US 2012/0045452 A1 Feb. 23, 2012

Related U.S. Application Data

(63) Continuation of application No. 12/174,301, filed on Jul. 16, 2008, now Pat. No. 8,076,098, which is a continuation of application No. 10/494,010, filed as application No. PCT/EP02/12075 on Oct. 29, 2002, now abandoned.

(30) Foreign Application Priority Data

| Oct. 29, 2001 | (EP) | .................................. 01125812 |
| May 17, 2002 | (EP) | .................................. 02011073 |

(51) Int. Cl.
| A61K 38/45 | (2006.01) |
| C12N 9/12 | (2006.01) |
| A61K 38/00 | (2006.01) |

(52) U.S. Cl.
CPC .............. *C12N 9/1205* (2013.01); *A61K 38/45* (2013.01)
USPC .............................. 514/6.9; 435/183; 435/194

(58) Field of Classification Search
CPC ............... C12Y 207/11024; C12Y 207/11025; C12Y 207/12002; C12Q 1/25; A61K 49/0004
See application file for complete search history.

(56) References Cited

U.S. PATENT DOCUMENTS

| 5,658,903 A | 8/1997 | Adams et al. |
| 5,786,356 A | 7/1998 | Bell et al. |
| 5,932,576 A | 8/1999 | Anantanarayan et al. |
| 5,981,533 A | 11/1999 | Traxler et al. |
| 2003/0041341 A1* | 2/2003 | Sonenberg et al. ............ 800/18 |
| 2005/0196787 A1* | 9/2005 | Bhanot et al. ..................... 435/6 |
| 2009/0163520 A1 | 6/2009 | Coulter et al. |
| 2009/0203605 A1* | 8/2009 | Segatori et al. ................. 514/12 |
| 2010/0093605 A1* | 4/2010 | Levetan et al. .................... 514/4 |
| 2010/0322906 A1* | 12/2010 | Matsuyama et al. ......... 424/93.7 |
| 2013/0065914 A1* | 3/2013 | Heckel et al. .............. 514/260.1 |

FOREIGN PATENT DOCUMENTS

| EP | 0 819 129 | 1/1998 |
| JP | 601 85719 | 9/1985 |
| WO | WO 89/11295 | 11/1989 |
| WO | WO 9506411 A | 3/1995 |
| WO | WO 98/25908 A1 | 6/1998 |
| WO | WO 99/02532 A2 | 1/1999 |
| WO | WO 02055664 | 7/2002 |
| WO | WO 02103361 | 12/2002 |
| WO | WO 02103361 A | 12/2002 |
| WO | 2006066937 | 6/2006 |

OTHER PUBLICATIONS

Tschop et al. (2000) Phosphorylation of elF-4E on Ser 209 in response to mitogenic and inflammatory stimuli is faithfully detected by specific antibodies, Mol. Cell Biol. Res. Commun., vol. 3, No. 4, pp. 205-211.*

Knauf et al. (2001) Negative Regulation of Protein Translation by Mitogen-Activated Protein Kinase-Interacting Kinases 1 and 2, Mol. Cell. Biol., vol. 21, No. 6, pp. 5500-5511.*

La Fontaine et al. (1999) Intracellular Localization and Loss of Copper Responsiveness of Mnk, the Murine Homologue of the Menkes Protein, in Cells from Blotchy (Moblo) and Brindled (Mobr) Mouse Mutants, Human Mol. Gen., vol. 8, No. 6, pp. 1069-1075.*

Scheper et al. (2001) Phosphorylation of Eukaryotic Initiation Factor 4E Markedly Reduces Its Affinity for Capped mRNA, J. Biol. Chem., vol. 277, No. 5, pp. 3303-3309.*

Scheper et al. (2003) The N and C termini of the splice variants of the human mitogen-activated protein kinase-interacting kinase Mnk2 determine activity and localization, Mol. Cell. Biol., vol. 23, No. 16, apges 5692-5705.*

(Continued)

*Primary Examiner* — Manjunath Rao
*Assistant Examiner* — Samuel Liu
(74) *Attorney, Agent, or Firm* — Thomas Horstemeyer, LLP

(57) ABSTRACT

This invention relates to the use of nucleic acid sequences of the MAP kinase-interacting kinase (Mnk) gene family and amino acid sequences encoded thereby, and to using these sequences or effectors of Mnk nucleic acids or polypeptides, particularly Mnk kinase inhibitors and activators, in the diagnosis and treatment of diseases and disorders related to bodyweight regulation and thermogenesis. One aspect of the disclosure encompasses methods of identifying an animal or human having an elevated probability of having or developing a pancreatic malfunction, the method comprising: (a) obtaining a biological sample from an animal or human subject; and (b) determining from the biological sample whether the subject has a genetic variant of an Mnk2 and/or Mnk1 gene or a homolog thereof, or an expression product of said Mnk2 and/or Mnk1 gene or homolog thereof, wherein said genetic variant is associated with an elevated probability of having or developing a pancreatic malfunction.

3 Claims, 33 Drawing Sheets

(56) References Cited

OTHER PUBLICATIONS

Cherkasov et al. (2004) Structural characterization of genomes by large scale sequence-structure threading: application of reliability analysis in structural genomics, BMC Bioinform., 5 (61), 1-11.*
Slenz-Kesler et al. (2000) Identification of the human Mnk2 gene (MKNK2) through protein interaction with estrogen receptor beta, Genomics, vol. 69, No. 1, pp. 63-71.*
Scheper et al. (Feb. 2001) The Mitogen-Activated Protein Kinase Signal-Integrating Kinase Mnk2 Is a Eukaryotic Initiation Factor 4E Kinase with High Levels of Basal Activity in Mammalian Cells, Mol. Cell Biol., vol. 21, No. 3, pp. 743-754.*
Fukunaga R et al.: Mnkl, a new map kinase-activated protein kinase, isolated by a novel expression screening method for identifying protein kinase substrates, Embo Journal, Oxford University Press, Surrey, GB, vol. 16, No. 8, 1997, pp. 1921-1933, XP000887346.
Slentz-Kesler K et al.: Identification of the human Mnk2 gene (MKNK2) through protein interaction with estrogen receptor beta, Genomics, Academic Press, San Diego, US, vol. 69, No. 1, Oct. 1, 2000, pp. 63-71, XP002221149.
Database CA Online Chemical Abstracts Service, Columbus, Ohio, US; Li Nenggan et al.: Protein and cDNA sequence of a novel human protein kinase Mnk2, retrieved from STN Database accession No. 136: 19531 8 HCA, XP002246761 & CN 1 301 870 (Nanfang Research Center, State Human Genome Project, Peop. Rep. China) Jul. 4, 2001.
Database Biosis Online Biosciences Information Service, I Philadelphia, PA, US, Apr. 2000, Tschopp et al.: Phosphorylation of elF-4E on Ser 209 in response to mitogenic and inflammatory stimuli is faithfully detected by specific antibodies, Database accession No. PREV200000389084, XP002246762 cited in the application abstract & Molecular Cellular Biology Research Communications, vol. 3, No. 4, Apr. 2000, pp. 205-21 1.
Eatabase Biosis Online Biosciences Information Service, Philadelphia, PA, US, Aug. 2001, Knaiif Ursula et al.: Negative regulation of protein translation by mitogen-activated protein kinaseinteracting kinases i and 2, Database accession No. PREV200100384691, XP002246763 cited in the application abstract & Molecular Cellular Biology, vol. 21, No. 16, Apr. 2001, pp. 5500-551 1.
Waskiewicz, A.J. et al.: Phosphorylation of the cap-binding protein eukaryotic translation initiation factor 4E by protein kinase Mnkl in vivo, Mol. Cell. Biol., 1999, vol. 19, pp. 1871-1880.
Wikipedia "Aptamer" Wikipedia "Aptamer", (2010).
Tsukiyama-Kohara et al.: Mature Medicine, Oct. 1, 2001, vol. 7, No. 10, pp. 1 128-1 132.
Scheper, Gert C et al.: The mitogen-activated protein kinase signal-integrating kinase Mnk2 is / eukaryotic initiation factor 4E kinase with high levels of basal activity in mammalian cells, Mol. Cell. Biol. Feb. 2001, vol. 21, No. 3, p. 743-754.
Jauch et al.: Crystal structures of the Mnk2 kinase domain reveal an inhibitory conformation and a zinc binding site, Structure, vol. 13. / 1559-1568, Oct. 2005.
Kordik et al.: Pyrazolecarboxamide human neuropeptide Y5 receptor ligands with in vivo antifeedant activity, Bioorganic & Medicinal Chemistry Letters 11 (2001) 2287-2290.
Tocris bioscience, (2010).
Extract of the "Lexikon der Biochemie", SpeMrum Akademischer Verlag Heidelberg, 1999.
Waskiewicz, et al. "Mitogen-activated protein kinases activate the serine/theronine kinases Mnk1 and Mnk2", The EMBO Journal vol. 16, No. 8, pp. 1909-1920, 1997.

\* cited by examiner

```
hsXP_030637      MVQKKPAELQGFHRSFKGQNP---------------------FELAFSLDQPDHGDSD
(SEQ ID NO.: 2)
hsXP_001600      MVSSQ-------------------------------------------KLEKP-----
(SEQ ID NO.: 6)
dmAAB18789       MVEPKSGTAASAAAAKASNNNNNNHPRGSGDSGIRSGSGISCSNTDNSCSQSQSDGQNEL
(SEQ ID NO.: 40) *.  :                                           . .:.

hsXP_030637      FGLQCSARPDMPASQPIDIPDAKKR----------GKKKKRGRATDSFSG-RFEDVYQLQ
hsXP_001600      --------IEMGSSEPLPIADGDRR----------RKKKRRGRATDSLPG-KFEDMYKLT
dmAAB18789       TRYSSEDVSGNESSEAPNMTEVERQAELNRHKEEMQKKRRKKRISSSLHSSTFQELYKLT
                         :*:.    :.:  .::          **:::  *  :.*:.  *:::*:* hsXP_030637      EDVLGEGAHARVQTCINLITSQEYAVKIIEKQPGHIRSRVFREVEMLYQCQGHRNVLELI
hsXP_001600      SELLGEGAYAKVQGAVSLQNGKEYAVKIIEKQAGHSRSRVFREVETLYQCQGNKNILELI
dmAAB18789       GEILGEGAYASVQTCVNIYTDLEYAVKVIDKIPGHARARVFREVETFHHCQGHLGILQLI
                 ::*****:*    ..:   .. ***:*.:* .**  *:****  :::*: ..:*:*** hsXP_030637      EFFEEEDRFYLVFEKMRGGSILSHIHKRRHFNELEASVVVQDVASALDFLHNKGIAHRDL
hsXP_001600      EFFEDDTRFYLVFEKLQGGSILAHIQKQKHFNEREASRVVRDVAAALDFLHTKGIAHRDL
dmAAB18789       EFFEDDKKFYLVFEKINGGPLLSRIQEHICFSEHEPSQIIKEIASGLDFLHKKGIAHRDL
                 *::.  :***:..:**:.*::::   *.*  *.*  ::::::*..*** .******* hsXP_030637      KPENILCEHPNQVSPVKICDFDLGSGIKLNGDCS-PISTPELLTPCGSAEYMAPEVVEAF
hsXP_001600      KPENILCESPEKVSPVKICDFDLGSGMKLNNSCT-PITTPELTTPCGSAEYMAPEVVEVF
dmAAB18789       KPENILCVKTDSLCPIKICDFDLGSGIKFTTDISSPAATPQLLTPVGSAEFMAPEVVDLF
                 ******    .:: *:.*********:*:. .   .* :*:*  :****:  * hsXP_030637      SEEASIYDKRCDLWSLGVILYILLSGYPPFVGRCGSDCGWDRGEACPACQNMLFESIQEG
hsXP_001600      TDQATFYDKRCDLWSLGVVLYIMLSGYPPFVGHCGADCGWDRGEVCRVCQNKLFESIQEG
dmAAB18789       VGEAHYYDKRCDLWSLGVIAYILLCGYPPFSGNCGEDCGWNRGENCRTCQELLFESIQEG
                 . :*   ************: **:* ****** *.** .****:*** * :** ********:

hsXP_030637      KYEFPDKDWAHISCAAKDLISKLLVRDAKQRLSAAQVLQHPWVQGCAPE---------N
hsXP_001600      KYEFPDKDWAHISSEAKDLISKLLVRDAKQRLSAAQVLQHPWVQGQAPE---------K
dmAAB18789       HFSFPEAEWHDVSDEAKDLISNLLVKKASNRLSAEAVLNHPWIRMCEQEPPASKHGRRHK
                 :.**:  *  .:*  ******:***:.*.:**** .**:***:.  . *                :

hsXP_030637      TLPTPMVLQRN-SCAKDLTSFAAEAIAMNRQLAQH-------------------------
hsXP_001600      GLPTPQVLQRN-SSTMDLTLFAAEAIALNRQLSQH-------------------------
dmAAB18789       ALQTPSNIRRNHQSAREISQFAESAMAVKRVVLQHFSMRYDYMKERPNIYQPSQAYMDAY
                 * **  ::.** ..:  :: ** .*:*::* :**

hsXP_030637      -DEDLAEEEA------AGQGQPVLVRATSRCLQLSPPSQSKLAQRRQRASLSSAPVVLVG
hsXP_001600      -EENELAEEP------EALADGLCS------MKLSPPCKSRLARRRALQAGRGEDRSPP
dmAAB18789       SDENYNPKPPGHYTRNSQRNPASSLCGYG-GRMSSMHGQRANSRRSSRNASRNASAIYP
                 :*:   :  .                :       ::*.      .:     **      . .

hsXP_030637      DHA---------------------------------------------------------
hsXP_001600      TAL---------------------------------------------------------
dmAAB18789       NSGGFKTLNVHEEDDDDEGLEAFGHIDDDDEWSRSRREYQQQCETLGEDRFRRQSGSEGD
```

*Fig. 3A*

```
hsXP_030637   ------------------------------------------------------------
hsXP_001600   ------------------------------------------------------------
dmAAB18789    EVEDDEDGENEDYQHYKHYWRELDEEEGDDYLYEQQQKVDDKPGEEEFEDEPKEETQADN hsXP_030637   ------------------------------------------------------------
hsXP_001600   ------------------------------------------------------------
dmAAB18789    LKLSKAYVEQVGETNVEKSKPQDDNQGYIREDLIMDNMDMKKNTQQSEFAKLJTIMRNDAQ hsXP_030637   ------------------------------------------------------------
hsXP_001600   ------------------------------------------------------------
dmAAB18789    TEENKIMQQQDEEKKEDKQQDDVKGAKKQGPSSDISATTITDNNKLQTPVMTTTRINRWQ hsXP_030637   ------------------------------------------------------------
hsXP_001600   ------------------------------------------------------------
dmAAB18789    TGDAIEDDDVKLLDSISDLNEKLPEIYETANIVVNSAAVPAASTPAASATRPPTDNPEED hsXP_030637   ------------------------------------------------------------
hsXP_001600   ------------------------------------------------------------
dmAAB18789    DSNVTEPTTTAEGTTNQTTPKNSAREEKPVALSHTAGHHSKTGRTVNFAPDAYQNDEDAD hsXP_030637   ------------------------------------------------------------
hsXP_001600   ------------------------------------------------------------
dmAAB18789    IDEDDDYDDEENLHEHSKQQLPSNAYTRKQRQQHQRVIVPEYQLADQVPQRQHTENWRYR hsXP_030637   ------------------------------------------------------------
hsXP_001600   ------------------------------------------------------------
dmAAB18789    THHSQEQQPTADYRKYRPPFSTGGGGHHGNLQRHYLGSFSHSGGAAGYEIAPMPPPMQP hsXP_030637   ------------------------------------------------------------
hsXP_001600   ------------------------------------------------------------
dmAAB18789    PPRHNSAGSGSGSGSGGSPPGDEQSAIRNWRQDCVYARSCOHNQCFSQQRHHRSEQQRV hsXP_030637   ------------------------------------------------------------
hsXP_001600   ------------------------------------------------------------
dmAAB18789    QQQPRIGSGRPAHLQAAQLMDELPDMRIGLSPPSESVLLQRRLRQQQRANDLSEVLRAGH hsXP_030637   -------------
hsXP_001600   -------------
dmAAB18789    RQWLRGSTVDK
```

SEQ ID NO.: 1

```
   1 cggtcccctc ccccgctggc ggggcccgga cagaagatgg tgcagaagaa accagccgaa
  61 cttcagggtt tccaccgttc gttcaagggg cagaacccct tcgagctggc cttctcccta
 121 gaccagcccg accacggaga ctctgacttt ggcctgcagt gctcagcccg ccctgacatg
 181 ccgccagcc agcccattga catcccggac gccaagaaga ggggcaagaa gaagaagcgc
 241 ggccgggcca ccgacagctt ctcgggcagg tttgaagacg tctaccagct gcaggaagat
 301 gtgctggggg agggcgctca tgcccgagtg cagacctgca tcaacctgat caccagccag
 361 gagtacgccg tcaagatcat tgagaagcag ccaggccaca ttcggagcag ggttttcagg
 421 gaggtggaga tgctgtacca gtgccaggga cacaggaacg tcctagagct gattgagttc
 481 ttcgaggagg aggaccgctt ctacctggtg tttgagaaga tgcggggagg ctccatcctg
 541 agccacatcc acaagcgccg gcacttcaac gagctggagg ccagcgtggt ggtgcaggac
 601 gtggccagcg ccttggactt tctgcataac aaaggcatcg cccacaggga cctaaagccg
 661 gaaaacatcc tctgtgagca ccccaaccag gtctcccccg tgaagatctg tgacttcgac
 721 ctgggcagcg gcatcaaact caacggggac tgctccccta tctccacccc ggagctgctc
 781 actccgtgcg gctcggcgga gtacatggcc ccggaggtag tggaggcctt cagcgaggag
 841 gctagcatct acgacaagcg ctgcgacctg tggagcctgg gcgtcatctt gtatatccta
 901 ctcagcggct acccgccctt cgtgggccgc tgtggcagcg actgcggctg ggaccgcggc
 961 gaggcctgcc ctgcctgcca gaacatgctg tttgagagca tccaggaggg caagtacgag
1021 ttccccgaca aggactgggc ccacatctcc tgcgctgcca agacctcat ctccaagctg
1081 ctggtccgtg acgccaagca gaggctgagt gccgcccaag tcctgcagca ccctgggtt
1141 caggggtgcg ccccgagaa caccttgccc actcccatgg tcctgcagag aacagctgt
1201 gccaaagacc tcacgtcctt cgcggctgag gccattgcca tgaaccggca gctggcccag
1261 cacgacgagg acctggctga ggaggaggcc gcggggcagg gccagcccgt cctggtccga
1321 gctacctcac gctgcctgca gctgtctcca ccctcccagt ccaagctggc gcagcggcgg
1381 caagggcca gtctgtcctc ggccccagtg gtcctggtgg agaccacgc ctgaccctcc
1441 catc
```

*Fig. 3D*

SEQ ID NO.: 2

MVQKKPAELQGFHRSFKGQNPFELAFSLDQPDHGDSDFGLQCSA

RPDMPASQPIDIPDAKKRGKKKKRGRATDSFSGRFEDVYQLQEDVLGEGAHARVQTCI

NLITSQEYAVKIIEKQPGHIRSRVFREVEMLYQCQGHRNVLELIEFFEEEDRFYLVFE

KMRGGSILSHIHKRRHFNELEASVVVQDVASALDFLHNKGIAHRDLKPENILCEHPNQ

VSPVKICDFDLGSGIKLNGDCSPISTPELLTPCGSAEYMAPEVVEAFSEEASIYDKRC

DLWSLGVILYILLSGYPPFVGRCGSDCGWDRGEACPACQNMLFESIQEGKYEFPDKDW

AHISCAAKDLISKLLVRDAKQRLSAAQVLQHPWVQGCAPENTLPTPMVLQRNSCAKDL

TSFAAEAIAMNRQLAQHDEDLAEEEAAGQGQPVLVRATSRCLQLSPPSQSKLAQRRQR
ASLSSAPVVLVGDHA

*Fig. 3E*

SEQ ID NO.: 3

```
gctggcgggg cccggacaga agatggtgca gaagaaacca gccgaacttc agggtttcca
   61 ccgttcgttc aagggggcaga acccctcga gctggccttc tccctagacc agcccgacca
  121 cggagactct gactttggcc tgcagtgctc agcccgccct gacatgcccg ccagccagcc
  181 cattgacatc ccggacgcca agaagagggg caagaagaag aagcgcggcc gggccaccga
  241 cagcttctcg ggcaggtttg aagacgtcta ccagctgcag gaagatgtgc tgggggaggg
  301 cgctcatgcc cgagtgcaga cctgcatcaa cctgatcacc agccaggagt acgccgtcaa
  361 gatcattgag aagcagccag gccacattcg gagcagggtt tcagggagg tggagatgct
  421 gtaccagtgc cagggacaca ggaacgtcct agagctgatt gagttcttcg aggaggagga
  481 ccgcttctac ctggtgtttg agaagatgcg gggaggctcc atcctgagcc acatccacaa
  541 gcgccggcac ttcaacgagc tggaggccag cgtggtggtg caggacgtgg ccagcgcctt
  601 ggactttctg cataacaaag gcatcgccca cagggaccta aagccggaaa acatcctctg
  661 tgagcaccc aaccaggtct cccccgtgaa gatctgtgac ttcgacctgg gcagcggcat
  721 caaactcaac ggggactgct ccctatctc cacccggag ctgctcactc cgtgcggctc
  781 ggcggagtac atggcccgg agttagtgga ggccttcagc gaggaggcta gcatctacga
  841 caagcgctgc gacctgtgga gcctgggcgt catcttgtat atcctactca gcggctaccc
  901 gcccttcgtg ggccgctgtg gcagcgactg cggctgggac cgcggcgagg cctgccctgc
  961 ctgccagaac atgctgtttg agagcatcca ggagggcaag tacgagttcc ccgacaagga
 1021 ctgggcccac atctcctgcg ctgccaaaga cctcatctcc aagctgctgg tccgtgacgc
 1081 caagcagagg ctgagtgccg cccaagtcct gcaacacccc tgggttcagg ggtgcgcccc
 1141 ggagaacacc ttcccactc ccatggtcct gcagaggtgg gacagtcact cctcctccc
 1201 tccccacccc tgtcgcatcc acgtgcgacc tggaggactg gtcagaaccg ttactgtgaa
 1261 tgagtgaaga tcctggagga ccctggcccc aggccagctc ccatcgctgg gggacggtga
 1321 acggccatgt gttaatgtta cgatgttttt aaaagacaaa aaaaaaaaaa aaacctcaaa
 1381 agttttttta aagtggggga aaaacatcca agcactttaa ttccaatgta ccaggtgaac
 1441 tgacggagct cagaagtttt cctttacacc aactgtcaat gccggaattt tgtattctgt
 1501 tttgtaaaga tttaataaaa gtcaaaaac ttgcaaaaaa aaaaaaaaa
```

*Fig. 3F*

SEQ ID NO.: 4

MVQKKPAELQGFHRSFKGQNPFELAFSLDQPDHGDSDFGLQCSA

RPDMPASQPIDIPDAKKRGKKKKRGRATDSFSGRFEDVYQLQEDVLGEGAHARVQTCI

NLITSQEYAVKIIEKQPGHIRSRVFREVEMLYQCQGHRNVLELIEFFEEEDRFYLVFE

KMRGGSILSHIHKRRHFNELEASVVVQDVASALDFLHNKGIAHRDLKPENILCEHPNQ

VSPVKICDFDLGSGIKLNGDCSPISTPELLTPCGSAEYMAPEVVEAFSEEASIYDKRC

DLWSLGVILYILLSGYPPFVGRCGSDCGWDRGEACPACQNMLFESIQEGKYEFPDKDW

AHISCAAKDLISKLLVRDAKQRLSAAQVLQHPWVQGCAPENTLPTPMVLQRWDSHFLL
                    PPHPCRIHVRPGGLVRTVTVNE

*Fig. 3G*

SEQ ID NO.: 5
```
   1 ggcacgaggg cgaccgctcc ccggcgggag ccagcgaagg tttccatgtc agaggccgat
  61 ggagaactga agattgccac ctacgcacaa aggccattga gacacttcgt gtagctggaa
 121 gacaccaact tcctgacagg agctttattt catttgggat ttcaagttta cagatggtat
 181 cttctcaaaa gttggaaaaa cctatagaga tgggcagtag cgaaccccct cccatcgcag
 241 atggtgacag gaggaggaag aagaagcgga ggggccgggc cactgactcc ttgccaggaa
 301 agtttgaaga tatgtacaag ctgacctctg aattgcttgg agagggagcc tatgccaaag
 361 ttcaaggtgc cgtgagccta cagaatggca aagagtatgc cgtcaaaatc atcgagaaac
 421 aagcagggca cagtcggagt agggtgtttc gagaggtgga gacgctgtat cagtgtcagg
 481 gaaacaagaa catttggag ctgattgagt tctttgaaga tgacacaagg ttttacttgg
 541 tctttgagaa attgcaagga ggttccatct tagcccacat ccagaagcaa aagcacttca
 601 atgagcgaga agccagccga gtggtgcggg acgttgctgc tgcccttgac ttcctgcata
 661 ccaaagacaa agtctctctc tgtcacctag gctggagtgc tatggcgcca tcagggctca
 721 ctgcagcccc aacctccctg ggctccagtg atcctcccac ctcagcctcc caagtagctg
 781 ggactacagg cattgctcat cgtgatctga aaccagaaaa tatattgtgt gaatctccag
 841 aaaaggtgtc tccagtgaaa atctgtgact ttgacttggg cagtgggatg aaactgaaca
 901 actcctgtac ccccataacc acaccagagc tgaccacccc atgtggctct gcagaataca
 961 tggccctga ggtagtggag gtcttcacgg accaggccac attctacgac aagcgctgtg
1021 acctgtggag cctgggcgtg gtcctctaca tcatgctgag tggctaccca ccttcgtgg
1081 gtcactgcgg ggccgactgt ggctgggacc ggggcgaggt ctgcagggtg tgcagaaca
1141 agctgtttga aagcatccag gaaggcaagt atgagtttcc tgacaaggac tgggcacaca
1201 tctccagtga agccaaagac ctcatctcca agctcctggt gcgagatgca aagcagagac
1261 ttagcgccgc ccaagttctg cagcaccca gggtgcaggg gcaagctcca gaaaagggac
1321 tccccacgcc gcaagtcctc cagaggaaca gcagcacaat ggacctgacg ctcttcgcag
1381 ctgaggccat cgcccttaac cgccagctat ctcagcacga agagaacgaa ctagcagagg
1441 agccagaggc actagctgat ggcctctgct ccatgaagct ttccctccc tgcaagtcac
1501 gcctggcccg gagacgggcc ctggcccagg caggccgtgg tgaagacagg agcccgccca
1561 cagcactctg aaatgctcca gtcacacctt ataggcccta ggcctggcca ggcattgtcc
1621 cctggaaacc tgtgtggcta aagtctgctg agcaggcagc agcctctgct ctgtggctcc
1681 attcaggctt tttcatctac gaaggccctg aggttcccat caaccccat ttccctaggg
1741 tcctggagga aaaagctttt tccaaagggg ttgtctttga aaggaaagc aatcacttct
1801 cactttgcat aattgcctgc agcaggaaca tctcttcact gggctccacc tgctcacccg
1861 cctgcagatc tgggatccag cctgctctca ccgctgtagc tgtggcggct ggggctgcag
1921 cctgcaggga gaagcaagaa gcatcagttg acagaggctg ccgacacgtg cctcttccct
1981 ctcttctctg tcaccctcct ctggcggtcc ttccaccttc ctctgtcctc cggatgtcct
2041 ctttgcccgt cttctcccct ggctgagcaa agccatcccc tcaattcagg gaagggcaag
2101 gagccttcct cattcaggaa atcaaatcag tcttccggtc tgcagcacgg aaaagcacat
2161 aatctttctt tgctgtgact gaaatgtatc cctcgtttat catccccttt gtttgtgatt
2221 gctgctaaag tcagtagtat cgttttttta aaaaaaagt ttggtgtttt taaccatgct
2281 gttccagcaa agatgatacc ttaaactccc actgcaagcc catgaacttc ccagagagtg
2341 gaacggcttg ctcttctttc tagaatgtcc atgcacttgg gttttaatca gcagttccct
2401 attattctga ttttaagctg ttcctgtgat gaacttagag acagcatcgg tgtctgctgc
2461 tgtgtcccca ggtcttgtgt gggtggcaca gatctgggca gttagatagt gctctgtgcc
2521 taaggtgaag ccacactagg gtgaagcctc acttccctgt ttgagcaatg cagtgcctgc
2581 tgcccgtgtg catgaaggta cagccattca gataagtgga actattgagt tacataaaga
2641 aaatagattt gcatttgtca ggcagacgtt tatacaacac cacggtgctt ttatacattg
2701 tgcttatttt aataaaactg aaattctaaa aaaaaaaaa aaaaa
```

*Fig. 3H*

SEQ ID NO.: 6

MVSSQKLEKPIEMGSSEPLPIADGDRRRKKKRRGRATDSLPGKF

EDMYKLTSELLGEGAYAKVQGAVSLQNGKEYAVKIIEKQAGHSRSRVFREVETLYQCQ

GNKNILELIEFFEDDTRFYLVFEKLQGGSILAHIQKQKHFNEREASRVVRDVAAALDF

LHTKDKVSLCHLGWSAMAPSGLTAAPTSLGSSDPPTSASQVAGTTGIAHRDLKPENIL

CESPEKVSPVKICDFDLGSGMKLNNSCTPITTPELTTPCGSAEYMAPEVVEVFTDQAT

FYDKRCDLWSLGVVLYIMLSGYPPFVGHCGADCGWDRGEVCRVCQNKLFESIQEGKYE

FPDKDWAHISSEAKDLISKLLVRDAKQRLSAAQVLQHPWVQGQAPEKGLPTPQVLQRN

SSTMDLTLFAAEAIALNRQLSQHEENELAEEPEALADGLCSMKLSPPCKSRLARRRAL
AQAGRGEDRSPPTAL

*Fig. 3I*

SEQ ID NO.: 7

CGAGNAAGTGTTACTATCTAAACACATTTCAAACAATTCTTAACAAACAATTCCAAACATACAATTCCACTTACCACTTA
CCGACCAAATTACGAGTTTACAATGGACAAAGCTGAACGCGACTACTGGCATCTTCGATCCTTGGAAATCGAAGAGGAGC
CGCGATTTCCGCCAACAAACGTCGCTGATCCACTAACCGCACGCAATCTGTTCCAGCTCTACGTCAACACCTTCATTGGA
GCCAATCTGGCCGAGTCGTGTGTTTTCCCATTGGACGTGGCCAAGACCCGGATGCAGGTAGATGGCGAGCAGGCCAAGAA
GACGGGTAAAGCGATGCCAACTTTCCGTGCAACTCTTACCAACATGATCCGAGTGGAGGGATTCAAGTCGCTCTACGCCG
GCTTCTCGGCAATGGTGACCCGAAACTTTATCTTCAACTCGTTACGTGTTGTTCTCTACGACGTTTTCCGGCgCCCTTTT
CTCTACCAgAACGAACGGAACGAGGAAGTGCTCAAGATCTACATGGCGCTGGGATGCAGCTTCACCGCAGGCTGCATTGC
CCaGGCACTGgCCAATCCcTTTGACATcGTCAAGGTGCgAATGCAGacGGAAGgaCgCCgCCGCCAGcTGGgcTATGATG
TGCGGGTgAACAGCATGGTGCAGGCcTTcGTGgACATCTACCGCcGTGGCGGAcTGCCCAGTATGTGgAAGGGTGTAGGg
CCCAGCTGCATGCGTGCCTGCCTgATGACGACCGGCGATGTGGgCAGTTACgATATCAGTAAGCGCACCTTCAAGCGCcT
GcTGGACTTGGAGGAAGGCCTGCCACTGcGTTTcGTGTcTTCCATGtGCGCCGGACTAACGGCATCCGTGCTCAGCACGC
CGGCGaACGTGaTCAAGTCGCGGATGATGAaCCAGCCGGTGaACGAGAGCGGCAAGAATCTGTACTACAAGAACTCCCTC
GacTGCATTAGGAAGCTGGTCAGGGAGGAGGGTGTCCTCACGTTGTATAAGGGCCTCATGCCCAcTTGGTTTCGCCTGGG
ACCGTTCTCAGTGCTCTTTTGGCTGTCCGTCGAGCAGCTGCGTCAGTGGaAAGGCCAGAGTGGATTTTAGGAGCAAACTA
TCAATCTTACTATCGTATTTTGTATGTCTTTTAACACGCAATAAAAAGGGTGCAAGTCAAACCATCTATTATACATATTA
TAAATATAaCTTTAATCCCAAAAAAAAAAAAAAAAAACTCGTGCCGAATTCGAT

Fig. 7A

SEQ ID NO.: 8

MDKAERDYWHLRSLEIEEEPRFPPTNVADPLTARNLFQLYVNTFIGANLAESCVFPLDVAKTRMQVDGEQAKKTGKAMPT
FRATLTNMIRVEGFKSLYAGFSAMVTRNFIFNSLRVVLYDVFRRPFLYQNERNEEVLKIYMALGCSFTAGCIAQALANPF
DIVKVRMQTEGRRRQLGYDVRVNSMVQAFVDIYRRGGLPSMWKGVGPSCMRACLMTTGDVGSYDISKRTFKRLLDLEEGL
PLRFVSSMCAGLTASVLSTPANVIKSRMMNQPVNESGKNLYYKNSLDCIRKLVREEGVLTLYKGLMPTWFRLGPFSVLFW
LSVEQLRQWKGQSGF

Fig. 7B

| Exon | Exon position in cDNA (bp) | Intron length (bp) | 5' Intron-Exon Junction | 3' Exon-Intron Junction |
|---|---|---|---|---|
| 1 | 1-48 | 92 | SEQ ID No.:60<br>ccttagacctcgGCCCAGCACAGG | SEQ ID No.: 61<br>GAAGCCCGACCTgtgagcccca |
| 2 | 49-151 | 80 | SEQ ID No.:62<br>ctcttctctacaGACATGCCTTCC | SEQ ID No.: 63<br>GCAGGTTCGAAGgtgagctgcaga |
| 3 | 152-249 | >1kb, max. 1.3 | SEQ ID No.:64<br>ctcgcattccagATGTCTATCAGC | SEQ ID No.: 65<br>TATGCTGTCAAGagctgggtctg |
| 4 | 250-330 | 191 | SEQ ID No.:66<br>cctacattgtagATCATTGAGAAG | SEQ ID No.: 67<br>CAGGGACATAGGtaagtggcctg |
| 5 | 331-402 | 226 | SEQ ID No.:68<br>tcccaactcaggAATGTTCTAGAA | SEQ ID No.: 69<br>GAAGATGCGTGGCggtaggtaggtactgg |
| 6 | 403-509 | 87 | SEQ ID No.:70<br>ctggcctgcacaGGATCCATCCTA | SEQ ID No.: 71<br>GCATAACAAAGGtgtggcagggac |
| 7 | 510-566 | 114 | SEQ ID No.:72<br>cacctcactaggCATCGCCCACAG | SEQ ID No.: 73<br>CCCCAACCAGGTgaggctgcctga |
| 8 | 567-659 | 229 | SEQ ID No.:74<br>ccattcccaggtCTCGCCAGTGAA | SEQ ID No.: 75<br>GCTGCTCACCCCggtgagggcagt |
| 9 | 660-1020 | 309 | SEQ ID No.:76<br>ccctgccccacaGTGTGGGTCAGC | SEQ ID No.: 77<br>TGGGTGCAGGGGgtaagccttggg |
| 10 | 1021-1062 | 280 | SEQ ID No.:78<br>gacttcttacagTGTGCCCCAGAG | SEQ ID No.: 79<br>TTGGTTCTGCAGaggtgaggcctg |
| 11 | 1063-3073 | 127 | SEQ ID No.:80<br>catcctatcccAGGAACAGCTGT | SEQ ID No.: 81<br>GTCATTTAAAAAtttctgtgcagt |
| 12 | | | SEQ ID No.:82<br>aaacacaagcctAAAAAAAAAacaagcatgggg | |

MNK KINASE HOMOLOGOUS PROTEINS INVOLVED IN THE REGULATION OF ENERGY HOMEOSTASIS AND ORGANELLE METABOLISM

This application is a continuation of U.S. Ser. No. 12/174,301 filed Jul. 16, 2008, now U.S. Pat. No. 8,076,098 which is a continuation of U.S. Ser. No. 10/494,010 filed Aug. 12, 2004 now abandoned which is a 371 of International Application PCT/EP2002/12075 filed Oct. 29, 2002, which claims the benefit of European Patent Applications No. 01125812.6 filed on Oct. 29, 2001 and EP02011 073.0 filed on May 17, 2002, the disclosure of which is incorporated herein in its entirety by reference.

DESCRIPTION

This invention relates to the use of nucleic acid sequences of the Mitogen Activating Protein (MAP) kinase-interacting kinase (Mnk) gene family and amino acid sequences encoded thereby, and to the use of these sequences or effectors of Mnk nucleic acids or polypeptides, particularly Mnk kinase inhibitors and activators, in the diagnosis, study, prevention, and treatment of diseases and disorders related to body-weight regulation and thermogenesis, for example, but not limited to, metabolic diseases such as obesity, as well as related disorders such as eating disorder, cachexia, diabetes mellitus, hypertension, coronary heart disease, hypercholesterolemia, dyslipidemia, osteoarthritis, gallstones, and sleep apnea, and disorders related to ROS defence, such as diabetes mellitus, neurodegenerative disorders, and cancer, e.g. cancers of the reproductive organs.

There are several metabolic diseases of human and animal metabolism, e.g., obesity and severe weight loss that relate to energy imbalance where caloric intake versus energy expenditure is imbalanced. Obesity is one of the most prevalent metabolic disorders in the world. It is a still poorly understood human disease that becomes more and more relevant for western society. Obesity is defined as a body weight more than 20% in excess of the ideal body weight, frequently resulting in a significant impairment of health. It is associated with an increased risk for cardiovascular disease, hypertension, diabetes, hyperlipidemia and an increased mortality rate. Besides severe risks of illness, individuals suffering from obesity are often isolated socially.

Obesity is influenced by genetic, metabolic, biochemical, psychological, and behavioral factors. As such, it is a complex disorder that must be addressed on several fronts to achieve lasting positive clinical outcome. Since obesity is not to be considered as a single disorder but as a heterogeneous group of conditions with (potential) multiple causes, it is also characterized by elevated fasting plasma insulin and an exaggerated insulin response to oral glucose intake (Koltermann, J. Clin. Invest 65, 1980, 1272-1284). A clear involvement of obesity in type 2 diabetes mellitus can be confirmed (Kopelman, Nature 404, 2000, 635-643).

The molecular factors regulating food intake and body weight balance are incompletely understood. Even if several candidate genes have been described which are supposed to influence the homeostatic system(s) that regulate body mass/weight, like leptin, VCPI, VCPL or the peroxisome proliferator-activated receptor-gamma co-activator, the distinct molecular mechanisms and/or molecules influencing obesity or body weight/body mass regulations are not known. In addition, several single-gene mutations resulting in obesity have been described in mice, implicating genetic factors in the etiology of obesity (Friedman and Leibel, 1990, Cell 69: 217-220). In the obese mouse, a single gene mutation (obese) results in profound obesity, which is accompanied by diabetes (Friedman et al., 1991, Genomics 11: 1054-1062).

Therefore, the technical problem underlying the present invention was to provide for means and methods for modulating (pathological) metabolic conditions influencing thermogenesis, body-weight regulation and/or energy homeostatic circuits. The solution to said technical problem is achieved by providing the embodiments characterized in the claims.

BRIEF DESCRIPTION OF THE DRAWINGS

FIGS. 3A and 3B show the comparison of Mnk proteins.

FIG. 3A shows the comparison (CLUSTAL×1.8) multiple-sequence alignment of Mnk proteins from *Drosophila* and human Mnk proteins: hXP 030637 (SEQ ID NO.: 2) refers to human Mnk2 (identical to the protein encoded by Genbank Accession No. AF237775 (SEQ ID NO.: 1); hXP__001600 (SEQ ID NO.: 6) refers to human Mnk1 (identical to the protein encoded by the nucleic acid sequence having the Genbank Accession No. AB000409.1 (SEQ ID NO.: 56); dmAB18789 refers to the protein having the amino acid sequence SEQ ID NO.: 40 and encoded by *Drosophila* Lk6 gene with GadFly Accession No. CG17342. Gaps in the alignment are represented as -.

FIG. 3B shows the comparison (CLUSTAL W 1.82) of human Mnk2 proteins. Amino acid sequence having Genbank Accession Number XM 030637.3 is identical to the amino acid sequence having Genbank Accession Number AF237775 (SEQ ID NO.: 2). The amino acid sequence labeled NM__017572.1 (SEQ ID NO.: 4) shows a different variant of the human Mnk2 protein.

FIG. 3C shows the comparison (CLUSTAL W 1.82) of human Mnk1 proteins. Amino acid sequence having Genbank Accession Number XM 001600.2 is identical to Genbank Accession Number AB000409.1 (SEQ ID NO.: 56), and Genbank Accession Number NM__003684.2 (SEQ ID NO.: 59) shows a different variant of the Mnk1 protein.

FIG. 3D. Nucleic acid sequence of human MAP kinase-interacting kinase (Mnk) 2a (SEQ ID NO.: 1) having GenBank Accession Number AF237775 (alternatively designated as GenBank Accession Number XM__030637).

FIG. 3E. Amino acid sequence of human MAP kinase-interacting kinase (Mnk) 2a (SEQ ID NO.: 2) encoded by the nucleic acid sequence SEQ ID NO.: 1 (alternatively designated as GenBank Accession Number XM__030637).

FIG. 3F. Nucleic acid sequence of human MAP kinase-interacting kinase (Mnk) 2b (SEQ ID NO.: 3) contained within the nucleic acid sequence having GenBank Accession Number AF237776 (SEQ ID NO.: 54) which is a variant of the nucleic acid sequence labeled NM_17572.2 (SEQ ID NO.: 55).

FIG. 3G. Amino acid sequence of human MAP kinase-interacting kinase (Mnk) 2b (SEQ ID NO.: 4) encoded by the nucleic acid sequence SEQ ID NO.: 3, or nucleic acid sequences having the GenBank Accession Numbers AF237776 (SEQ ID NO.: 54), which is a variant of the nucleic acid sequence having the GenBank Accession Number NM_017572.2 (SEQ ID NO.: 55).

FIG. 3H. Nucleic acid sequence of human MAP kinase-interacting kinase (Mnk) 1 (SEQ ID NO.: 5); GenBank Accession Number AB000409 (SEQ ID NO: 56), alternatively designated as GenBank Accession Number NM 003684 (SEQ ID NO.: 87) or XM_001600).

FIG. 3I. Amino acid sequence of human MAP kinase-interacting kinase (Mnk) 1 (SEQ ID NO.: 6) encoded by the nucleic acid sequence having GenBank Accession Number AB000409 (SEQ ID NO: 56), alternatively designated as GenBank Accession Number NM 003684 (SEQ ID NO.: 87) or XM_001600).

FIG. 5A shows the real-time PCR analysis of Mnk2 in wild-type mouse tissues

FIG. 5B shows the expression of mouse Mnk2 gene in fasted and obese (ob/ob) mice models.

FIG. 6A shows the real-time PCR analysis of Mnk1 in wildtype mouse tissues

FIG. 6B shows the real-time PCR mediated comparison of Mnk1 expression in different mouse models.

FIGS. 7A and 7B show the UCPy sequences SEQ ID NOs.: 7 and 8.

FIG. 7A shows the nucleic acid sequence (SEQ ID NO.: 7) of a full-length cDNA encoding the *Drosophila* UCPy protein (SEQ ID NO.: 8). The open reading frame is underlined.

FIG. 7B shows the amino acid sequence *Drosophila* UCPy protein (SEQ ID NO.: 8) encoded by the underlined sequence shown in FIG. 7A.

FIG. 8A shows reduction in cellular triglyceride levels (μg/mg protein) in cells over-expressing Mnk2 compared to control cells. All samples were analyzed in duplicates (s1; sample 1, s2; sample 2). The Y-axis shows cellular triglyceride levels (μg/mg protein) and the X-axis shows days of cell differentiation.

FIGS. 9A and 9B show the expression of human Mnk2 in different human tissues.

FIG. 9A shows the expression of human Mnk2A and Mnk2B in different human tissues.

FIG. 9B shows the expression of human Mnk2A and human Mnk2B during adipocyte differentiation.

FIG. 12 shows the nucleic acid regions (SEQ ID NOs.: 60-82) encompassing the exon/intron boundaries of the mouse Mnk2 gene. Exon/intron boundaries of the mouse Mnk2 gene are illustrated in this figure. Exon numbers, the position of the exons of the cDNA having GenBank accession number BC010256 (SEQ ID NO.: 57) and intron lengths are indicated. Intron sequences are shown in lowercase letters, exon sequences are shown in capital, bold letters.

Figure 1:
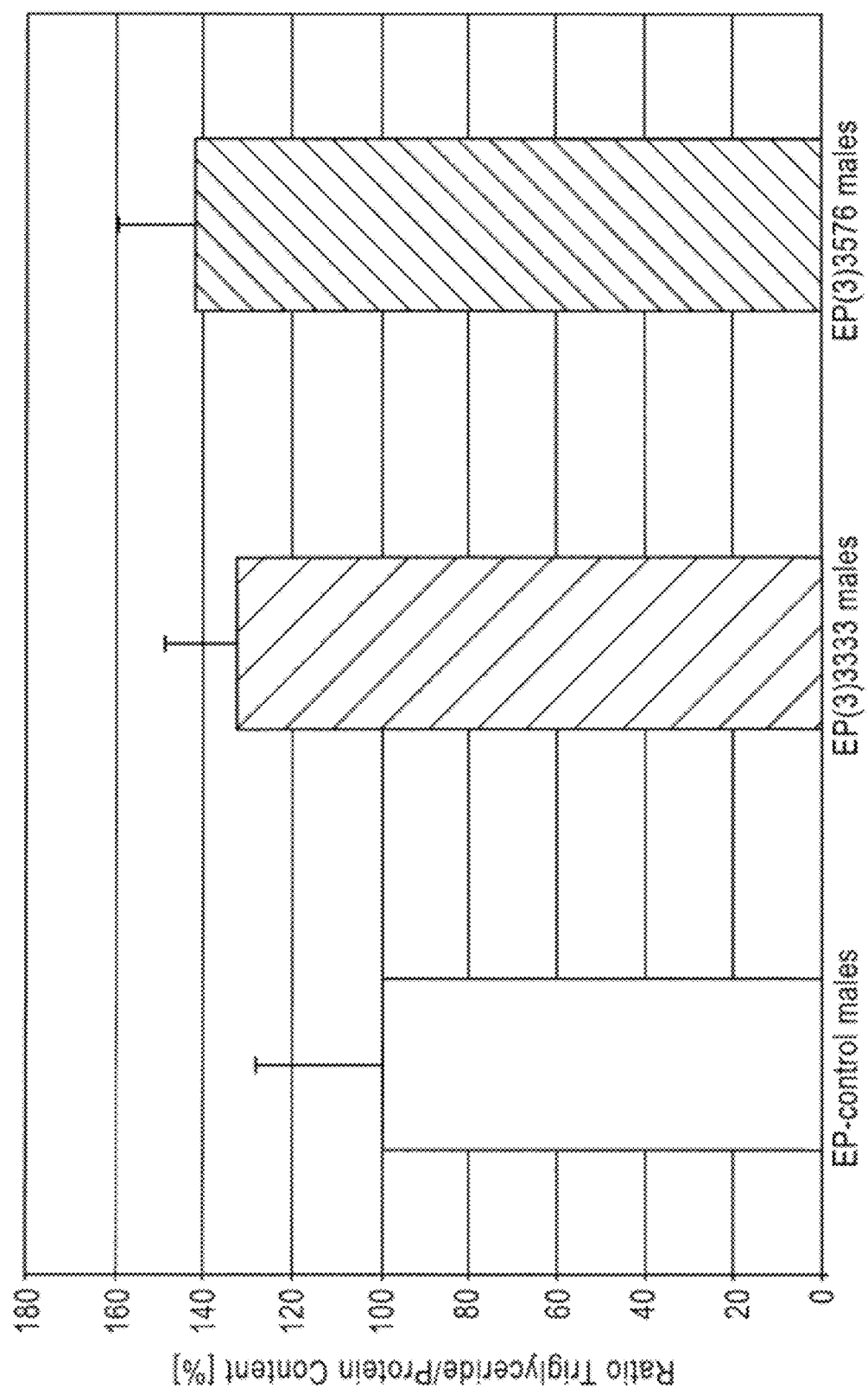
FIG. 1 shows the increase of triglyceride content of EP(3) 3333 and EP(3)3576 male flies caused by homozygous viable integration of the P-vector (in comparison to EP-control males). Shown is the ratio of the triglyceride to protein content of the mutants in percent (%)).

Accordingly, the present invention relates to genes with novel functions in body-weight regulation, energy homeostasis, metabolism, and obesity. The present invention provides for a specific gene involved in the regulation of diseases and disorders related to body-weight regulation and thermogenesis, for example, but not limited to, metabolic diseases such as obesity, as well as related disorders such as eating disorder, cachexia, diabetes mellitus, hypertension, coronary heart disease, hypercholesterolemia, dyslipidemia, osteoarthritis, gallstones, cancers of the reproductive organs, and sleep apnea, and disorders related to ROS defence, such as diabetes mellitus, neurodegenerative disorders, and cancer. The present invention describes the human Mnk genes as being involved in those conditions mentioned above, in particular the human Mnk2 gene variants.

The term "GenBank Accession number" relates to National Center for Biotechnology Information (NCBI) GenBank database entries (Benson et al, Nucleic Acids Res. 28, 2000, 15-18).

Protein kinases are important molecules involved in the regulation of many cellular functions. The *Drosophila melanogaster* LK6 serine/threonine kinase gene has been described as a short-lived kinase that can associate with microtubules (J. Cell Sci. 1997 110(2):209-219). Genetic analysis in the development of the *Drosophila* compound eye suggested a role in the modulation of the RAS signaling pathway (Genetics 2000 156(3):1219-1230). As described in this invention, the closest human homologues of *Drosophila* LK6 kinase are the MAP kinase-interacting kinase 2 (Mnk2, for example the variants Mnk2a and Mnk2b) and MAP kinase-interacting kinase 1 (Mnk1). All three proteins are predominantly localized in the cytoplasm. Mnks are phosphorylated by the pk42 MAP kinases Erk1 and Erk2 and the p38 MAP kinases. This phosphorylation is triggered in response to growth factors, phorbol esters and oncogenes like Ras and Mos as well as by stress signaling molecules and cytokines. The phosphorylation of Mnk proteins stimulates its kinase activity towards eukaryotic initiation factor 4E (EMBO J. 16: 1909-1920 (1997), Mol Cell Biol 19:1871-1880 (1999), Mol Cell Biol 21: 743-754 (2001)). Phosphorylation of eukaryotic initiation factor 4E (eIF4E) results in a regulation of protein translation (Mol Cell Biol 22: 5500-5511 (2001)).

There are different hypothesis describing the mode of stimulation of the protein translation by Mnk proteins. Most publications described a positive stimulatory effect on the cap-dependent protein translation upon activation of MAP kinase-interacting kinases. Thus, activation of Mnk proteins might lead to an indirect stimulation or regulation of protein translation, for example by the action on cytosolic phospholipase 2 alpha (BBA 1488:124-138, 2000).

Inhibitors of Mnk (referred to as CGP57380 and CGP052088) were described in the prior art (see, Knauf et al., 2001, Mol. Cell. Biol. 21:5500, Tschopp et al., 2000, Mol Cell Biol Res Comm 3:205 and Slentz-Kesler et al., 2000, Genomics 69:63). CGP052088 is a staurosporine derivative with an IC50 of 70 nM for inhibition of in vitro kinase activity of Mnk1. CGP57380 is a selective low-molecular weight, non cytotoxic inhibitor of Mnk2 (Mnk2a or Mnk2b) or Mnk1. The addition of CGP57380 to cell culture cells transfected with Mnk2 (Mnk2a or Mnk2b) or Mnk1 resulted in a strong reduction in phosphorylated eIF4E.

So far, it has not been described that Mnk kinases are involved in the regulation of body-weight and thermogenesis, and thus may be associated with metabolic diseases such as obesity, as well as related disorders such as eating disorder, cachexia, diabetes mellitus, hypertension, coronary heart disease, hypercholesterolemia, dyslipidemia, osteoarthritis, gallstones, and sleep apnea, and disorders related to ROS defence, such as diabetes mellitus, neurodegenerative disorders, and cancer, e.g. cancers of the reproductive organs. In this application we demonstrate that the correct gene doses of Mnk kinases are essential for maintenance of energy homeostasis. A genetic screen was used to identify that mutation of Mnk kinase homologous genes causes obesity, reflected by a significant increase of triglyceride content, the major energy storage substance. Furthermore, in this invention we relate to mutations of Mnk kinases that affect the activity of uncoupling proteins (UCPs), thereby leading to an altered mitochondrial activity. We also relate to the treatment of metabolic disorders with the Mnk-specific inhibitor CGP57380 and derivatives thereof.

In this invention we demonstrate that the correct gene dose of the *Drosophila melanogaster* homologue of Mnk is essential for maintenance of energy homeostasis in adult flies and for the activity of mitochondrial uncoupling protein. A genetic screen was used to identify that mutation of an Mnk homologous gene causes obesity in *Drosophila melanogaster*, reflected by a significant increase of triglyceride content, the major energy storage substance. In a second screen designed to identify factors that modulate activity of uncoupling protein, we discovered that mutation of this Mnk homologous gene caused a reduction the activity of uncoupling protein. Thus, the invention is also based on the finding that the *Drosophila* homologue of Mnk is contributing to membrane stability and/or function of organelles, preferably mitochondria. It was found that mutations in LK6 kinases affect the activity of uncoupling proteins (UCPs), thereby leading to an altered mitochondrial activity.

Further, we show that the mouse homologue of the Mnk2 gene is regulated by fasting and by genetically induced obesity. Furthermore, the Mnk2 mRNA is strongly upregulated during adipocyte differentiation in vitro (see EXAMPLES). This invention shows that Mnk2 transcripts are expressed in most mouse tissues but with highest expression levels in white (WAT) and brown adipose tissue (BAT). The expression in white adipose tissue is reduced by approx. 60% in fasted mice and in ob/ob mice. The analysis of actin-mMnk2DN transgenic mice showed that the ectopic expression of mMnk2DN transgene (see Examples) leads to an clear increase in bodyweight. The effect seems to be diet-independent, as it can be seen on control diet as well as on high fat diet. Thus, we conclude that Mnk2 is playing an important role in the regulation of body-weight.

In addition, we found that the relative expression levels of both human Mnk2 splice variants is the same for all tissues analyzed. Both Mnk2 variants show highest expression levels in human tissues relevant for metabolic disorders namely adipose and muscle tissue. Furthermore, both Mnk2 variants are upregulated during human adipocyte differentiation. Thus, we conclude that Mnk2 (or variants thereof) has a function in the metabolism of mature human adipocytes.

We also found that cellular triglyceride levels in Mnk2 overexpressing cells were significantly lower from day 4 to day 12 of adipogenesis compared to that in the control cells. Furthermore, Mnk2 overexpressing cells were less effective at synthesizing lipids from exogenous glucose. Consequently, the levels of insulin stimulated lipid synthesis are significantly lower at day 12 of adipogenesis when compared to control cells. We also found that transport of exogenous fatty acids across the plasma membrane of Mnk2 overexpressing cells and hence esterification of these metabolites was considerably lower at day 12 of adipogenesis when compared to control cells.

Polynucleotides encoding a protein with homologies to proteins of the Mnk kinase family are suitable to investigate diseases and disorders as described above. Discovery of molecules related to Mnk kinases satisfies a need in the art by providing new compositions useful in diagnosis, treatment, and prognosis of diseases and disorders as described above.

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention, which will be limited only by the appended claims. Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies, which are reported in the publications which might be used in connection with the invention. Nothing herein is to be construed as an admission that the invention is not entitled to antedate such disclosure.

The present invention discloses that Mnk homologous proteins are regulating the energy homeostasis and fat metabolism, especially the metabolism and storage of triglycerides, and polynucleotides, which identify and encode the proteins disclosed in this invention. The present invention also discloses that Mnk homologous proteins are directly or indirectly involved in membrane stability and/or function of organelles, in particular mitochondria, and polynucleotides, which identify and encode the proteins disclosed in this invention. The invention also relates to vectors, host cells, antibodies, and recombinant methods for producing the polypeptides and polynucleotides of the invention. The invention also relates to the use of these sequences in the diagnosis, study, prevention, and treatment of diseases and disorders related to body-weight regulation and thermogenesis, for example, but not limited to, metabolic diseases such as obesity, as well as related disorders such as eating disorder, cachexia, diabetes mellitus, hypertension, coronary heart disease, hypercholesterolemia, dyslipidemia, osteoarthritis, gallstones, and sleep apnea, and disorders related to ROS defence, such as diabetes mellitus, neurodegenerative disorders, and cancer, e.g. cancers of the reproductive organs.

Mnk homologous proteins and nucleic acid molecules coding therefore are obtainable from insect or vertebrate species, e.g. mammals or birds. Particularly preferred are human Mnk homologous polypeptides and nucleic acids encoding such polypeptides, particularly polypeptides and nucleic acids encoding a human Mnk2 protein (splice variant Mnk2a (SEQ ID NO.: 2) encoded by the nucleic acid sequence having Genbank Accession No. AF237775 (SEQ ID NO.: 1) as shown in FIGS. 3D and 3E, or splice variant Mnk2b (SEQ ID NO.: 4) encoded by the nucleic acid sequences having GenBank Accession AF237776 (SEQ ID NO.: 3) or No. NM_017572.2 (SEQ ID NO.: 55), as shown in FIGS. 3F and 3G. Genbank Accession No. AF237775 (SEQ ID NO.: 1) is identical to formerly Genbank Accession No. XM_030637 which was removed at the submitters request; see a Clustal W multiple sequence alignment in FIG. 3B, see also sequences in FIGS. 3D-G) or a human Mnk1 protein (SEQ ID NO.: 6) encoded by the nucleic acid sequences having Genbank Accession No. AB000409.1 (SEQ ID NO.: 56) and NM_003684.2 (SEQ ID NO.: 5) as shown in FIGS. 3H and 3I); Genbank Accession No. AB000409 is identical to formerly Genbank Accession No. XM_001600 which was removed at the submitters request; see a Clustal W multiple sequence alignment in FIG. 3C).

The invention particularly relates to a nucleic acid molecule encoding a polypeptide contributing to regulating the energy homeostasis and the metabolism of triglycerides, and/or contributing to membrane stability and/or function of organelles, wherein said nucleic acid molecule comprises (a) the nucleotide sequences of Genbank Accession Nos. AF237775 (SEQ ID NO.: 1), NM_017572.2 (SEQ ID NO.: 55), AB000409.1 (SEQ ID NO.: 56), or NM_003684.2 (SEQ ID NO.: 5), and/or the complement thereof, (b) a nucleotide sequence which hybridizes at 50° C. in a solution containing 1×SSC and 0.1% SDS to the nucleic acid molecule of (a), particularly a nucleic acid encoding the amino acid sequences as shown in FIG. 3, (c) a sequence corresponding to the sequences of (a) or (b) within the degeneration of the genetic code, (d) a sequence which encodes a polypeptide which is at least 85%, preferably at least 90%, more preferably at least 95%, more preferably at least 98% and up to 99.6% identical to the amino acid sequences shown in FIG. 3, (e) a sequence which differs from the nucleic acid molecule of (a) to (d) by mutation and wherein said mutation causes an alteration, deletion, duplication or premature stop in the encoded polypeptide or (f) a partial sequence of any of the nucleotide sequences of (a) to (e) having a length of at least 15 bases, preferably at least 20 bases, more preferably at least 25 bases and most preferably at least 50 bases.

The invention is based on the finding that Mnk homologous proteins (herein referred to as Mnk), particularly Mnk2 (Mnk2a or Mnk2b) or Mnk1, and the polynucleotides encoding these, are involved in the regulation of triglyceride storage and therefore energy homeostasis. The present invention also discloses that Mnk homologous proteins are directly or indirectly involved in membrane stability and/or function of organelles, in particular mitochondria, and polynucleotides, which identify and encode the proteins disclosed in this invention. The invention describes the use of compositions comprising the nucleotides, proteins or effectors thereof, e.g. antibodies, aptamers, anti-sense molecules, ribozymes, RNAi molecules, peptides, low-molecular weight organic molecules and other receptors recognizing the nucleic acid molecule or the polypeptide, for the diagnosis, study, prevention, or treatment of diseases and disorders related to bodyweight regulation and thermogenesis, for example, but not limited to, metabolic diseases such as obesity, as well as related disorders such as eating disorder, cachexia, diabetes mellitus, hypertension, coronary heart disease, hypercholesterolemia, dyslipidemia, osteoarthritis, gallstones, and sleep apnea, and disorders related to ROS defence, such as diabetes mellitus, neurodegenerative disorders, and cancer, e.g. cancers of the reproductive organs.

Accordingly, the present invention relates to genes with novel functions in body-weight regulation, energy homeostasis, metabolism, and obesity. To find genes with novel functions in energy homeostasis, metabolism, and obesity, a functional genetic screen was performed with the model organism *Drosophila melanogaster* (Melgen). *Drosophila melanogaster* is one of the most intensively studied organisms in biology and serves as a model system for the investigation of many developmental and cellular processes common to higher eukaryotes, including humans (see, for example, Adams et al., Science 287: 2185-2195 (2000)). The success of *Drosophila melanogaster* as a model organism is largely due to the power of forward genetic screens to identify the genes that are involved in a biological process (see, Johnston Nat Rev Genet 3: 176-188 (2002); Rorth, Proc Natl Acad Sci USA 93: 12418-12422 (1996)). One resource for screening was a proprietary *Drosophila melanogaster* stock collection of EP-lines. The P-vector of this collection has Gai4-UAS-binding sites fused to a basal promoter that can transcribe adjacent genomic *Drosophila* sequences upon binding of Gal4 to UAS-sites. This enables the EP-line collection for overexpression of endogenous flanking gene sequences. In addition, without activation of the UAS-sites, integration of the EP-element into the gene is likely to cause a reduction of gene activity, and allows determining its function by evaluating the loss-of-function phenotype.

Triglycerides are the most efficient storage for energy in cells, and are significantly increased in obese patients. In this invention, we have used a genetic screen to identify, that mutations of Lk6 homologous genes cause changes in the body weight which is reflected by a significant change in the triglyceride levels. In order to isolate genes with a function in energy homeostasis, several thousand EP-lines were tested for their triglyceride content after a prolonged feeding period. Lines with significantly changed triglyceride content were selected as positive candidates for further analysis. In this invention, the content of triglycerides of a pool of flies with the same genotype after feeding for six days was analyzed using a triglyceride assay, as, for example, but not for limiting the scope of the invention, is described below in the examples section. The change of triglyceride content due to the loss of a gene function suggests gene activities in energy homeostasis in a dose dependent manner that controls the amount of energy stored as triglycerides.

The result of the triglyceride content analysis is shown in FIG. 1. Flies homozygous for EP(3)3333 and EP(3)3576 integrations were analyzed in the triglyceride assay. The average increase of triglyceride content of the homozygous viable lines EP(3)3333 and EP(3)3576 is approx. 140% (FIG. 1). Therefore, the very likely loss of a gene activity in the gene locus 86F7 (estimated, chromosomal localisation where the EP-vector of EP(3)3333 and EP(3)3576 flies is integrated) is responsible for changes in the metabolism of the energy storage triglycerides, therefore representing in both cases an obese fly model. The increase of triglyceride content due to the loss of a gene function suggests gene activities in energy homeostasis in a dose dependent manner that controls the amount of energy stored as triglycerides.

Figure 2:
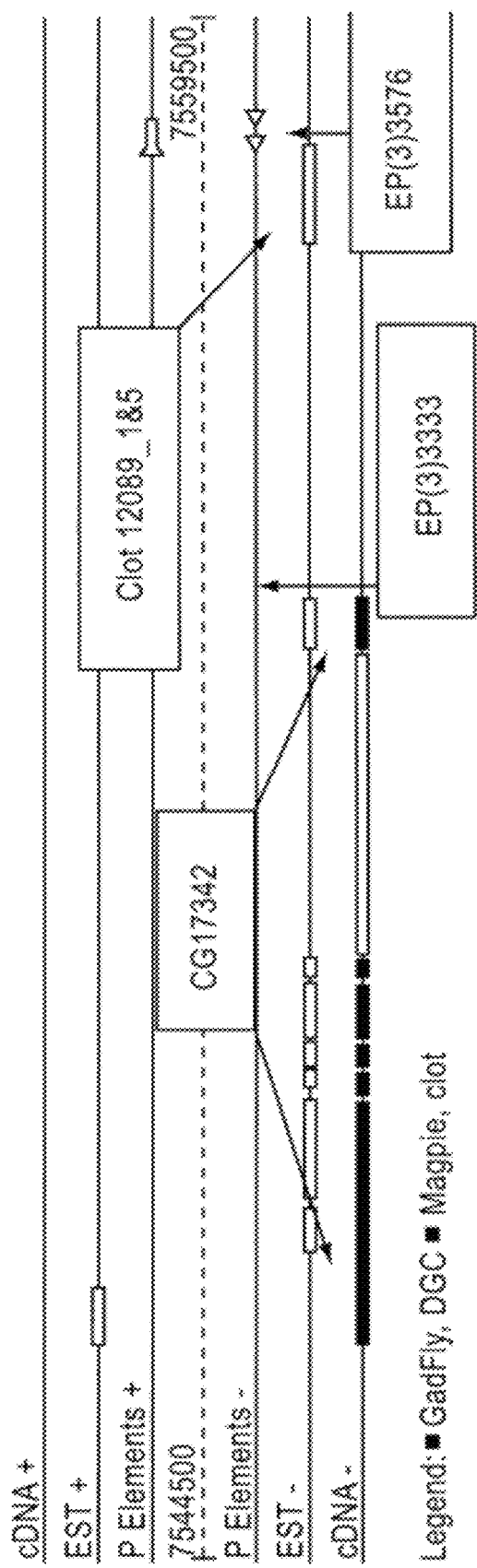
FIG. 2 shows the molecular organization of the mutated LK6 gene locus. The dotted black line represents the position of the cDNA (from position 7544500 to 7559500 on chromosome 3R) that includes the integration sites of EP(3)3333 and EP(3)3576. Transcribed DNA sequences (ESTs) and predicted exons are shown as bars in the lower two lines. Predicted exons of gene CG17342 (GadFly, Lk6) are shown as black bars and introns as open bars. Lk6 encodes for a gene that is predicted by GadFly sequence analysis programs as Gadfly Accession Number CG17342.

Nucleic acids encoding the Mnk protein of the present invention were identified using a plasmid-rescue technique. Genomic DNA sequences were isolated that are localized directly 3' to the EP(3)3333 and EP(3)3576 integrations. Using those isolated genomic sequences public databases like Berkeley *Drosophila* Genome Project (GadFly; see also FlyBase (1999) Nucleic Acids Research 27:85-88) were screened thereby confirming the integration side of EP(3)3333 in the 5' region of a 5' exon of the Mnk homologous gene and EP(3)3576 in the 5' region of an alternative 5' exon (FIG. 2). FIG. 2 shows the molecular organization of this locus. Genomic DNA sequence is represented by the assembly as a black dotted line in the middle that includes the integration site of EP(3)3333 and EP(3)3576. Numbers represent the coordinates of the genomic DNA (starting at position 7544500 on chromosome 3R). Grey bars on the two "cDNA"-lines represent the predicted genes (Gad Fly & Magpie), and grey symbols on the "P-Elements"-line the EP-vector integration sites. Predicted exons of gene CG17342 are shown as dark grey bars and predicted introns as light grey bars.

Lk6 (the Mnk homologous gene in *Drosophila*) encodes for a gene that is predicted by GadFly sequence analysis programs (GadFly Accession Number CG17342). No functional data described the regulation of obesity and metabolic diseases are available in the prior art for the genes shown in FIG. 3, referred to as Mnk in the present invention.

It is also preferred that the nucleic acid molecule encodes a polypeptide contributing to membrane stability and/or function of organelles and represents a protein of *Drosophila* which has been found to be able to modify UCPs, see also appended examples. As demonstrated in the appended examples, the here described polypeptide (and encoding nucleic acid molecule) was able to modify, e.g. enhance a specific eye phenotype in *Drosophila* which was due to the overexpression of the *Drosophila melanogaster* gene dUCPy. The overexpression of dUCPy (with homology to human UCPs) in the compound eye of *Drosophila* led to a clearly visible eye defect which can be used as a "read-out" for a genetical" modifier screen".

In said "modifier screen" thousands of different genes are mutagenized to modify their expression in the eye. Should one of the mutagenized genes interact with dUCPy and modify its activity an enhancement or suppression of the eye defect will occur. Since such flies are easily to discern they can be selected to isolate the interacting gene. As shown in the appended examples, a gene was deduced that can enhance the eye defect induced by the activity of dUCPy. This gene is called the LK6 gene of *Drosophila* with high homologies to the human Mnk proteins, as described above. It is envisaged that mutations in the herein described Mnk-polypeptides (and genes) lead to phenotypic and/or physiological chances which may comprise a modified and altered mitochondrial activity. This, in turn, may lead to, inter alia, an altered energy metabolism, altered thermogenesis and/or altered energy homeostasis. As shown in the appended examples, a gene was deduced that can enhance the eye defect induced by the activity of dUCPy.

Mnk homologous proteins and nucleic acid molecules coding therefor are obtainable from insect or vertebrate species, e.g. mammals or birds. Particularly preferred are nucleic acids encoding the human Lk6/Mnk homologs, particularly Mnk2 variants (Mnk2a or Mnk2b) or Mnk1. The present invention is describing a polypeptide comprising the amino acid sequence of Mnk, particularly Mnk2 variants (Mnk2a or Mnk2b) or Mnk1. A comparison (Clustalx1.8) between the Mnk proteins of different species (human and *Drosophila*) was conducted and is shown in FIG. 3A. Based upon homology, Mnk protein of the invention and each homologous protein or peptide may share at least some activity.

In a particular embodiment, the invention encompasses the polynucleotide comprising the nucleic acid sequence of Gen-Bank Accession Number AF237775 (SEQ ID NO.: 1), NM_017572.1 (SEQ ID NO.: 3), AB000409.1 (SEQ ID NO.: 56), or NM_003684.2 (SEQ ID NO.: 5). It will be appreciated by those skilled in the art that as a result of the degeneracy of the genetic code, a multitude of nucleotide sequences encoding Mnk, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequences of naturally occurring Mnk, and all such variations are to be considered as being specifically disclosed. Although nucleotide sequences which encode Mnk and its variants are preferably capable of hybridizing to the nucleotide sequences of the naturally occurring Mnk under appropriately selected conditions of stringency, it may be advantageous to produce nucleotide sequences encoding Mnk or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding Mnk and its derivatives without altering the encoded amino acid sequences include the production of RNA transcripts having more desirable properties, such as a greater half-life, than transcripts produced from the naturally occurring sequences. The invention also encompasses production of DNA sequences, or portions thereof, which encode Mnk and its derivatives, entirely by synthetic chemistry. After production, the synthetic sequence may be inserted into any of the many available expression vectors and cell systems using reagents that are well known in the art at the time of the filing of this application. Moreover, synthetic chemistry may be used to introduce mutations into a sequence encoding Mnk any portion thereof.

Also encompassed by the invention are polynucleotide sequences that are capable of hybridizing to the claimed nucleotide sequences, and in particular, those shown in Gen-Bank Accession Numbers AF237775 (SEQ ID NO.: 1), NM_017572.1 (SEQ ID NO.: 3), AB000409.1 (SEQ ID NO.: 56), or NM_003684.2 (SEQ ID NO.: 5), under various conditions of stringency. Hybridization conditions are based on the melting temperature (Tm) of the nucleic acid binding complex or probe, as taught in Wahl, G. M. and S. L. Berger (1987: Methods Enzymol. 152:399-407) and Kimmel, A. R. (1987; Methods Enzymol. 152:507-511), and may be used at a defined stringency. Preferably, hybridization under stringent conditions means that after washing for 1 h with 1×SSC and 0.1% SDS at 50° C., preferably at 55° C., more preferably at 62° C. and most preferably at 68° C., particularly for 1 h in 0.2×SSC and 0.1% SDS at 50° C., preferably at 55° C., more preferably at 62° C. and most preferably at 68° C., a positive hybridization signal is observed. Altered nucleic acid sequences encoding Mnk which are encompassed by the invention include deletions, insertions, or substitutions of different nucleotides resulting in a polynucleotide that encodes the same or a functionally equivalent Mnk.

The encoded proteins may also contain deletions, insertions, or substitutions of amino acid residues, which produce a silent change and result in a functionally equivalent Mnk. Deliberate amino acid substitutions may be made on the basis of similarity in polarity, charge, solubility, hydrophobicity, hydrophilicity, and/or the amphipathic nature of the residues as long as the biological activity of Mnk is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the genes encoding Mnk. As used herein, an "allele" or "allelic sequence" is an alternative form of the gene, which may result from at least one mutation in the nucleic acid sequence. Alleles may result in altered mRNAs or polypeptides whose structures or function may or may not be altered. Any given gene may have none, one, or many allelic forms. Common mutational changes, which give rise to alleles, are generally ascribed to natural deletions, additions, or substitutions of nucleotides. Each of these types of changes may occur alone, or in combination with the others, one or more times in a given sequence. Methods for DNA sequencing which are well known and generally available in the art may be used to practice any embodiments of the invention. The methods may employ such enzymes as the Klenow fragment of DNA polymerase I, SEQUENASE DNA Polymerase (US Biochemical Corp, Cleveland Ohio), Taq polymerase (Perkin Elmer), thermostable T7 polymerase (Amersham, Chicago, Ill.), or combinations of recombinant polymerases and proofreading exonucleases such as the ELONGASE Amplification System (GIBCO/BRL, Gaithersburg, Md.). Preferably, the process is automated with machines such as the Hamilton MICROLAB 2200 (Hamilton, Reno Nev.), Peltier thermal cycler (PTC200; MJ Research, Watertown, Mass.) and the ABI 377 DNA sequencers (Perkin Elmer). The nucleic acid sequences encoding Mnk may be extended utilising a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318-322). Inverse PCR may also be used to amplify or extend sequences using divergent primers based on a known region (Triglia, T. et al. (1988) Nucleic Acids Res. 16:8186). Another method which may be used is capture PCR which involves PCR amplification of DNA fragments adjacent to a known sequence in human and yeast artificial chromosome DNA (Lagerstrom, M. et al. (PCR Methods Applic. 1: 111-119). Another method which may be used to retrieve unknown sequences is that of Parker, J. D. et al. (1991; Nucleic Acids Res. 19:3055-3060). Additionally, one may use PCR, nested primers, and PRO-MOTERFINDER libraries to walk in genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences, which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions. Capillary electrophoresis systems, which are commercially available, may be used to analyse the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA, which might be present in limited amounts in a particular sample.

In another embodiment of the invention, polynucleotide sequences or fragments thereof which encode Mnk, or fusion proteins or functional equivalents thereof, may be used in recombinant DNA molecules to direct expression of Mnk in appropriate host cells. Due to the inherent degeneracy of the genetic code, other DNA sequences, which encode substantially the same, or a functionally equivalent amino acid sequence may be produced and these sequences may be used to clone and express Mnk. As will be understood by those of skill in the art, it may be advantageous to produce Mnk-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life, which is longer than that of a transcript generated from the naturally occurring sequence. The nucleotide sequences of the present invention can be engineered using methods generally known in the art in order to alter Mnk encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences encoding Mnk may be ligated to a heterologous sequence to encode a fusion protein. For example, to screen peptide libraries for inhibitors of Mnk activities, it may be useful to construct chimeric Mnk proteins that can be recognized by commercially available antibodies. A fusion protein may also be engineered to contain a cleavage site located between the Mnk encoding sequence and the heterologous protein sequences, so that Mnk may be cleaved and purified away from the heterologous moiety. In another embodiment, sequences encoding Mnk may be synthesized, in whole or in part, using chemical methods well known in the art (see Caruthers et al. (1980) Nucl. Acids Res. Symp. Ser. 7:215-223, Horn et al. (1980) Nucl. Acids Res. Symp. Ser. 7:225-232). Alternatively, the proteins themselves may be produced using chemical methods to synthesize the amino acid sequence of Mnk, or a portion thereof. For example, peptide synthesis can be performed using various solid-phase techniques (Roberge et al. (1995) Science 269:202-204) and automated synthesis may be achieved, for example, using the ABI431A peptide synthesizer (Perkin Elmer). The newly synthesized peptide may be substantially purified by preparative high performance liquid chromatography (e.g., Creighton, T. (1983) Proteins, Structures and Molecular Principles, WH Freeman and Co., New York, N.Y.). The composition of the synthetic peptides may be confirmed by amino acid analysis or sequencing (e.g., the Edman degradation procedure; Creighton, supra). Additionally, the amino acid sequences of Mnk, or any part thereof, may be altered during direct synthesis and/or combined using chemical methods with sequences from other proteins, or any part thereof, to produce a variant polypeptide.

In order to express a biologically active Mnk, the nucleotide sequences encoding Mnk functional equivalents, may be inserted into appropriate expression vectors, i.e., a vector, which contains the necessary elements for the transcription and translation of the inserted coding sequence. Methods, which are well known to those skilled in the art, may be used to construct expression vectors containing sequences encoding Mnk and appropriate transcriptional and translational control elements. These methods include in vitro recombinant DNA techniques, synthetic techniques, and in vivo genetic recombination. Such techniques are described in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y.

Regulatory elements include for example a promoter, an initiation codon, a stop codon, a mRNA stability regulatory element, and a polyadenylation signal. Expression of a polynucleotide can be assured by (i) constitutive promoters such as the Cytomegalovirus (CMV) promoter/enhancer region, (ii) tissue specific promoters such as the insulin promoter (see, Soria et al., 2000, Diabetes 49:157), SOX2 gene promoter (see Li et al., 1998, Curr. Biol. 8:971-4), Msi-1 promoter (see Sakakibara et al., 1997, J. Neuroscience 17:8300-8312), alpha-cardia myosin heavy chain promoter or human atrial natriuretic factor promoter (Kiug et al., 1996, J. Clin. Invest 98:216-24; Wu et al., 1989, J. Biol. Chem. 264:6472-79) or (iii) inducible promoters such as the tetracycline inducible system. Expression vectors can also contain a selection agent or marker gene that confers antibiotic resistance such as the neomycin, hygromycin or puromycin resistance genes. These methods include in vitro recombinant DNA techniques, synthetic techniques, and in vivo genetic recombination. Such techniques are described in Sambrook, J. et al. (1989) Molecular Cloning, A Laboratory Manual, Cold Spring Harbor Press, Plainview, N.Y. and Ausubel, F. M. et al. (1989) Current Protocols in Molecular Biology, John Wiley & Sons, New York, N.Y. In a further embodiment of the invention, natural, modified or recombinant nucleic acid sequences encoding the proteins of the invention and homologous proteins may be ligated to a heterologous sequence to encode a fusion protein.

A variety of expression vector/host systems may be utilized to contain and express sequences encoding the proteins or fusion proteins. These include, but are not limited to, micro-organisms such as bacteria transformed with recombinant bacteriophage, plasmid or cosmid DNA expression vectors; yeast transformed with yeast expression vectors; insect cell systems infected with virus expression vectors (e.g., baculovirus, adenovirus, adeno-associated virus, lentivirus, retrovirus); plant cell systems transformed with virus expression vectors (e.g., cauliflower mosaic virus, CaMV; tobacco mosaic virus, TMV) or with bacterial expression vectors (e.g., Ti or PBR322 plasmids); or animal cell systems.

The "control elements" or "regulatory sequences" are those non-translated regions of the vectors, e.g. enhancers, promoters, 5' and 3' untranslated regions, which interact with host cellular proteins to carry out transcription and translation. Such elements may vary in their strength and specificity. Depending on the vector system and host utilised, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Gibco BRL) and the like may be used. The baculovirus polyhedrin promoter may be used in insect cells. Promoters and enhancers derived from the genomes of plant cells (e.g., heat shock, RUBISCO; and storage protein genes) or from plant viruses (e.g., viral promoters and leader sequences) may be cloned into the vector. In mammalian cell systems, promoters from mammalian genes or from mammalian viruses are preferable. If it is necessary to generate a cell line that contains multiple copies of the sequences encoding Mnk, vectors based on SV40 or EBV may be used with an appropriate selectable marker.

In bacterial systems, a number of expression vectors may be selected depending upon the use intended for Mnk. For example, when large quantities of Mnk are needed for the induction of antibodies, vectors, which direct high level expression of fusion proteins that are readily purified, may be used. Such vectors include, but are not limited to, the multifunctional E. coli cloning and expression vectors such as the BLUESCRIPT phagemid (Stratagene), in which the sequence encoding Mnk may be ligated into the vector in frame with sequences for the amino-terminal Met and the subsequent 7 residues of r3-galactosidase so that a hybrid protein is produced; piN vectors (Van Heeke, G. and S. M. Schuster (1989) J. Biol. Chem. 264:5503-5509); and the like. Vectors of the pGEX series (Amersham Biosciences, Uppsala, Sweden) may also be used to express foreign polypeptides as fusion proteins with Glutathione S-Transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will. In the yeast, *Saccharomyces cerevisiae*, a number of vectors containing constitutive or inducible promoters such as alpha factor, alcohol oxidase, and PGH may be used. For reviews, see Ausubel et al., (supra) and Grant et al. (1987) Methods Enzymol. 153:516-544.

In cases where plant expression vectors are used, the expression of sequences encoding Mnk may be driven by any of a number of promoters. For example, viral promoters such as the 35S and 19S promoters of CaMV may be used alone or in combination with the omega leader sequence from TMV (Takamatsu, N. (1987) EMBO J. 6:307-311). Alternatively, plant promoters such as the small subunit of RUBISCO or heat shock promoters may be used (Coruzzi, G. et al. (1984) EMBO J. 3:1671-1680; Broglie, R. et al. (1984) Science 224:838-843; and Winter, J. et al. (1991) Results Probl. Cell Differ. 17: 85-105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191-196).

An insect system may also be used to express Mnk. For example, in one such system, *Autographa californica* nuclear polyhedrosis virus (AcNPV) is used as a vector to express foreign genes in *Spodoptera frugiperda* cells or in *Trichoplusia larvae*. The sequences encoding Mnk may be cloned into a non-essential region of the virus, such as the polyhedrin gene, and place under control of the polyhedrin promoter. Successful insertions of Mnk will render the polyhedrin gene inactive and produce recombinant virus lacking coat protein. The recombinant viruses may then be used to infect, for example, *S. frugiperda* cells of *Trichoplusia larvae* in which Mnk may be expressed (Engelhard, E. K. et al. (1994) Proc. Nat. Acad. Sci. 91:3224-3227).

In mammalian host cells, a number of viral-based expression systems may be utilised. In cases where an adenovirus is used as an expression vector, sequences encoding Mnk may be ligated into an adenovirus transcription/translation complex consisting of the late promoter and tripartite leader sequence. Insertion in a non-essential E1 or E3 region of the viral genome may be used to obtain viable viruses which are capable of expressing Mnk in infected host cells (Logan, J. and Shenk, T. (1984) Proc. Natl. Acad. Sci. 81:3655-3659). In addition, transcription enhancers, such as the Rous sarcoma virus (RSV) enhancer, may be used to increase expression in mammalian host cells.

Specific initiation signals may also be used to achieve more efficient translation of sequences encoding Mnk. Such signals include the ATG initiation codon and adjacent sequences. In cases where sequences encoding Mnk, its initiation codons, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125-162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, He La, MOCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines, which stably express Mnk may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells, which successfully express the introduced sequences. Resistant clones of stably transformed cells may be proliferated using tissue culture techniques appropriate to the cell type. Any number of selection systems may be used to recover transformed cell lines. These include, but are not limited to, the herpes simplex virus thymidine kinase (Wigler, M. et al. (1977) Cell 11:223-32) and adenine phosphoribosyltransferase (Lowy, I. et al. (1980) Cell 22:817-23) genes, which can be employed in tk$^-$ or aprt$^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567-70); npt, which confers resistance to the aminoglycosides neomycin and G-418 (Colbere-Garapin, F. et al (1981) J. Mol. Biol. 150:1-14) and als or pat, which confer resistance to chlorsulfuron and phosphinothricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:804 7-51). Recently, the use of visible markers has gained popularity with such markers as anthocyanins, β-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55: 121-131).

In vivo, the enzymatic kinase activity of the unmodified polypeptides of Mnk towards a substrate can be enhanced by appropriate stimuli, triggering the phosphorylation of Mnk. This may be induced in the natural context by extracellular or intracellular stimuli, such as signaling molecules or environmental influences. One may generate a system containing active Mnk, may it be an organism, a tissue, a culture of cells or cell-free environment, by exogenously applying this stimulus or by mimicking this stimulus by a variety of the techniques, some of them described further below. A system containing activated Mnk may be produced (i) for the purpose of diagnosis, study, prevention, and treatment of diseases and disorders related to body-weight regulation and thermogenesis, for example, but not limited to, metabolic diseases such as obesity, as well as related disorders such as eating disorder, cachexia, diabetes mellitus, hypertension, coronary heart disease, hypercholesterolemia, dyslipidemia, osteoarthritis, gallstones, and sleep apnea, and disorders related to ROS defence, such as diabetes mellitus, neurodegenerative disorders, and cancer, e.g. cancers of the reproductive organs, (ii) for the purpose of identifying or validating therapeutic candidate agents, pharmaceuticals or drugs that influence the genes of the invention or their encoded polypeptides, (iii) for the purpose of generating cell lysates containing activated polypeptides encoded by the genes of the invention, (iv) for the purpose of isolating from this source activated polypeptides encoded by the genes of the invention.

In one embodiment of the invention, one may produce activated Mnk independent of the natural stimuli for the above said purposes by, for example, but not limited to, (i) an agent that mimics the natural stimulus; (ii) an agents, that acts downstream of the natural stimulus, such as activators of the MAP kinase pathway, phorbol ester, anisomycin, constitutive active alleles of the MAP kinase kinase kinases, of the MAP kinase kinases, of the MAP kinase or Mnk itself as they are described or may be developed; (iii) by introduction of single or multiple amino acid substitutions, deletions or insertions within the sequence of Mnk to yield constitutive active forms; (iv) by the use of isolated fragments of Mnk. In addition, one may generate enzymatically active Mnk in an ectopic system, prokaryotic or eukaryotic, in vivo or in vitro, by co-transferring the activating components to this system. These could be, for example, but not limited to, components of the MAP kinase pathway such as constitutive active alleles of the MAP kinase kinases Mek1 or Mkk6, together with the MAP kinases ERK1 or ERK2 or the p38 MAPK isoforms. For example, one may activate isolated Mnk protein in solution with a mutant polypeptide of Mek1 containing the amino acid substitutions S218D and S222E together with isolated ERK2 kinase in the presence of 1.0 mM adenosine triphosphate and suitable buffer conditions such as 50 mM N-(2-Hydroxyethyl)-piperazine-N'-(2-ethanesulfonic acid)/potassium hydroxide pH 7.4, 5 mM magnesium chloride, 0.5 mM dithiothreitol (see FIG. 14).

Although the presence/absence of marker gene expression suggests that the gene of interest is also present, its presence and expression may need to be confirmed. For example, if the sequences encoding Mnk are inserted within a marker gene sequence, recombinant cells containing sequences encoding Mnk can be identified by the absence of marker gene function. Alternatively, a marker gene can be placed in tandem with sequences encoding Mnk under the control of a single promoter. Expression of the marker gene in response to induction or selection usually indicates expression of the tandem gene as well. Alternatively, host cells, which contain the nucleic acid sequences encoding Mnk and express Mnk, may be identified by a variety of procedures known to those of skill in the art. These procedures include, but are not limited to, DNA-DNA, or DNA-RNA hybridization and protein bioassay or immunoassay techniques, which include membrane, solution, or chip based technologies for the detection and/or quantification of nucleic acid or protein.

The presence of polynucleotide sequences encoding Mnk can be detected by DNA-DNA or DNA-RNA hybridization or amplification using probes or portions or fragments of polynucleotides encoding Mnk. Nucleic acid amplification based assays involve the use of oligonucleotides or oligomers based on the sequences encoding Mnk to detect transformants containing DNA or RNA encoding Mnk. As used herein "oligonucleotides" or "oligomers" refer to a nucleic acid sequence of at least about 10 nucleotides and as many as about 60 nucleotides, preferably about 15 to 30 nucleotides, and more preferably about 20-25 nucleotides, which can be used as a probe or amplimer.

A variety of protocols for detecting and measuring the expression of Mnk, using either polyclonal or monoclonal antibodies specific for the protein are known in the art. Examples include enzyme-linked immunosorbent assay (ELISA), radioimmunoassay (RIA), and fluorescence activated cell sorting (FAGS). A two-site, monoclonal-based immunoassay utilizing monoclonal antibodies reactive to two non-interfering epitopes on Mnk is preferred, but a competitive binding assay may be employed. These and other assays are described, among other places, in Hampton, R. et al. (1990; Serological Methods, a Laboratory Manual, APS Press, St Paul, Minn.) and Maddox, D. E. et al. (1983; J. Exp. Med. 158: 1211-1216).

A wide variety of labels and conjugation techniques are known by those skilled in the art and may be used in various nucleic acid and amino acid assays. Means for producing labelled hybridization or PCR probes for detecting sequences related to polynucleotides encoding Mnk include oligo-labelling, nick translation, end-labelling or PCR amplification using a labelled nucleotide.

Alternatively, the sequences encoding Mnk, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labelled nucleotides. These procedures may be conducted using a variety of commercially available kits (Pharmacia & Upjohn, (Kalamazoo, Mich.); Promega (Madison Wis.); and U.S. Biochemical Corp., (Cleveland, Ohio).

Suitable reporter molecules or labels, which may be used, include radionuclides, enzymes, fluorescent, chemiluminescent, or chromogenic agents as well as substrates, co-factors, inhibitors, magnetic particles, and the like.

Host cells transformed with nucleotide sequences encoding Mnk may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode Mnk may be designed to contain signal sequences, which direct secretion of Mnk through a prokaryotic or eukaryotic cell membrane. Other recombinant constructions may be used to join sequences encoding Mnk to nucleotide sequence encoding a polypeptide domain, which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAG extension/affinity purification system (Immunex Corp., Seattle, Wash.) The inclusion of cleavable linker sequences such as those specific for Factor XA or Enterokinase (Invitrogen, San Diego, Calif.) between the purification domain and Mnk may be used to facilitate purification. One such expression vector provides for expression of a fusion protein containing Mnk and a nucleic acid encoding 6 histidine residues preceding a Thioredoxine or an Enterokinase cleavage site. The histidine residues facilitate purification on IMIAC (immobilized metal ion affinity chromatography as described in Porath, J. et al. (1992, Prot. Exp. Purif. 3: 263-281)) while the Enterokinase cleavage site provides a means for purifying Mnk from the fusion protein. A discussion of vectors which contain fusion proteins is provided in Kroll, D. J. et al. (1993; DNA Cell Biol. 12:441-453). In addition to recombinant production, fragments of Mnk may be produced by direct peptide synthesis using solid-phase techniques (Merrifield J. (1963) J. Am. Chem. Soc. 85:2149-2154). Protein synthesis may be performed using manual techniques or by automation. Automated synthesis may be achieved, for example, using Applied Biosystems 431 A peptide synthesized (Perkin Elmer). Various fragments of Mnk may be chemically synthesized separately and combined using chemical methods to produce the full length molecule.

Diagnostics and Therapeutics

The data disclosed in this invention show that the nucleic acids and proteins of the invention and effector molecules thereof are useful in diagnostic and therapeutic applications implicated, for example but not limited to, in metabolic disorders like obesity, diabetes, eating disorders, wasting syndromes (cachexia), pancreatic dysfunctions, arteriosclerosis, coronary artery disease (CAD), and other diseases and disorders as described above. Hence, diagnostic and therapeutic uses for the Mnk proteins of the invention are, for example but not limited to, the following: (i) protein therapeutic, (ii) small molecule drug target, (iii) antibody target (therapeutic, diagnostic, drug targeting/cytotoxic antibody), (iv) diagnostic and/or prognostic marker, (v) gene therapy (gene delivery/gene ablation), (vi) research tools, and (vii) tissue regeneration in vitro and in vivo (regeneration for all these tissues and cell types composing these tissues and cell types derived from these tissues).

The nucleic acids and proteins of the invention are useful in diagnostic and therapeutic applications implicated in various diseases and disorders described above and/or other pathologies and disorders. For example, but not limited to, cDNAs encoding the Mnk proteins of the invention and particularly their human homologues may be useful in gene therapy, and the Mnk proteins of the invention and particularly their human homologues may be useful when administered to a subject in need thereof. By way of non-limiting example, the compositions of the present invention will have efficacy for treatment of patients suffering from, for example, but not limited to, in metabolic disorders like obesity, diabetes, eating disorders, wasting syndromes (cachexia), pancreatic dysfunctions, arteriosclerosis, coronary artery disease (CAD), and other diseases and disorders, particularly as described above.

The nucleic acid(s) encoding the Mnk protein(s) of the invention, or fragments thereof, may further be useful in diagnostic applications, wherein the presence or amount of the nucleic acids or the proteins are to be assessed. These materials are further useful in the generation of antibodies that bind immunospecifically to the novel substances of the invention for use in therapeutic or diagnostic methods.

For example, in one aspect, antibodies which are specific for Mnk may be used directly as an antagonist, or indirectly as a targeting or delivery mechanism for bringing a pharmaceutical agent to cells or tissue which express Mnk. The antibodies may be generated using methods that are well known in the art. Such antibodies may include, but are not limited to, polyclonal, monoclonal, chimerical, single chain, Fab fragments, and fragments produced by a Fab expression library. Neutralising antibodies, (i.e., those which inhibit dimer formation) are especially preferred for therapeutic use.

For the production of antibodies, various hosts including goats, rabbits, rats, mice, humans, and others, may be immunised by injection with Mnk any fragment or oligopeptide thereof which has immunogenic properties. Depending on the host species, various adjuvants may be used to increase immunological response. Such adjuvants include, but are not limited to, Freund's, mineral gels such as aluminium hydroxide, and surface active substances such as lysolecithin, pluronic polyols, polyanions, peptides, oil emulsions, keyhole limpet hemocyanin, and dinitrophenol. Among adjuvants used in human, BCG (Bacille Calmette-Guerin) and *Corynebacterium parvum* are especially preferable. It is preferred that the peptides, fragments, or oligopeptides used to induce antibodies to Mnk have an amino acid sequence consisting of at least five amino acids, and more preferably at least 10 amino acids. It is preferable that they are identical to a portion of the amino acid sequence of the natural protein, and they may contain the entire amino acid sequence of a small, naturally occurring molecule. Short stretches of Mnk amino acids may be fused with those of another protein such as keyhole limpet hemocyanin and antibody produced against the chimeric molecule.

Monoclonal antibodies to Mnk may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495-497; Kozbor, D. et al. (1985) J. Immunol. Methods 81:31-42; Cote, R. J. et al. Proc. Natl. Acad. Sci. 80:2026-2030; Cole, S. P. et al. (1984) Mol. Cell Biol. 62:109-120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851-6855; Neuberger, M. S. et al (1984) Nature 312:604-608; Takeda, S. et al. (1985) Nature 314:452-454). Alternatively, techniques described for the production of single chain antibodies may be adapted, using methods known in the art, to produce Mnk-specific single chain antibodies. Antibodies with related specificity, but of distinct idiotypic composition, may be generated by chain shuffling from random combinatorial immunoglobulin libraries (Burton, D. R. (1991) Proc. Natl. Acad. Sci. 88:11120-3). Antibodies may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86:3833-3837; Winter, G. et al. (1991) Nature 349:293-299).

Antibody fragments, which contain specific binding sites for Mnk, may also be generated. For example, such fragments include, but are not limited to proteolytic fragments, e.g. the F(ab')$_2$ fragments which can be produced by Pepsin digestion of the antibody molecule and the Fab fragments which can be generated by reducing the disulfide bridges of F(ab')$_2$ fragments. Alternatively, recombinant fragments may be generated. For example, Fab expression libraries may be constructed to allow rapid and easy identification of monoclonal Fab fragments with the desired specificity (Huse, W. D. et al. (1989) Science 254:1275-1281).

Various immunoassays may be used for screening to identify antibodies having the desired specificity. Numerous protocols for competitive binding and immunoradiometric assays using either polyclonal or monoclonal antibodies with established specificities are well known in the art. Such immunoassays typically involve the measurement of complex formation between Mnk and its specific antibody. A two-site, monoclonal-based immunoassay utilizing monoclonal antibodies reactive to two non-interfering Mnk epitopes is preferred, but a competitive binding assay may also be employed (Maddox, supra).

In another embodiment of the invention, the Mnk polynucleotides or any fragment thereof, or nucleic acid effector molecules, aptamers, anti-sense molecules, ribozymes or RNAi molecules, may be used for therapeutic purposes. In one aspect, aptamers, i.e. nucleic acid molecules, which are capable of binding to a Mnk protein and modulating its activity, may be generated by a screening and selection procedure involving the use of combinational nucleic acid libraries.

In a further aspect, antisense molecules to the polynucleotide encoding Mnk may be used in situations in which it would be desirable to block the transcription of the mRNA. In particular, cells may be transformed with sequences complementary to polynucleotides encoding Mnk. Thus, antisense molecules may be used to modulate Mnk activity, or to achieve regulation of gene function. Such technology is now well known in the art, and sense or antisense oligomers or larger fragments, can be designed from various locations along the coding or control regions of sequences encoding Mnk. Expression vectors derived from retroviruses, adenovirus, herpes or vaccinia viruses, or from various bacterial plasmids may be used for delivery of nucleotide sequences to the targeted organ, tissue or cell population. Methods, which are well known to those skilled in the art, can be used to construct recombinant vectors, which will express antisense molecules complementary to the polynucleotides of the gene encoding Mnk. These techniques are described both in Sambrook et al. (supra) and in Ausubel et al. supra). Genes encoding Mnk can be turned off by transforming a cell or tissue with expression vectors which express high levels of polynucleotide or fragment thereof which encodes Mnk. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing antisense molecules, e.g. DNA, RNA, or nucleic acid analogues such as PNA, to the control regions of the gene encoding Mnk, i.e., the promoters, enhancers, and introns. Oligonucleotides derived from the transcription initiation site, e.g., between positions −10 and +10 from the start site, are preferred. Similarly, inhibition can be achieved using "triple helix" base-pairing methodology. Triple helix pairing is useful because it cause inhibition of the ability of the double helix to open sufficiently for the binding of polymerases, transcription factors, or regulatory molecules. Recent therapeutic advances using triplex DNA have been described in the literature (Gee, J. E. et al. (1994) In; Huber, B. E. and B. I. Carr, Molecular and Immunologic Approaches, Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples, which may be used, include engineered hammerhead motif ribozyme molecules that can be specifically and efficiently catalyze endonucleolytic cleavage of sequences encoding Mnk. Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Effector molecules, e.g. antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding Mnk. Such DNA sequences may be incorporated into a variety of vectors with suitable RNA polymerase promoters such as T7 or SP6. Alternatively, these cDNA constructs that synthesize antisense RNA constitutively or inducibly can be introduced into cell lines, cells, or tissues. RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of non-traditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

The activity of Mnk proteins can be assayed for example by in vitro kinase assays, as described by Tschopp et al., 2000, supra or any other suitable assay principle as described below. As inhibitor of Mnk in this assay, a staurosporine derivative such as CGP57380 or CGP052088 can be used, as described by Tschopp et al., 2000, supra or Knauf et al., 2001, supra. As negative control, the compound CGP52428 which is inactive against Mnk, but displays a similar cytotoxicity as CGP052088, or any other chemical entities with kinase inhibitory activity with exception of activity against Mnk may be used. Moreover, derivatives of CGP57380 can be assayed for activity against Mnk and are substances for the treatment, prophylaxis, and diagnosis of metabolic diseases as mentioned above. Derivatives of CGP57380 could for example be generated by modification through conventional chemical, physical and biochemical means, and may be used to produce combinatorial libraries. They may be subjected to directed or random chemical modifications, such as acylation, alkylation, esterification, amidification, etc. to produce structural analogs.

Further, the invention relates to the use of Mnk kinase inhibitors or activators for the treatment, prophylaxis or diagnosis of metabolic diseases as mentioned above. Preferably, but not exclusively, the Mnk kinase inhibitors are staurosporine or pyrazole derivatives. Examples of pyrazole derivatives are described in EP-A-0 819 129 which is herein incorporated by reference. Since CGP57380 is not cytotoxic up to 30 µM, this substance may be preferably used to inhibit kinase activity, preferably Mnk2, and used as substance for the treatment, prophylaxis, and diagnosis of metabolic diseases as mentioned above.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods, which are well known in the art. Any of the therapeutic methods described above may be applied to any suitable subject including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of Mnk, antibodies to Mnk, mimetics, agonists, antagonists, or inhibitors of Mnk. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones. The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries, which facilitate processing of the active compounds into preparations which, can be used pharmaceutically. Further details on techniques for formulation and administration may be found in the latest edition of Remington's Pharmaceutical Sciences (Maack Publishing Co., Easton, Pa.). Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilising processes. The pharmaceutical composition may be provided as a salt and can be formed with many acids, including but not limited to, hydrochloric, sulphuric, acetic, lactic, tartaric, malic, succinic, etc. After pharmaceutical compositions have been prepared, they can be placed in an appropriate container and labelled for treatment of an indicated condition. For administration of Mnk, such labelling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art. For any compounds, the therapeutically effective dose can be estimated initially either in cell culture assays, e.g., of preadipocyte cell lines, or in animal models, usually mice, rabbits, dogs, or pigs. The animal model may also be used to determine the appropriate concentration range and route of administration. Such information can then be used to determine useful doses and routes for administration in humans. A therapeutically effective dose refers to that amount of active ingredient, for example Mnk fragments thereof, antibodies of Mnk, to treat a specific condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions, which exhibit large therapeutic indices, are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage from employed, sensitivity of the patient, and the route of administration. The exact dosage will be determined by the practitioner, in light of factors related to the subject that requires treatment. Dosage and administration are adjusted to provide sufficient levels of the active moiety or to maintain the desired effect. Factors, which may be taken into account, include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation. Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art employ different formulations for nucleotides than for proteins or their inhibitors. Similarly, delivery of polynucleotides or polypeptides will be specific to particular cells, conditions, locations, etc.

In another embodiment, antibodies which specifically bind Mnk may be used for the diagnosis of conditions or diseases characterized by or associated with over- or underexpression of Mnk, or in assays to monitor patients being treated with Mnk, agonists, antagonists or inhibitors. The antibodies useful for diagnostic purposes may be prepared in the same manner as those described above for therapeutics. Diagnostic assays for Mnk include methods, which utilize the antibody and a label to detect Mnk in human body fluids or extracts of cells or tissues. The antibodies may be used with or without modification, and may be labelled by joining them, either covalently or non-covalently, with a reporter molecule. A wide variety of reporter molecules, which are known in the art may be used several of which are described above.

A variety of protocols including ELISA, RIA, and FACS for measuring Mnk are known in the art and provide a basis for diagnosing altered or abnormal levels of Mnk expression. Normal or standard values for Mnk expression are established by combining body fluids or cell extracts taken from normal mammalian subjects, preferably human, with antibody to Mnk under conditions suitable for complex formation. The amount of standard complex formation may be quantified by various methods, but preferably by photometric, means. Quantities of Mnk expressed in control and disease samples e.g. from biopsied tissues are compared with the standard values. Deviation between standard and subject values establishes the parameters for diagnosing disease. Analysis of Mnk expression can also be performed by determination of Mnk activity in assay formats well known in the art and described in more detail below.

In another embodiment of the invention, the polynucleotides specific for Mnk may be used for diagnostic purposes. The polynucleotides, which may be used, include oligonucleotide sequences, antisense RNA and DNA molecules, and PNAs. The polynucleotides may be used to detect and quantitate gene expression in biopsied tissues in which expression of Mnk may be correlated with disease. The diagnostic assay may be used to distinguish between absence, presence, and excess expression of Mnk, and to monitor regulation of Mnk levels during therapeutic intervention.

In one aspect, hybridization with PCR probes which are capable of detecting polynucleotide sequences, including genomic sequences, encoding Mnk and/or closely related molecules, may be used to identify nucleic acid sequences which encode Mnk. The specificity of the probe, whether it is made from a highly specific region, e.g., unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding Mnk, alleles, or related sequences. Probes may also be used for the detection of related sequences, and should preferably contain at least 50% of the nucleotides from any of the Mnk encoding sequences. The hybridization probes of the subject invention may be DNA or RNA and derived from the nucleotide sequence of AF237775 (SEQ ID NO.: 1), NM_017572.2 (SEQ ID NO.: 55), NM_003684.2 (SEQ ID NO.: 5), or AB000409.1 (SEQ ID NO.: 56) or from a genomic sequence including promoter, enhancer elements, and introns of the naturally occurring Mnk. Means for producing specific hybridisation probes for DNAs encoding Mnk include the cloning of nucleic acid sequences encoding Mnk derivatives into vectors for the production of mRNA probes. Such vectors are known in the art, commercially available, and may be used to synthesize RNA probes in vitro by means of the addition of the appropriate RNA polymerases and the appropriate labelled nucleotides.

Hybridization probes may be labelled by a variety of reporter groups, for example, radionuclides such as $^{32}P$ or $^{35}S$, or enzymatic labels, such as alkaline phosphatase coupled to the probe via avidin/biotin coupling systems, and the like. Polynucleotide sequences encoding Mnk may be used for the diagnosis of conditions or diseases, which are associated with expression of Mnk. Examples of such conditions or diseases include, but are not limited to, pancreatic diseases and disorders, including diabetes.

Polynucleotide sequences encoding Mnk may also be used to monitor the progress of patients receiving treatment for pancreatic diseases and disorders, including diabetes. The polynucleotide sequences encoding Mnk may be used in Southern or Northern analysis, dot blot, or other membrane-based technologies; in PCR technologies; or in dip stick, pin, ELISA or chip assays utilizing fluids or tissues from patient biopsies to detect altered Mnk expression. Such qualitative or quantitative methods are well known in the art.

In a particular aspect, the nucleotide sequences encoding Mnk may be useful in assays that detect activation or induction of various metabolic diseases and disorders, including obesity, diabetes, eating disorders, wasting syndromes (cachexia), pancreatic dysfunctions, arteriosclerosis, coronary artery disease (CAD), disorders related to ROS production, and neurodegenerative diseases. The nucleotide sequences encoding Mnk may be labelled by standard methods, and added to a fluid or tissue sample from a patient under conditions suitable for the formation of hybridization complexes. After a suitable incubation period, the sample is washed and the signal is quantitated and compared with a standard value. The presence of altered levels of nucleotide sequences encoding Mnk in the sample compared to a control sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of Mnk, a normal or standard profile for expression is established. This may be accomplished by combining body fluids or cell extracts taken from normal subjects, either animal or human, with a sequence, or a fragment thereof, which encodes Mnk, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease. Once disease is established and a treatment protocol is initiated, hybridization assays may be repeated on a regular basis to evaluate whether the level of expression in the patient begins to approximate that, which is observed in the normal patient. The results obtained from successive assays may be used to show the efficacy of treatment over a period ranging from several days to months.

With respect to metabolic diseases and disorders, including obesity, diabetes, eating disorders, wasting syndromes (cachexia), pancreatic dysfunctions, arteriosclerosis, coronary artery disease (CAD), disorders related to ROS production, and neurodegenerative diseases presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the pancreatic diseases and disorders. Additional diagnostic uses for oligonucleotides designed from the sequences encoding Mnk may involve the use of PCR. Such oligomers may be chemically synthesized, generated enzymatically, or produced from a recombinant source. Oligomers will preferably consist of two nucleotide sequences, one with sense orientation (5'.fwdarw.3') and another with antisense (3'.rarw.5'), employed under optimized conditions for identification of a specific gene or condition. The same two oligomers, nested sets of oligomers, or even a degenerate pool of oligomers may be employed under less stringent conditions for detection and/or quantification of closely related DNA or RNA sequences.

Methods which may also be used to quantitate the expression of Mnk include radiolabelling or biotinylating nucleotides, coamplification of a control nucleic acid, and standard curves onto which the experimental results are interpolated (Melby, P. C. et al. (1993) J. Immunol. Methods, 159:235-244; Duplaa, C. et al. (1993) Anal. Biochem. 212:229-236). The speed of quantification of multiple samples may be accelerated by running the assay in an ELISA format where the oligomer of interest is presented in various dilutions and a spectrophotometric or colorimetric response gives rapid quantification.

In another embodiment of the invention, the nucleic acid Mnk sequences may also be used to generate hybridization probes, which are useful for mapping the naturally occurring genomic sequence. The sequences may be mapped to a particular chromosome or to a specific region of the chromosome using well known techniques. Such techniques include FISH, FAGS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7:127-134, and Trask, B. J. (1991) Trends Genet. 7:149-154. FISH (as described in Verma et al. (1988) Human Chromosomes: A Manual of Basic Techniques, Pergamon Press, New York, N.Y.) may be correlated with other physical chromosome mapping techniques and genetic map data. Examples of genetic map data can be found in the 1994 Genome Issue of Science (265:1981f). Correlation between the location of the gene encoding Mnk on a physical chromosomal map and a specific disease, or predisposition to a specific disease, may help to delimit the region of DNA associated with that genetic disease.

The nucleotide sequences of the subject invention may be used to detect differences in gene sequences between normal, carrier or affected individuals. In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti, R. A. et al. (1988) Nature 336:577-580), any sequences mapping to that area may represent associated or regulatory genes for further investigation. The nucleotide sequences of the subject invention may also be used to detect differences in the chromosomal location due to translocation, inversion, etc. among normal, carrier or affected individuals.

In another embodiment of the invention, the proteins of the invention, its catalytic or immunogenic fragments or oligopeptides thereof, an in vitro model, a genetically altered cell or animal, can be used for screening libraries of compounds in any of a variety of drug screening techniques. One can identify effectors, e.g. receptors, enzymes, proteins, peptides, ligands or substrates that bind to, modulate or mimic the action of one or more of the proteins of the invention. The protein or fragment thereof employed in such screening may be free in solution, affixed to a solid support, borne on a cell surface, or located intracellularly. The formation of binding complexes, between the proteins of the invention and the agent tested, may be measured. Agents could also, either directly or indirectly, influence the activity of the proteins of the invention. Target mechanisms can for example include a kinase activity, particularly the phosphorylation of proteins or peptides, most preferably, but not limited to serine and threonine residues. Another target mechanism could include the regulation of Mnk function by posttranslational modifications such as phosphorylation, dephosphorylation, acetylation, alkylation, ubiquitination, proteolytic processing subcellular localization or degradation. Yet another target mechanism could include the interaction of Mnk with protein binding partners such as, but not limited to, phospholipase A, estrogen receptors, kinases or translation factors. Of particular interest are screening assays for agents that have a low toxicity for mammalian cells. The term "agent" as used herein describes any molecule, e.g. protein or pharmaceutical, with the capability of altering or mimicking the physiological function of one or more of the proteins of the invention. Candidate agents encompass numerous chemical classes, though typically they are organic molecules, preferably small organic compounds having a molecular weight of more than 50 and less than about 2,500 Daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise carbocyclic or heterocyclic structures and/or aromatic or polyaromatic structures substituted with one or more of the above functional groups.

Candidate agents are also found among biomolecules including peptides, saccharides, fatty acids, steroids, purines, pyrimidines, nucleic acids and derivatives, structural analogs or combinations thereof. Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Where the screening assay is a binding assay, one or more of the molecules may be joined to a label, where the label can directly or indirectly provide a detectable signal.

Another technique for drug screening, which may be used, provides for high throughput screening of compounds having suitable binding affinity to the protein of interest as described in published PCT application W084/03564. In this method, as applied to the proteins of the invention large numbers of different small test compounds, e.g. aptamers, peptides, low-molecular weight compounds etc., are provided or synthesized on a solid substrate, such as plastic pins or some other surface. The test compounds are reacted with the proteins or fragments thereof, and washed. Bound proteins are then detected by methods well known in the art. Purified proteins can also be coated directly onto plates for use in the aforementioned drug screening techniques. Alternatively, non-neutralizing antibodies can be used to capture the peptide and immobilize it on a solid support. In another embodiment, one may use competitive drug screening assays in which neutralizing antibodies capable of binding the protein specifically compete with a test compound for binding the protein. In this manner, the antibodies can be used to detect the presence of any peptide, which shares one or more antigenic determinants with the protein.

Candidate agents may also be found in kinase assays where a kinase substrate such as a protein or a peptide, which may or may not include modifications as further described below, or others are phosphorylated by the proteins or protein fragments of the invention. A therapeutic candidate agent may be identified by its ability to increase or decrease the enzymatic activity of the proteins of the invention. The kinase activity may be detected by change of the chemical, physical or immunological properties of the substrate due to phosphorylation.

One example could be the transfer of radioisotopically labelled phosphate groups from an appropriate donor molecule to the kinase substrate catalyzed by the polypeptides of the invention. The phosphorylation of the substrate may be followed by detection of the substrates autoradiography with techniques well known in the art.

Yet in another example, the change of mass of the substrate due to its phosphorylation may be detected by mass spectrometry techniques.

One could also detect the phosphorylation status of a substrate with a reagent discriminating between the phosphorylated and unphosphorylated status of the substrate. Such a reagent may act by having different affinities for the phosphorylated and unphosphorylated forms of the substrate or by having specific affinity for phosphate groups. Such a reagent could be, but is not limited to, an antibody or antibody derivative, a recombinant antibody-like structure, a protein, a nucleic acid, a molecule containing a complexed metal ion, an anion exchange chromatography matrix, an affinity chromatography matrix or any other molecule with phosphorylation dependent selectivity towards the substrate.

Such a reagent could be employed to detect the kinase substrate, which is immobilized on a solid support during or after an enzymatic reaction. If the reagent is an antibody, its binding to the substrate could be detected by a variety of techniques as they are described in Harlow and Lane, 1998, Antibodies, CSH Lab Press, NY. If the reagent molecule is not an antibody, it may be detected by virtue of its chemical, physical or immunological properties, being endogenously associated with it or engineered to it.

Yet in another example the kinase substrate may have features, designed or endogenous, to facilitate its binding or detection in order to generate a signal that is suitable for the analysis of the substrates phosphorylation status. These features may be, but are not limited to, a biotin molecule or derivative thereof, a glutathione-S-transferase moiety, a moiety of six or more consecutive histidine residues, an amino acid sequence or hapten to function as an epitope tag, a fluorochrome, an enzyme or enzyme fragment. The kinase substrate may be linked to these or other features with a molecular spacer arm to avoid steric hindrance.

In one example the kinase substrate may be labelled with a fluorophore. The binding of the reagent to the labelled substrate in solution may be followed by the technique of fluorescence polarization as it is described in the literature (see, for example, Deshpande, S. et al. (1999) Prog. Biomed. Optics (SPIE) 3603:261; Parker, G. J. et al. (2000) J. Biomol. Screen. 5:77-88; Wu, P. et al. (1997) Anal. Biochem. 249:29-36). In a variation of this example, a fluorescent tracer molecule may compete with the substrate for the analyte to detect kinase activity by a technique which is known to those skilled in the art as indirect fluorescence polarization.

The nucleic acids encoding the proteins of the invention can be used to generate transgenic cell lines and animals. These transgenic animals are useful in the study of the function and regulation of the proteins of the invention in vivo. Transgenic animals, particularly mammalian transgenic animals, can serve as a model system for the investigation of many developmental and cellular processes common to humans. Transgenic animals may be made through homologous recombination in embryonic stem cells, where the normal locus of the gene encoding the protein of the invention is mutated. Alternatively, a nucleic acid construct encoding the protein is injected into oocytes and is randomly integrated into the genome. One may also express the genes of the invention or variants thereof in tissues where they are not normally expressed or at abnormal times of development. Furthermore, variants of the genes of the invention like specific constructs expressing anti-sense molecules or expression of dominant negative mutations, which will block or alter the expression of the proteins of the invention may be randomly integrated into the genome. A detectable marker, such as lac Z or luciferase may be introduced into the locus of the genes of the invention, where upregulation of expression of the genes of the invention will result in an easily detectable change in phenotype. Vectors for stable integration include plasmids, retroviruses and other animal viruses, yeast artificial chromosomes (YACs), and the like. DNA constructs for homologous recombination will contain at least portions of the genes of the invention with the desired genetic modification, and will include regions of homology to the target locus. Conveniently, markers for positive and negative selection are included. DNA constructs for random integration do not need to contain regions of homology to mediate recombination. DNA constructs for random integration will consist of the nucleic acids encoding the proteins of the invention, a regulatory element (promoter), an intron and a poly-adenylation signal. Methods for generating cells having targeted gene modifications through homologous recombination are known in the field. For embryonic stem (ES) cells, an ES cell line may be employed, or embryonic cells may be obtained freshly from a host, e.g. mouse, rat, guinea pig, etc. Such cells are grown on an appropriate fibroblast-feeder layer and are grown in the presence of leukemia inhibiting factor (LIF). ES or embryonic cells may be transfected and can then be used to produce transgenic animals. After transfection, the ES cells are plated onto a feeder layer in an appropriate medium. Cells containing the construct may be selected by employing a selection medium. After sufficient time for colonies to grow, they are picked and analyzed for the occurrence of homologous recombination. Colonies that are positive may then be used for embryo manipulation and morula aggregation. Briefly, morulae are obtained from 4 to 6 week old superovulated females, the Zona Pellucida is removed and the morulae are put into small depressions of a tissue culture dish. The ES cells are trypsinized, and the modified cells are placed into the depression closely to the morulae. On the following day the aggregates are transferred into the uterine horns of pseudopregnant females. Females are then allowed to go to term. Chimeric offsprings can be readily detected by a change in coat color and are subsequently screened for the transmission of the mutation into the next generation (F1-generation). Offspring of the F1-generation are screened for the presence of the modified gene and males and females having the modification are mated to produce homozygous progeny. If the gene alterations cause lethality at some point in development, tissues or organs can be maintained as allogenic or congenic grafts or transplants, or in vitro culture. The transgenic 3o animals may be any non-human mammal, such as laboratory animal, domestic animals, etc., for example, mouse, rat, guinea pig, sheep, cow, pig, and others. The transgenic animals may be used in functional studies, drug screening, and other applications and are useful in the study of the function and regulation of the proteins of the invention in vivo.

Finally, the invention also relates to a kit comprising at least one of
(a) a Mnk2 (Mnk2a or Mnk2b) or Mnk1 nucleic acid molecule or a fragment thereof;
(b) a vector comprising the nucleic acid of (a);
(c) a host cell comprising the nucleic acid of (a) or the vector of (b);
(d) a polypeptide encoded by the nucleic acid of (a);
(e) a fusion polypeptide encoded by the nucleic acid of (a);
(f) an antibody, an aptamer or another receptor against the nucleic acid of (a) or the polypeptide of (d) or (e) and
(g) an anti-sense oligonucleotide of the nucleic acid of (a).

The kit may be used for diagnostic or therapeutic purposes or for screening applications as described above. The kit may further contain user instructions.

The Examples illustrate the invention:

Example 1

Measurement of Triglyceride Content of Homozygous Flies (FIG. 1)

The change of triglyceride content of *Drosophila melanogaster* containing a special expression system (EP-element, Rorth P, Proc Natl Acad Sci USA 1996, 93(22): 12418-22) was measured. Mutant flies are obtained from a fly mutation stock collection. The flies are grown under standard conditions known to those skilled in the art, and in the course of the experiment, additional feedings with bakers yeast (*Saccharomyces cerevisiae*) are provided. Specifically, homozygous male EP(3)3333 and EP(3)3576 flies were investigated in comparison to control flies (FIG. 1). For determination of triglyceride content, flies were incubated for 5 min at gooc in an aqueous buffer using a waterbath, followed by hot extraction. After another 5 min incubation at 90° C. and mild centrifugation, the triglyceride content of the flies extract was determined using Sigma Triglyceride (I NT 336-10 or -20) assay by measuring changes in the optical density according to the manufacturer's protocol. As a reference protein content of the same extract was measured using BIO-RAD DC Protein Assay according to the manufacturer's protocol. The assay was repeated several times. The average triglyceride level of EP collection is shown as 100% in FIG. 1. EP(3)3333 and EP(3)3576 homozygous flies show constantly a higher triglyceride content than the controls (approx. 140%). Therefore, the change of gene activity in the locus 86F7 (estimated), where the EP-vector of EP(3)3333 and EP(3)3576 flies is homozygous viably integrated into the Lk6 gene locus, is responsible for changes in the metabolism of the energy storage triglycerides, therefore representing in both cases an obese fly model.

Example 2

Identification of the *Drosophila* Gene Responsible for the Change in the Metabolism of the Energy Storage Triglycerides (FIG. 2)

Genomic DNA sequences were isolated that are localized directly adjacent to the integration of the EP vectors (herein EP(3)3333 and EP(3)3576). Using those isolated genomic sequences, public databases like Berkeley *Drosophila* Genome Project (Gad Fly) were screened thereby confirming the homozygous viable integration site of the EP(3)3333 and EP(3)3576 vectors. FIG. 2 shows the molecular organization of this gene locus. In FIG. 2, genomic DNA sequence is represented by the assembly as a dotted black line (from position 7544500 to 7559500 on chromosome 3R) that includes the integration sites of EP(3)3333 and EP(3)3576. Transcribed DNA sequences (expressed sequence tags, ESTs) and predicted exons are shown as bars in the lower two lines. Predicted exons of gene CG17342 (Gad Fly, Lk6, homologous to Mnk) are shown as dark grey bars and introns are shown as slim grey lines in the middle of the figure. Using plasmid rescue method genomic DNA sequences that are directly localised 3' of the EP(3)3333 and EP(3)3576 integration site were isolated. Using the plasmid rescue DNA public DNA sequence databases were screened thereby identifying the integration site of EP(3)3333 and EP(3)3576 causing an increase of triglyceride content. EP(3)3333 is integrated in the 5' region of a 5 prime exon of the gene CG17342 and EP(3)3576 in the 5' region of an alternative 5' exon. Mnk encodes for a gene that is predicted by GadFly sequence analysis programs as CG17342. Therefore, expression of the CG17342 could be affected by homozygous viable integration of the EP(3)3333 and EP(3)3576 leading to increase of the energy storage triglycerides and a change of uncoupling protein activity.

Example 3

Cloning of a *Drosophila melanogaster* Gene with Homology to Human Uncoupling Proteins (UCPs) (FIG. 7)

Sequences homologous to human UCP2 and UCP3 genes were identified using the publicly available program BLAST of the data base of the National Center for Biotechnology Information (NCBI) (see, Altschul et al., 1997, Nucleic Acids Res. 25:3389-3402). The homology search yielded sequence fragments of a family of *Drosophila* genes with UCP homology. They are clearly different to the next related mitochondrial proteins (oxoglutarate carrier). Using the sequence fragment of one of this genes (herein referred to as dUCPy'), a PCR primer pair was generated (Upper 5'-CTAAACAAA-CAATTCCAAACATAG (SEQ ID NO.: 9), Lower 5 prime-AAAAGACATAGAAAATACGATAGT (SEQ ID NO.: 10)) and a PCR reaction performed on *Drosophila* cDNA using standard PCR conditions. The amplification product was radioactively labelled and used to screen a cDNA library prepared from adult *Drosophila* flies (Stratagene). A full-length cDNA clone was isolated, sequenced (FIG. 7), and used for further experiments. The nucleotide sequence of dUCPy is shown in FIG. 7A (SEQ ID NO.: 7), the deduced open reading is shown in FIG. 7B (SEQ ID NO.: 8).

Example 4

Cloning of the dUCPy cDNA into an *Drosophila* Expression Vector

In order to test the effects of dUCPy expression in *Drosophila* cells, the dUCPy cDNA was cloned into the expression vector pUAST (Brand A & Perrimon N, Development 1993, 118:401-415) using the restriction sites Not I and Kpn I. The resulting expression construct was injected into the germline of *Drosophila* embryos and *Drosophila* strains with a stable integration of the construct were generated. Since the expression vector pUAST is activated by the yeast transcription factor Gal4 which is normally absent from *Drosophila* cells dUCPy is not yet expressed in these transgenic animals. If pUAST-dUCPy flies are crossed with a second *Drosophila* strain that expresses Gal4 in a tissue specific manner the offspring flies of this mating will express dUCPy in the Gal4 expressing tissue. The cross of pUAST-dUCPy flies with a strain that expresses Gal4 in all cells of the body (under control of the actin promoter) showed no viable offspring. This means that dUCPy overexpression in all body cells is lethal. This finding is consistent with the assumption that dUCPy overexpression could lead to a collapse of the cellular energy production. Expression of dUCPy in a non-vital organ like the eye (Gal4 under control of the eye-specific promoter of the "eyeless" gene) results in flies with visibly damaged eyes. This easily visible eye phenotype is the basis of a genetic screen for gene products that can modify UCP activity.

Figure 4:
FIG. 4 shows the eye phenotype induced by over-expression of the *Drosophila* UCP uncoupling protein homologue (dUCPy) that was used to discover factors modulating uncoupling protein activity. In the fly shown in the left part of the picture, dUCPy is expressed at normal levels. In the fly shown in the right part of the photograph, dUCPy is over-expressed, and the eye is reduced.

Example 5 dUCPy Modifier Screen (FIG. 4)

Parts of the genomes of the strain with Gal4 expression in the eye and the strain carrying the pUAST-dUCPy construct were combined on one chromosome using genomic recombination. The resulting fly strain has eyes that are permanently damaged by dUCPy expression. Flies of this strain were crossed with flies of a large collection of mutagenized fly strains. In this mutant collection a special expression system (EP-element, see Rorth, 1996, supra) is integrated randomly in different genomic loci. The yeast transcription factor Gal4 can bind to the EP-element and activate the transcription of endogenous genes close the integration site of the EP-element. The activation of the genes therefore occurs in the same cells (eye) that overexpress dUCPy. Since the mutant collection contains several thousand strains with different integration sites of the EP-element it is possible to test a large number of genes whether their expression interacts with dUCPy activity. In case a gene acts as an enhancer of UCP activity the eye defect will be worsened; a suppressor will ameliorate the defect (see FIG. 4). Using this screen a gene with enhancing activity was discovered that was found to be the LK6 kinase in *Drosophila*.

Example 6

Cloning of Lk6 from *Drosophila* (FIG. 3A)

Genomic DNA neighbouring to the eye-defect rescuing EP-element was cloned by inverse PCR and sequenced. This sequence was used for a BLAST search in a public *Drosophila* gene database. The amino acid sequence (SEQ ID NO.: 40) of the *Drosophila* protein is shown in FIG. 3A (referred to as dmAB18789).

Example 7

Identification of Mammalian LK6 Homologous Proteins (FIG. 3)

Sequences homologous to *Drosophila* Lk6 were identified using the publicly available program BLASTP 2.2.3 of the non-redundant protein data base of the National Center for Biotechnology Information (NCBI) (see, Altschul et al., 1997, Nucleic Acids Res. 25:3389-3402). Mnk homologous proteins and nucleic acid molecules coding therefore are obtainable from insect or vertebrate species, e.g. mammals or birds. Particularly preferred are human Mnk homologous polypeptides and nucleic acids, particularly polypeptides and nucleic acids encoding a human Mnk2 protein (Genbank Accession No. AF237775 (SEQ ID NO.: 2) and NM_017572.1 (SEQ ID NO.: 4); Genbank Accession No. AF237775 (SEQ ID NO.: 2) is identical to formerly Genbank Accession No. XM_030637 which was removed at the submitters request; see a Clustal W multiple sequence alignment in FIG. 3B) or nucleic acids encoding a human Mnk1 protein (Genbank Accession No. AB000409.1 (SEQ ID NO.: 56) and NM_003684.2 (SEQ ID NO.: 59); Genbank Accession No. AB000409.1 (SEQ ID NO.: 56) is identical to formerly Genbank Accession No. XM_001600 which was removed at the submitters request; see a Clustal W multiple sequence alignment in FIG. 3C). FIG. 3A shows the alignment of the Mnk proteins from different species, hXP_030637 refers to human Mnk2 (identical to Genbank Accession No. AF237775 (SEQ ID NO.: 2)), hXP_001600 refers to human Mnk1 (identical to Genbank Accession No. AB000409.1 (SEQ ID NO.: 56)), and dmAB18789 refers to the protein having amino acid sequence SEQ ID NO.: 40 encoded by *Drosophila* gene with GadFly Accession No. CG17342. The mouse homologous polypeptides of the invention were identified as GenBank Accession Numbers NP_067437.1 (SEQ ID NO.: 85) (for the mouse homolog MAP kinase-interacting serine/threonine kinase 2; Mnk2; encoded by the cDNA having GenBank Accession Number BC010256 (SEQ ID NO.: 57)) and GenBank Accession Number NP_067436.1 (SEQ ID NO.: 86) (for the mouse homolog MAP kinase-interacting serine/threonine kinase 1; Mnk1).

Example 8

Expression of the Polypeptides in Mammalian (Mouse) Tissues (FIG. 5 and FIG. 6)

For analyzing the expression of the polypeptides disclosed in this invention in mammalian tissues, several mouse strains (preferably mice strains C57B1/6J, C57B1/6 ob/ob and C57B1/KS db/db which are standard model systems in obesity and diabetes research) were purchased from Harlan Winkelmann (33178 Borchen, Germany) and maintained under constant temperature (preferably 22° C.), 40 percent humidity and a light/dark cycle of preferably 14/10 hours. The mice were fed a standard chow (for example, from ssniff Spezialitaten GmbH, order number ssniff M-Z V1126-000). For the fasting experiment ("fasted wild type mice"), wild type mice were starved for 48 h without food, but only water supplied ad libitum. (see, for example, Schnetzler et al. J Clin Invest 1993 July; 92(1):272-80, Mizuno et al. Proc Natl Acad Sci USA 1996 Apr. 16; 93(8):3434-8). Animals were sacrificed at an age of 6 to 8 weeks. The animal tissues were isolated according to standard procedures known to those skilled in the art, snap frozen in liquid nitrogen and stored at −80° C. until needed. For analyzing the role of the proteins disclosed in this invention in the in vitro differentiation of different mammalian cell culture cells for the conversion of pre-adipocytes to adipocytes, mammalian fibroblast (3T3-L1) cells (e.g., Green & Kehinde, Cell 1: 113-116, 1974) were obtained from the American Tissue Culture Collection (ATCC, Hanassas, Va., USA; ATCC-CL 173). 3T3-L1 cells were maintained as fibroblasts and differentiated into adipocytes as described in the prior art (e.g., Qiu. et al., J. Biol. Chem. 276:11988-95, 2001; Slieker et al., BBRC 251: 225-9, 1998). In brief, cells were plated in DMEM/10% FCS (Invitrogen, Karlsruhe, Germany) at 50,000 cells/well in duplicates in 6-well plastic dishes and cultured in a humidified atmosphere of 5% $CO_2$ at 37° C. At confluence (defined as day 0: d0) cells were transferred to serum-free (SF) medium, containing DMEM/HamF12 (3:1; Invitrogen), Fetuin (300 μg/ml; Sigma, Munich, Germany), Transferrin (2 μg/ml; Sigma), Pantothenate (17 μM; Sigma), Biotin (1 $_m$M; Sigma), and EGF (0.8 nM; Hoffmann-La Roche, Basel, Switzerland). Differentiation was induced by adding Dexamethasone (DEX; 1 μM; Sigma), 3-Methyl-Isobutyl-1-Methylxanthine (MIX; 0.5 mM; Sigma), and bovine Insulin (5 μg/ml; Invitrogen). Four days after confluence (d4), cells were kept in SF medium, containing bovine Insulin (5 μg/ml) until differentiation was completed. At various time points of the differentiation procedure, beginning with day 0 (day of confluence) and day 2 (hormone addition; for example, dexamethason and 3-isobutyl-1-methylxanthin), up to 10 days of differentiation, suitable aliquots of cells were taken every two days. Alternatively, mammalian fibroblast 3T3-F442A cells (e.g., Green & Kehinde, Cell 7: 105-113, 1976) were obtained from the Harvard Medical School, Department of Cell Biology (Boston, Mass., USA). 3T3-F442A cells were maintained as fibroblasts and differentiated into adipocytes as described previously (Djian, P. et al., J. Cell. Physiol., 124:554-556, 1985). At various time points of the differentiation procedure, beginning with day 0 (day of confluence and hormone addition, for example, Insulin), up to 10 days of differentiation, suitable aliquots of cells were taken every two days. 3T3-F442A cells are differentiating in vitro already in the confluent stage after hormone (insulin) addition. TaqMan Analysis of the proteins of the invention was carried out (FIG. 5 and FIG. 6). RNA was isolated from mouse tissues or cell culture cells using Trizol Reagent (for example, from Invitrogen, Karlsruhe, Germany) and further purified with the RNeasy Kit (for example, from Qiagen, Germany) in combination with an DNase-treatment according to the instructions of the manufacturers and as known to those skilled in the art. Total RNA was reverse transcribed (preferably using Superscript II RNaseH-Reverse Transcriptase, from Invitrogen, Karlsruhe, Germany) and subjected to Taqman analysis preferably using the Taqman 2×PCR Master Mix (from Applied Biosystems, Weiterstadt, Germany; the Mix contains according to the Manufacturer for example AmpliTaq Gold DNA Polymerase, AmpErase UNG, dNTPs with dUTP, passive reference Rox and optimized buffer components) on a GeneAmp 5700 Sequence Detection System (from Applied Biosystems, Weiterstadt, Germany).

For the analysis of the expression of Mnk2 or Mnk1, taqman analysis was performed using the following primer/probe pairs:

```
Mouse Mnk1 forward primer (Seq ID NO: 11)
5'-GCT GAG GGC CTC TGC TCC-3';

Mouse Mnk1 reverse primer (Seq ID NO: 12)
5'-TCG CCT TCG AGC GAG G-3';

Mouse Mnk1 Taqman probe (Seq ID NO: 13)
(5/6-FAM) TGAAGCTGTCCCCTCCATCCAAATCTC (5/6-TAMRA)
```

```
-continued
Taqman-1856F Mnk2 forward primer (SEQ ID NO: 14):
5'-TGCACTTGATTGACCCCGA-3'

Taqman-1923R Mnk2 reverse primer (SEQ ID NO: 15):
5'-TTTCTGATTGTCAACCCTCCAA-3'

Taqman-1877T Mnk2 Taqman probe (SEQ ID NO: 16):
(5/6-FAM)-CCCCATCATCCACCTGCAGTGTCC-(5/6-TAMRA)
```

Figure 5A:
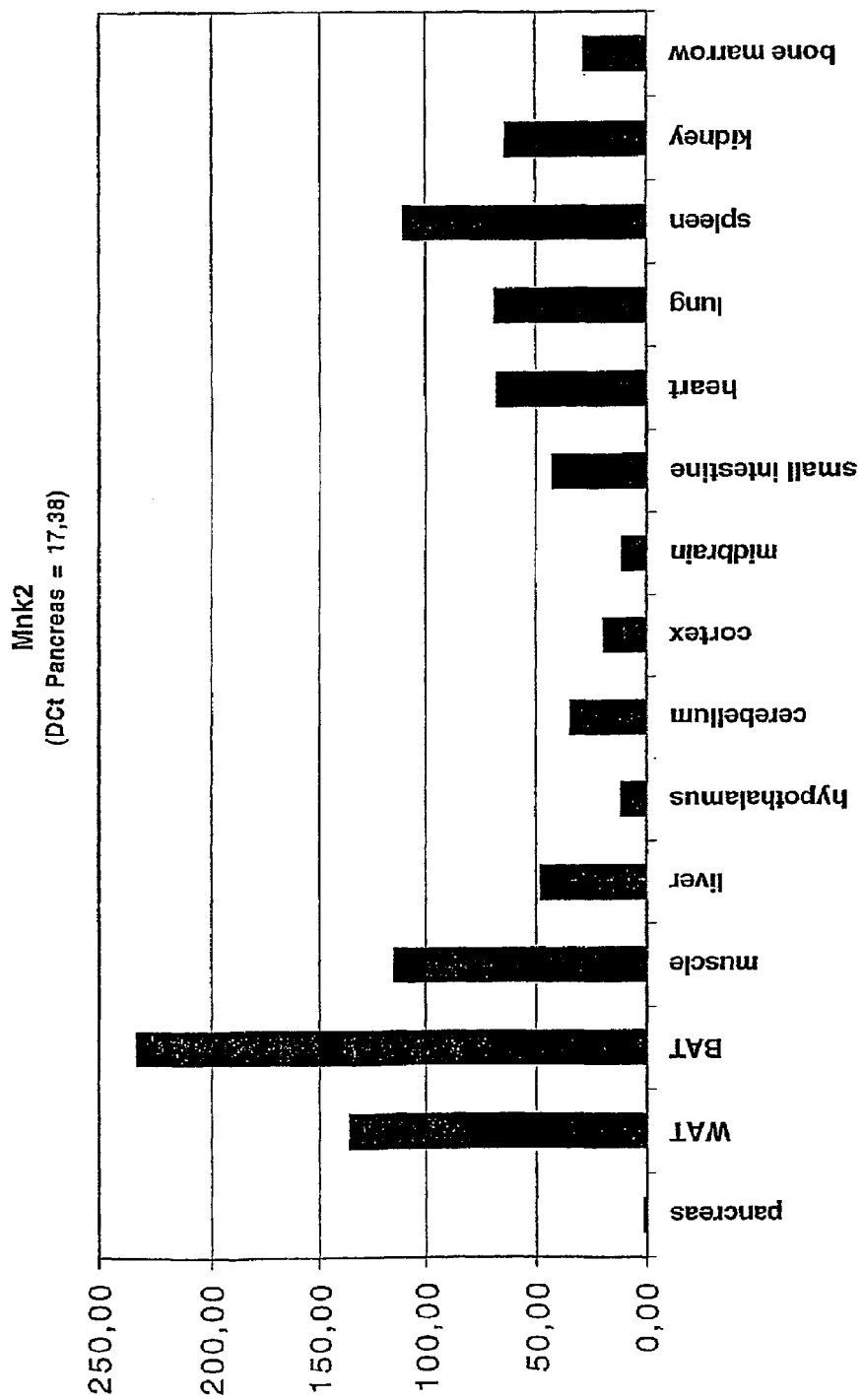
FIGS. 5A and 5B show the expression of the Mnk2 gene.
Figure 5B:
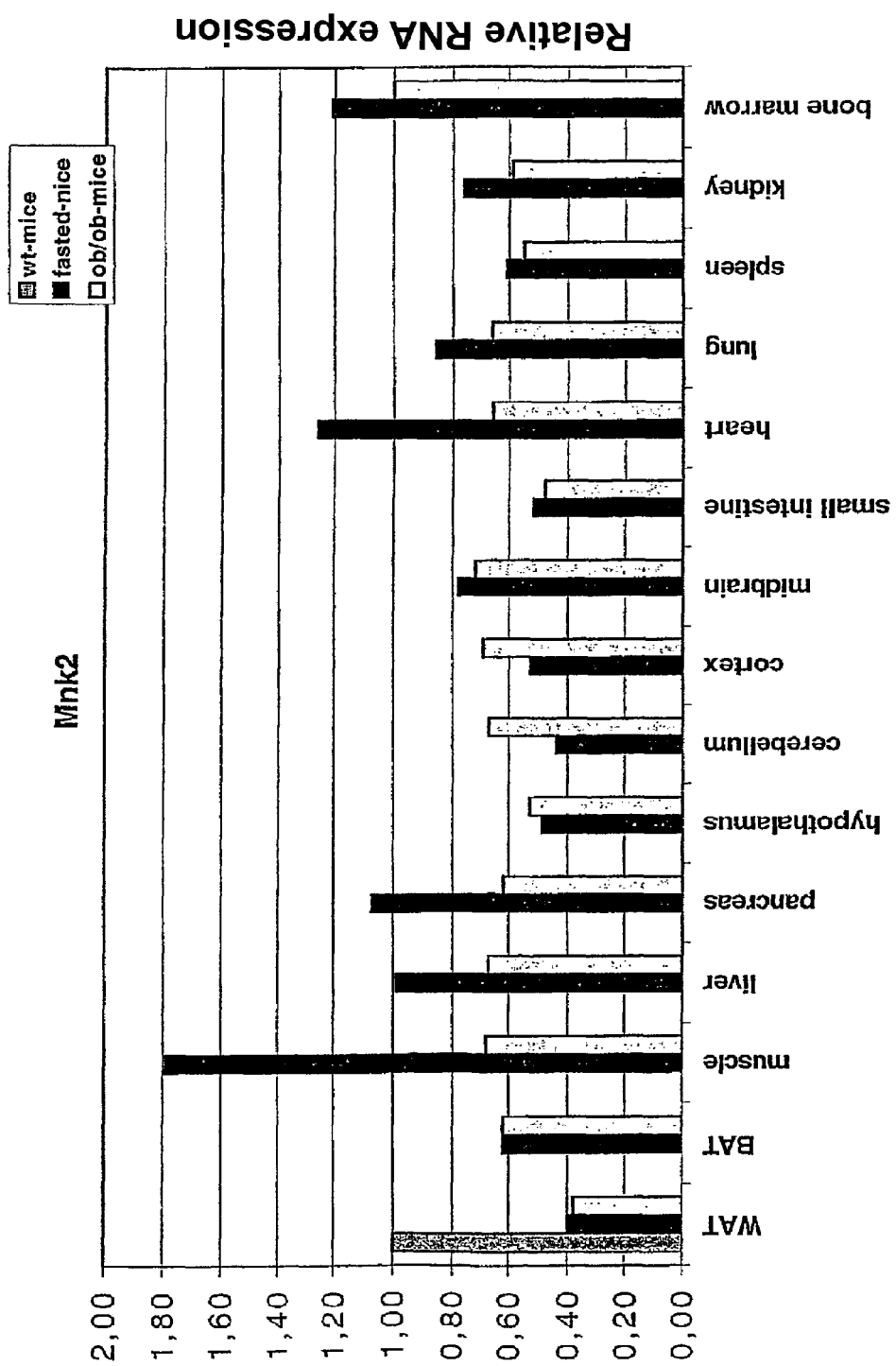
Figure 5C:
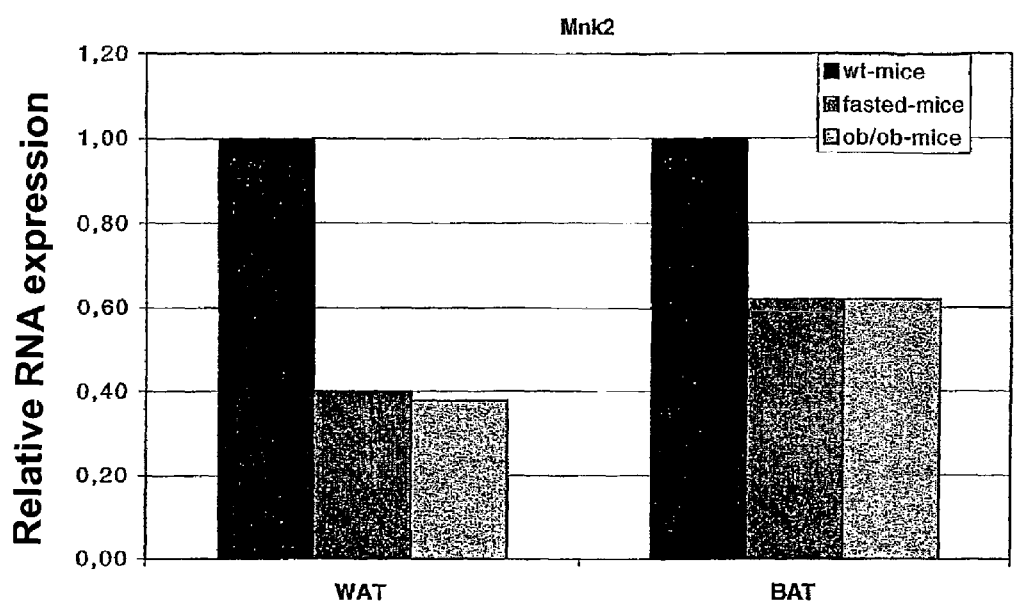
FIG. 5C shows the expression of mouse Mnk2 gene in adipose tissue of fasted and obese mice strains.
Figure 5D:
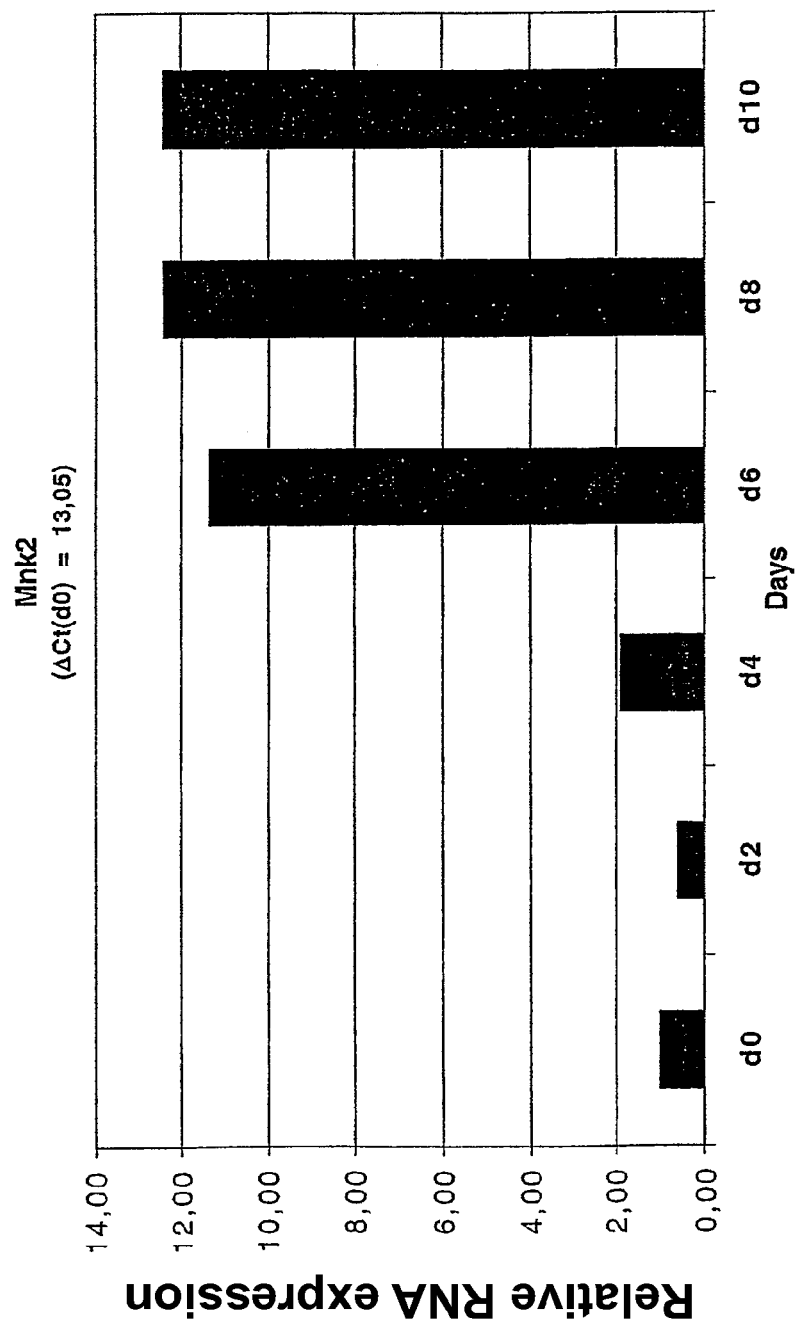
FIG. 5D shows the real-time PCR mediated comparison of Mnk2 expression during differentiation of mammalian fibroblast (3T3-L1) cells from pre-adipocytes to mature adipocytes.
Figure 5E:
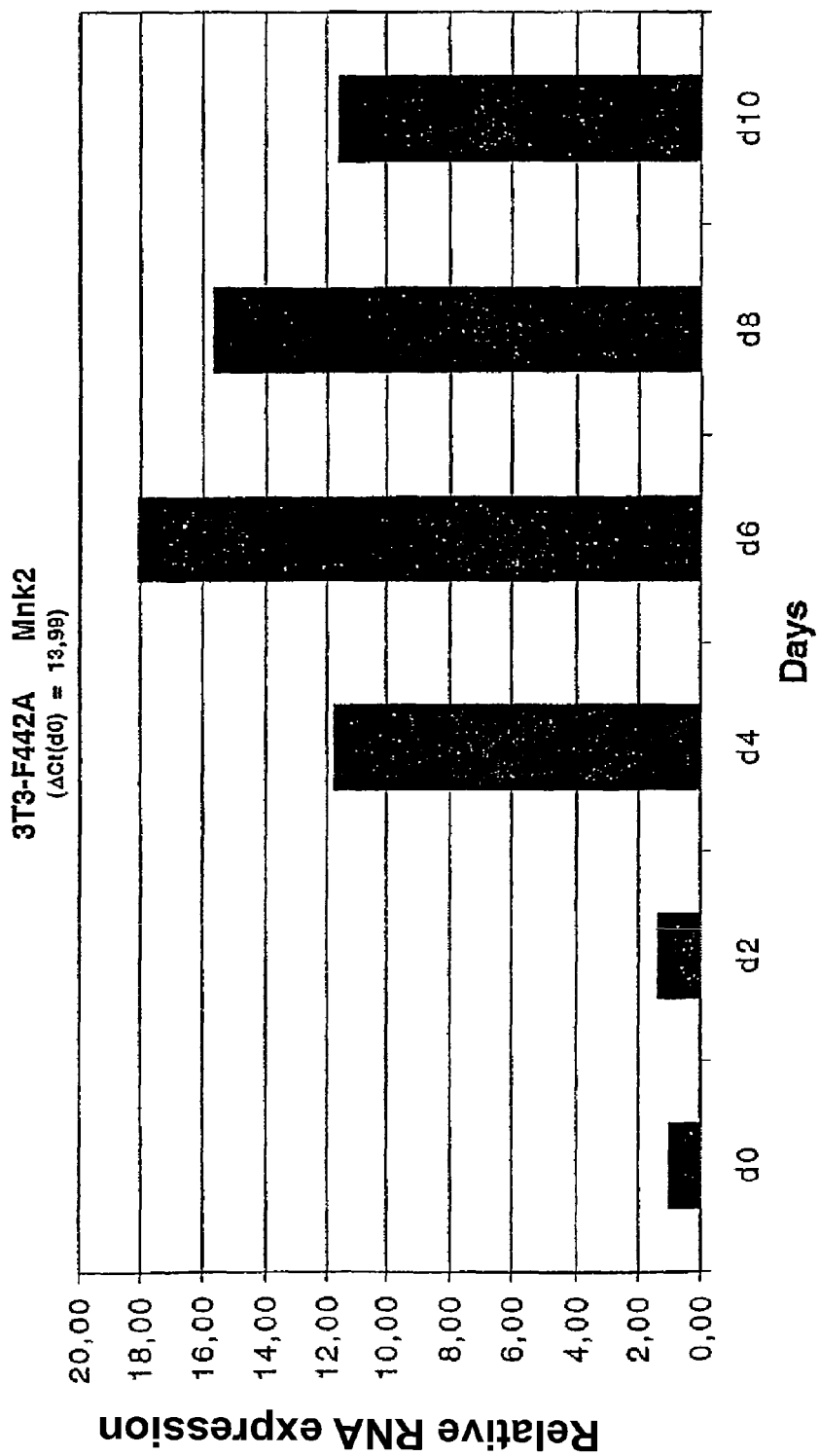
FIG. 5E shows real-time PCR mediated comparison of Mnk2 expression during the differentiation of mammalian fibroblast 3T3-F442A cells from preadipocytes to mature adipocytes.
Figure 5F:
FIG. 5F shows real-time PCR mediated comparison of Mnk2 expression during the differentiation of mammalian fibroblast TA1 cells from preadipocytes to mature adipocytes.
Figure 6A:
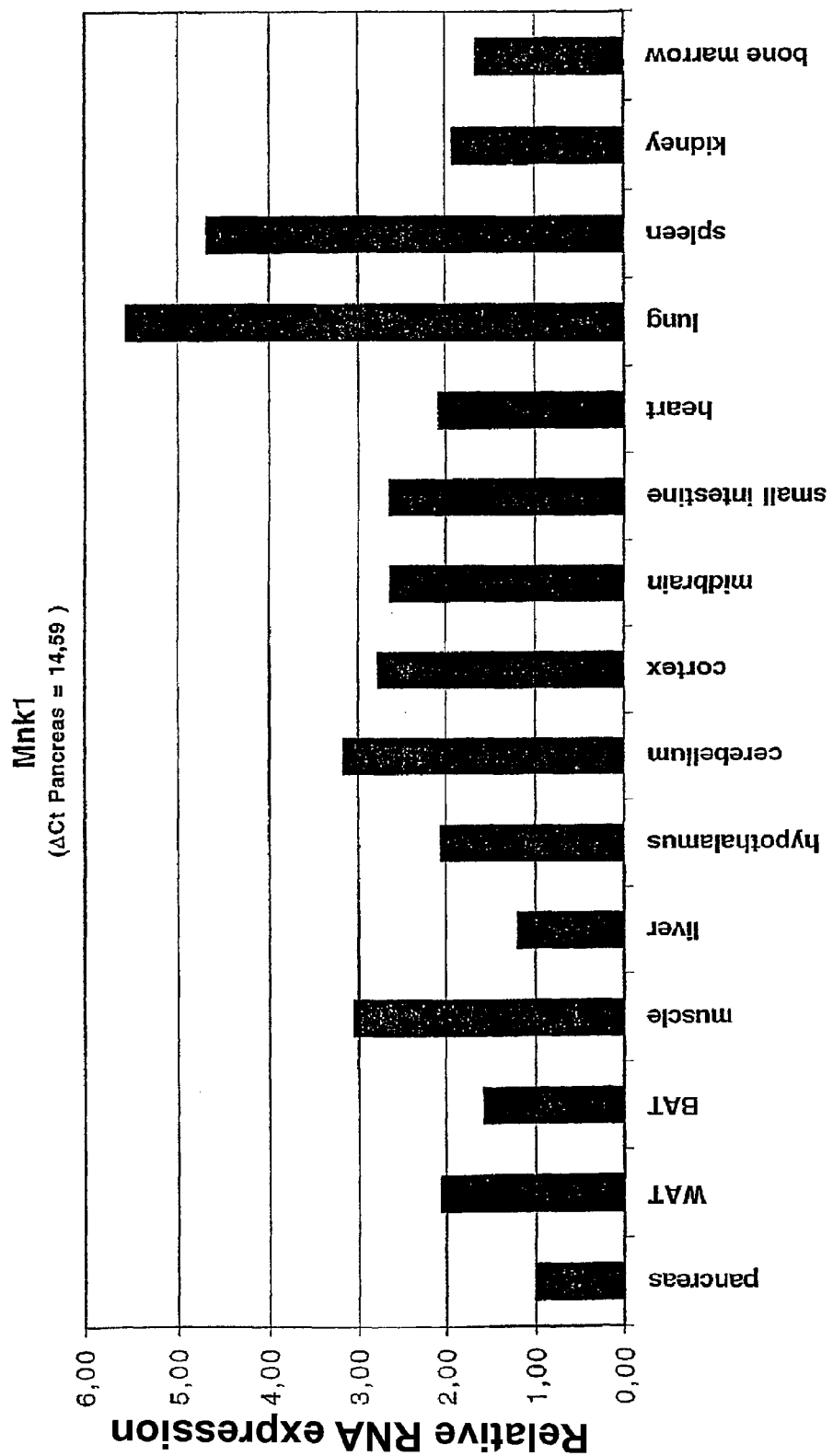
FIGS. 6A and 6B show the expression of the mouse Mnk1 gene in different wild-type mouse tissues.
Figure 6B:
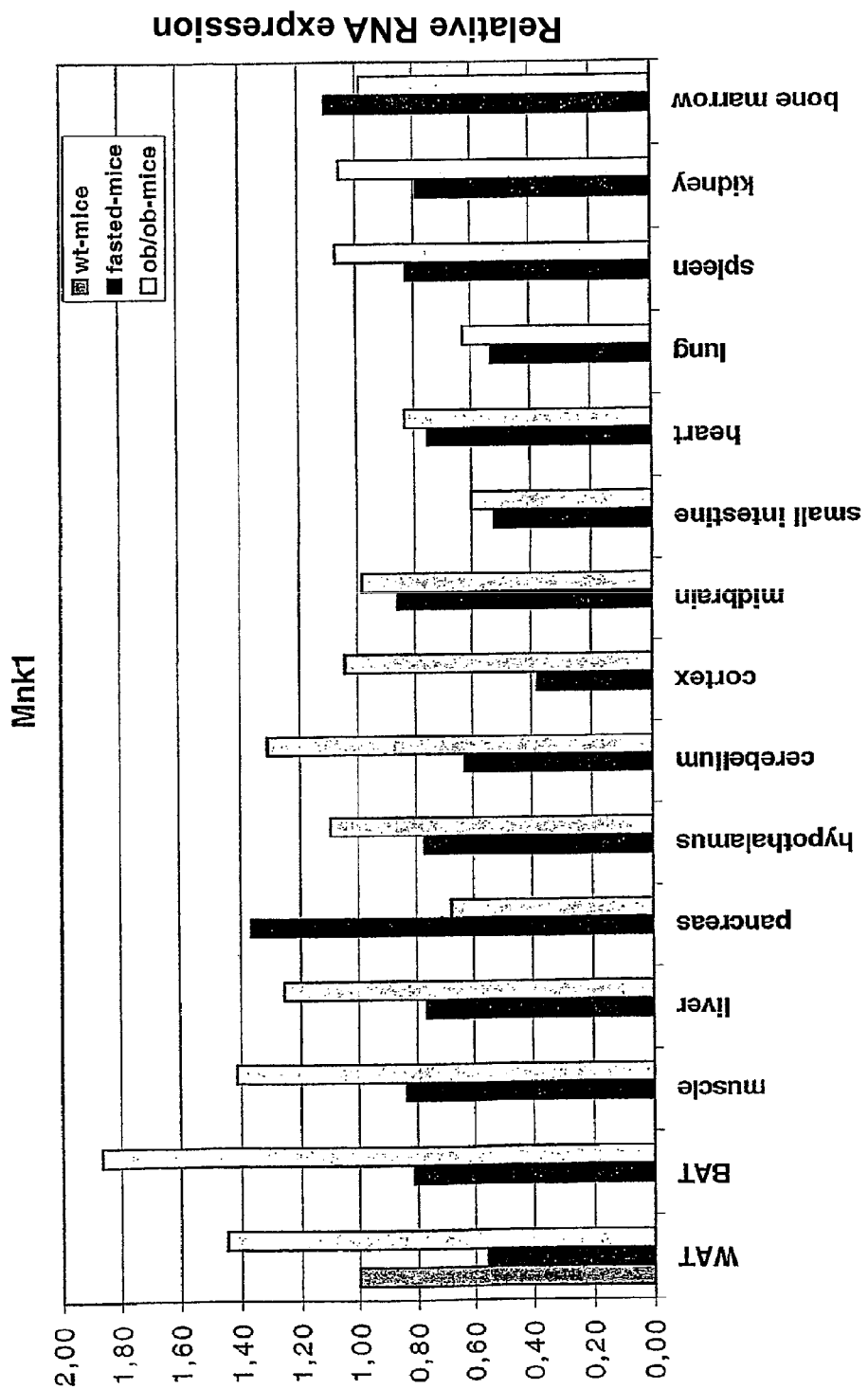
Figure 6C:
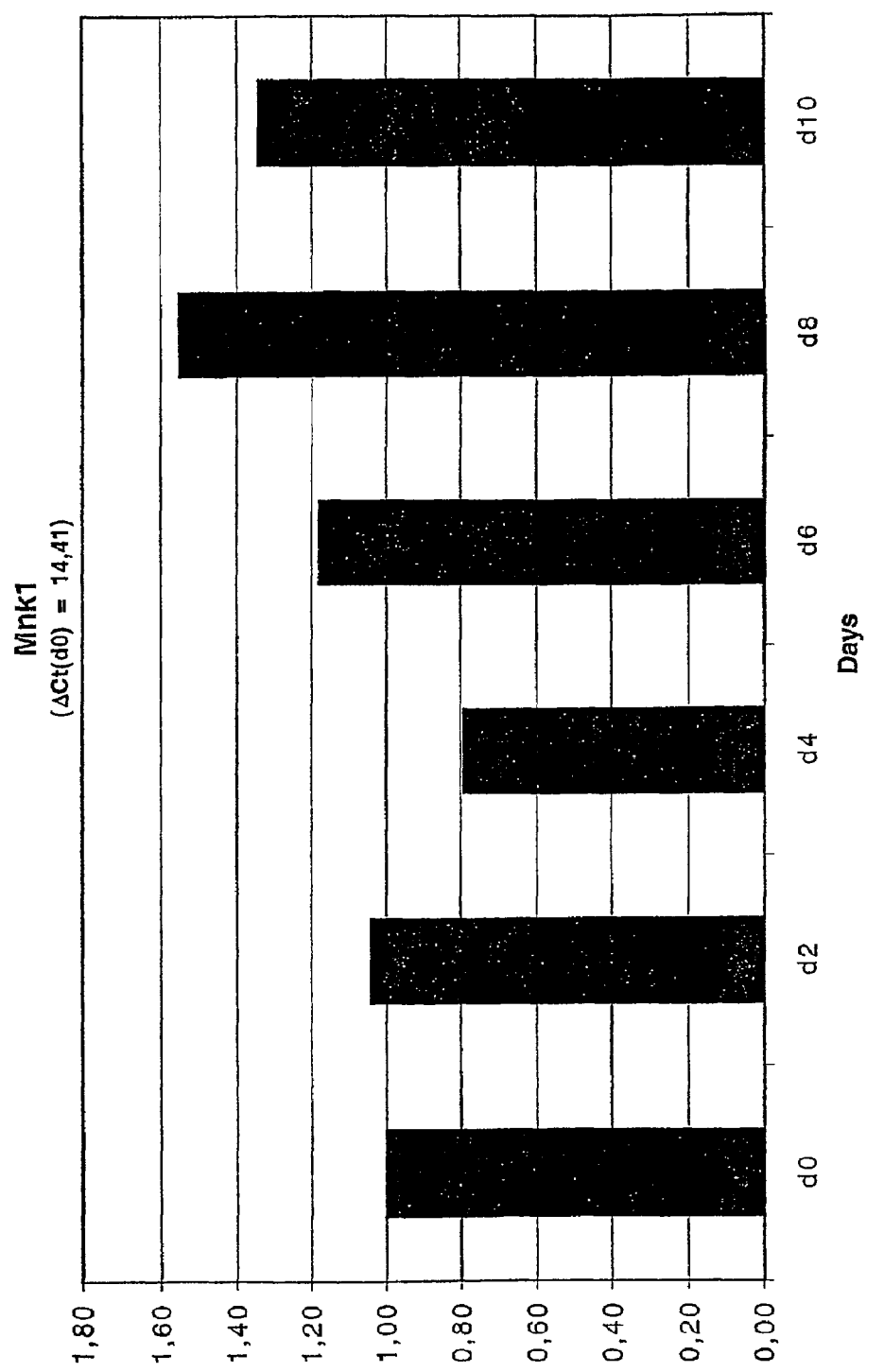
FIG. 6C shows the real-time PCR mediated comparison of Mnk1 expression during differentiation of cultured mammalian fibroblast 3T3-L1 cells from pre-adipocytes to mature adipocytes.
Figure 6D:
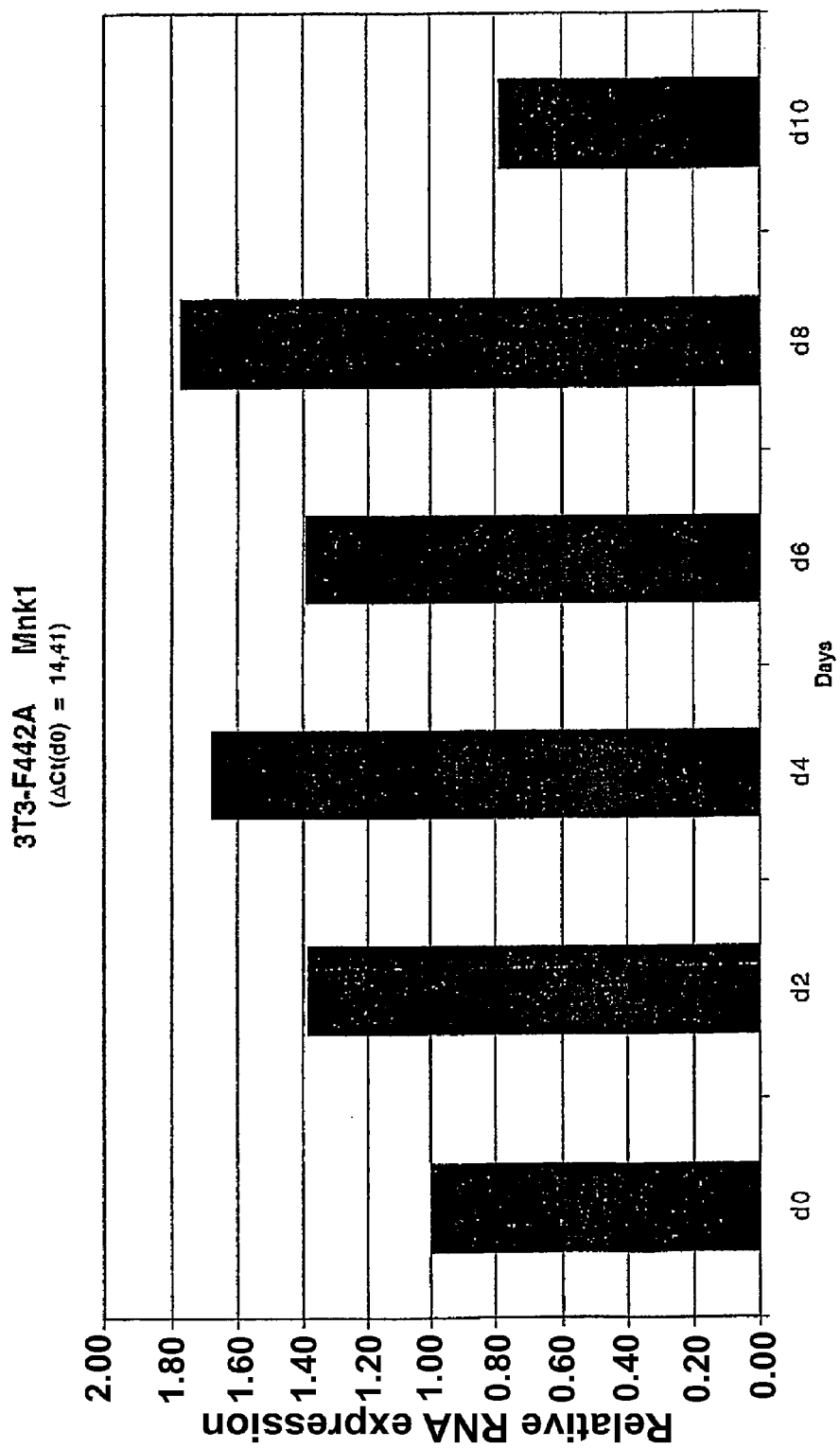
FIG. 6D shows real-time PCR mediated comparison of Mnk1 expression during the differentiation of cultured mammalian fibroblast 3T3-F442A cells from preadipocytes to mature adipocytes.
Figure 6E:
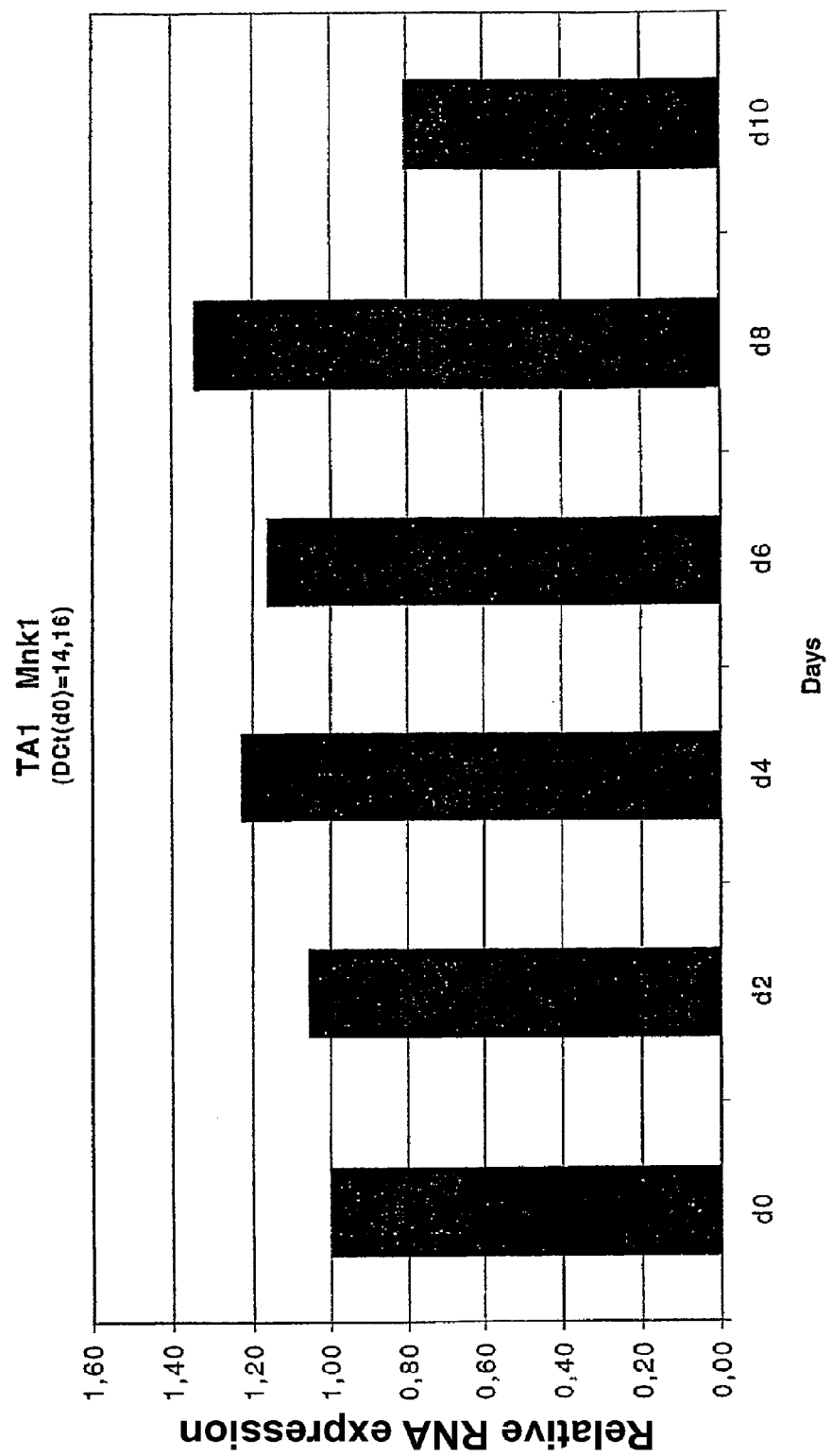
FIG. 6E shows real-time PCR mediated comparison of Mnk1 expression during the differentiation of mammalian fibroblast TA1 cells from preadipocytes to mature adipocytes.

Taqman analysis revealed that Mnk2 is the more interesting homologue of the fly Lk6 gene. The results are shown in FIG. 5 and FIG. 6. In comparison to Mnk1, which is rather ubiquitously expressed, Mnk2 shows its highest expression levels in the brown and white adipose tissues (FIGS. 5A and 6A, respectively). The expression of Mnk2 in white adipose tissue is under metabolic control: In fasted as well as obese (ob/ob) mice, expression is reduced to about 40% of wildtype levels (FIG. 5C; see also FIG. 5B). In addition, expression of Mnk2 is strongly induced during the in vitro differentiation of 3T3-L 1 (FIG. 5D) as well as of two additional model systems for the in vitro differentiation of preadipocytes to adipocytes, the 3T3-F442A and TA1 cell lines (FIG. 5E and FIG. 5F, respectively). Contrary to this, the relative expression levels of Mnk1 remain unchanged during the differentiation of these cell lines (FIGS. 6D and 6E, respectively).

Example 9

Expression of the Polypeptides in Mammalian (Human) Tissues (FIG. 9)

Human primary adipocytes were differentiated into mature adipocytes as described by Hauner et al. 1989 (J Clin Invest 84(5): 1663-70). Briefly, cells were grown in DMEM/Nutrient Mix F12, 1% PenStrep, 17 μM Biotin, 33 μM Pantothenat, 10% none heat inactivated fetal calf serum. On day 0 of differentiation, the medium was changed to OM EM/Nutrient Mix F12, 1% Pen/Strep, 17 μM Biotin, 33 μM Pantothenat, 0.01 mg/ml Transferrin, Hydrocortisone, 20 nM humanes Insulin, 0.2 nM T3, 25 nM Dexamethasone, 250 μIM IBMX, 3 μM Rosiglitazone. On day 4 of differentiation, the medium was changed to DMEM/Nutrient Mix F12 1% Pen/Strep, 17 μM Biotin, 33 μM Pantothenat, 0.01 mg/ml Transferrin, 100 nM Hydrocortisone, 20 nM humanes Insulin, 0.2 nM T3. At various time points of the differentiation procedure, beginning with day 0 (day of confluence) and day 4 (hormone addition), up to 14 days of differentiation, suitable aliquots of cells were taken every two days. RNA was isolated from human cell culture cells using Trizol Reagent (for example, from Invitrogen, Karlsruhe, Germany) and further purified with the RNeasy Kit (for example, from Qiagen, Germany) in combination with an DNase-treatment according to the instructions of the manufacturers and as known to those skilled in the art. In addition to the RNA isolated from human adipocytes at different differentiation stage, RNAs isolated from different human tissues were obtained from Invitrogen Corp., Karlsruhe, Germany: (i) total RNA from human adult skeletal muscle (Invitrogen Corp. Order Number 735030); (ii) total RNA from human adult lung (Invitrogen Corp. Order Number 735020); (iii) total RNA from human adult liver (Invitrogen Corp. Order Number 735018); (iv) total RNA from human adult placenta (Invitrogen Corp. Order Number 735026); (v) total RNA from human adult testis (Invitrogen Corp. Order Number 641 01-1); (vi) total RNA from human normal adipose tissue (Invitrogen Corp. Order Number 06005-01); (vii) total RNA from human normal pancreas (Invitrogen Corp. Order Number DG61 01); (viii) total RNA from human normal brain (Invitrogen Corp. Order Number 06030-01). The RNA was treated with DNase according to the instructions of the manufacturers (for example, from Qiagen, Germany) and as known to those skilled in the art. Total RNA was reverse transcribed (preferably using Superscript II RNaseH-Reverse Transcriptase, from Invitrogen, Karlsruhe, Germany) and subjected to Taqman analysis preferably using the Taqman 2×PCR Master Mix' (page 66, line 31: Weiterstadt, Germany; see Example 8). Taqman analysis was performed preferably using the following primer/probe pairs:

For the amplification of human Mnk2a:

```
human Mnk2a forward primer (SEQ ID NO: 17):
5'-cca tct ccc cct ctg tac ata gg-3';

human Mnk2a reverse primer (SEQ ID NO: 18):
5'-ccg get ggc gat age tta a-3';

Taqman probe (SEQ ID NO: 19):
(5/6-FAM) cac ccg tee ccc aat caa ate taa agg (5/6-TAMRA)
```

For the amplification of human Mnk2b:

```
human Mnk2b forward primer (SEQ ID NO: 20):
5'-TTA CTG TGA ATG AGT GAA GAT CCT GG-3';

human Mnk2b reverse primer (SEQ ID NO: 21 ):
5'-ATG GCC GTT CAC CGT CC-3';

Taqman probe (SEQ ID NO: 22):
(5/6-FAM) CCA GGC GAG CTC CCA TCG CTG (5/6-TAMRA)
```

Figure 9A:
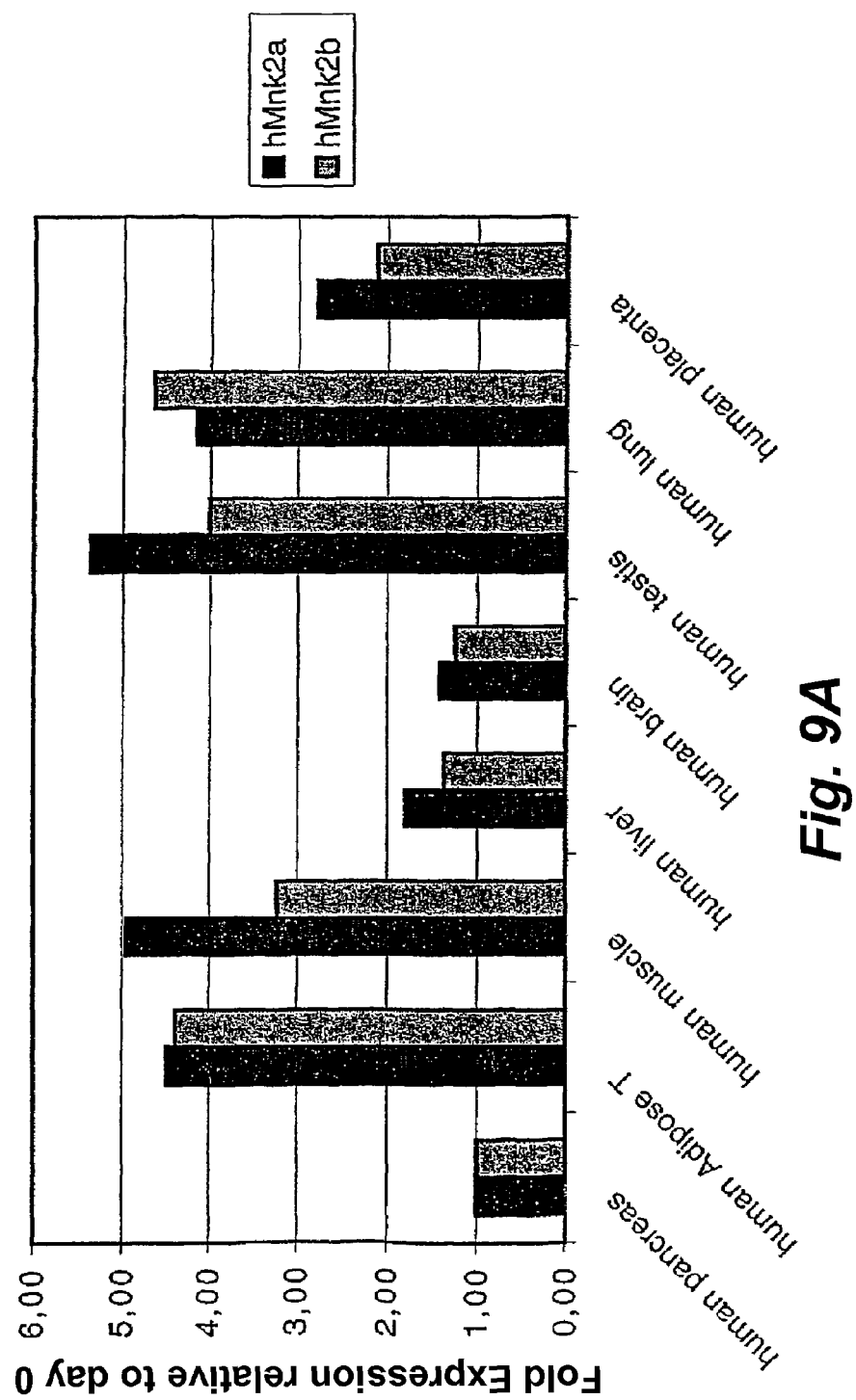
Figure 9B:
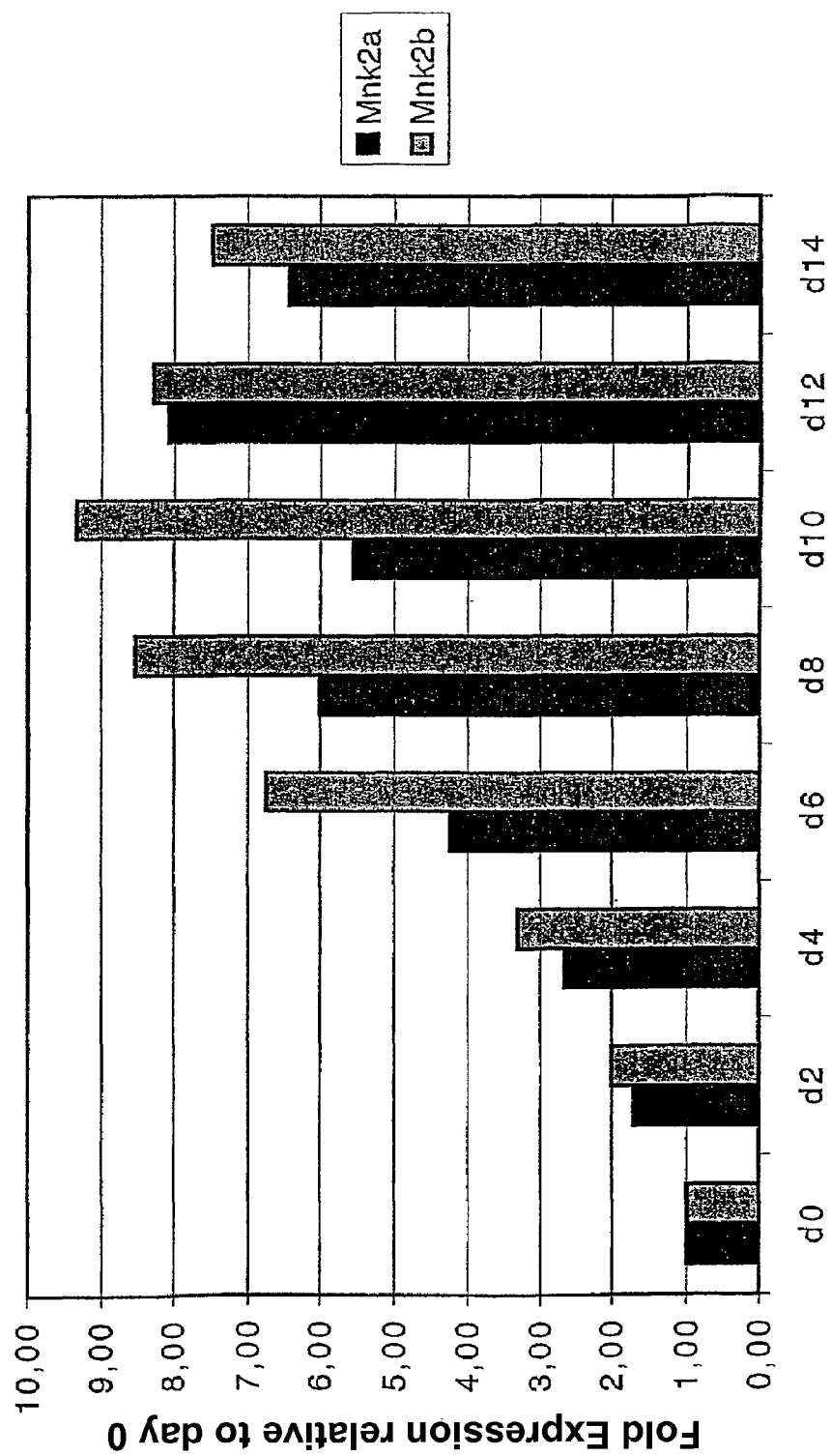

As shown in FIG. 9A, real time PCR (Taqman) analysis of the expression of Mnk2a and Mnk2b protein in human tissues revealed that both proteins are expressed in all tissues analyzed with high levels of expression in adipose tissue, muscle, lung, testis, and placenta. The relative expression levels of both human Mnk2 splice variants is the same for all tissues analyzed. Both show highest expression levels in tissues relevant for metabolic disorders namely adipose and muscle tissue. As shown in FIG. 9B, Mnk2a as well as Mnk2b are upregulated during human adipocyte differentiation. This suggests a function of both proteins in the metabolism of mature adipocytes.

Example 10

Assays for the Determination of Triglyceride Storage, Synthesis and Transport (FIG. 8)

Retroviral Infection of Preadipocytes

Packaging cells were transfected with retroviral plasmids pLPCX carrying mouse Mnk2 transgene and a selection marker using calcium phosphate procedure. Control cells were infected with pLPCX carrying no transgene. Briefly, exponentially growing packaging cells were seeded at a density of 350,000 cells per 6-well in 2 ml DMEM+10% FCS one day before transfection. 10 min before transfection chloroquine was added directly to the overlying medium (25 µM final concentration). A 250 µl transfection mix consisting of 5 µg plasmid-DNA (candidate: helper-virus in a 1:1 ratio) and 250 mM $CaCl_2$ was prepared in a 15 ml plastic tube. The same volume of 2×HBS (280 µM NaCl, 50 µM HEPES, 1.5 mM $Na_2HPO_4$, pH 7.06) was added and air bubbles were injected into the mixture for 15 sec. The transfection mix was added drop wise to the packaging cells, distributed and the cells were incubated at 37° C., 5% $CO_2$ for 6 hours. The cells were washed with PBS and the medium was exchanged with 2 ml DMEM+10% CS per 6-well. One day after transfection the cells were washed again and incubated for 2 days of virus collection in 1 ml DMEM+10% CS per 6-well at 32° C., 5% $CO_2$. The supernatant was then filtered through a 0.45 µm cellulose acetate filter and polybrene (final concentration 8 µg/ml) was added. Mammalian fibroblast (3T3-L1) cells in a sub-confluent state were overlaid with the prepared virus containing medium. The infected cells were selected for 1 week with 2 1-Jg/ml puromycin. Following selection the cells were checked for transgene expression by western blot and immunofluorescence. Over expressing cells were seeded for differentiation. 3T3-L 1 cells were maintained as fibroblasts and differentiated into adipocytes as described in the prior art and in example 8. For analysing the role of the proteins disclosed in this invention in the in vitro assays for the determination of triglyceride storage, synthesis and transport were performed.

Preparation of Cell Lysates for Analysis of Metabolites

Starting at confluence (DO), cell media was changed every 48 hours. Cells and media were harvested 8 hours prior to media change as follows. Media was collected, and cells were washed twice in PBS prior to lyses in 600 µl HB-buffer (0.5% Polyoxyethylene 10 tridecylethan, 1 mM EDTA, 0.01 M $NaH_2PO_4$, pH 7.4). After inactivation at 70° C. for 5 minutes, cell lysates were prepared on Bio 101 systems lysing matrix B (0.1 mm silica beads; Q-Biogene, Carlsbad, USA) by agitation for 2×45 seconds at a speed of 4.5 (Fastprep FP120, Bio 101 Thermosavant, Hoi brock, USA). Supernatants of lysed cells were collected after centrifugation at 3000 rpm for 2 minutes, and stored in aliquots for later analysis at −80° C.

Changes in cellular triglyceride levels during adipogenesis (FIG. 8A) Cell lysates and media were simultaneously analyzed in 96-well plates for total protein and triglyceride content using the Bio-Rad DC Protein assay reagent (Bio-Rad, Munich, Germany) according to the manufacturer's instructions and a modified enzymatic triglyceride kit (GPO-Trinder; Sigma) briefly final volumes of reagents were adjusted to the 96-well format as follows: 10 µl sample was incubated with 200 µl reagent A for 5 minutes at 37° C. After determination of glycerol (initial absorbance at 540 nm), 50 µl reagent B was added followed by another incubation for 5 minutes at 37° C. (final absorbance at 540 nm). Glycerol and triglyceride concentrations were calculated using a glycerol standard set (Sigma) for the standard curve included in each assay.

Figure 8A:
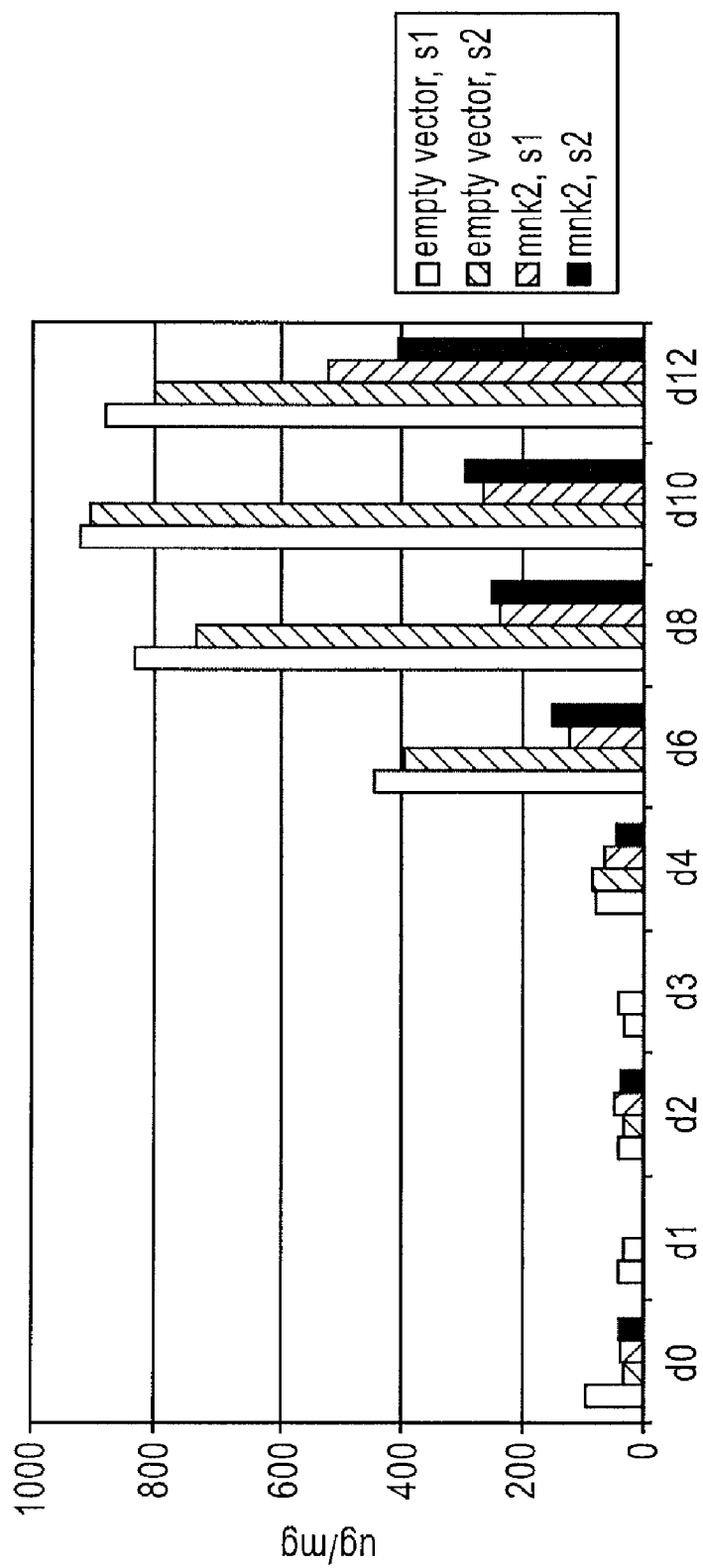
FIGS. 8A and 9B: In vitro assays for the determination of triglyceride storage, synthesis and transport.

As shown in FIG. 8A, we found that in Mnk2 overexpressing cells cellular triglyceride levels were significantly lower from day 4 to day 12 of adipogenesis compared to that in the control cells (FIG. 8A). These results indicate that Mnk2 targets regulatory pathways or enzymes involved in lipid metabolism, which we analyzed in more detail in the lipid synthesis and FFA transport assays described below.

Figure 8B:
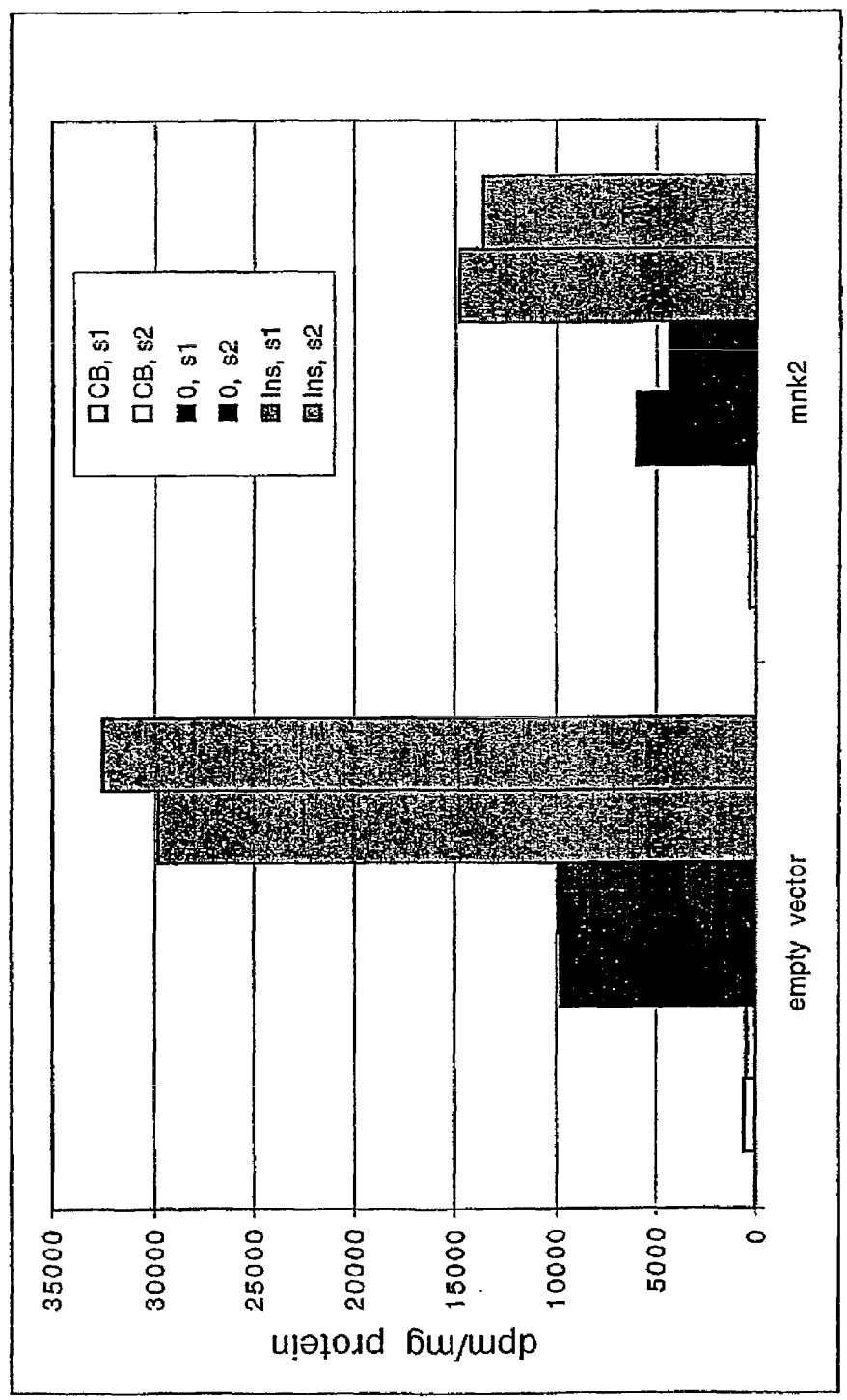
FIG. 8B shows reduction in insulin-stimulated lipid synthesis (dpm/mg protein) in cells over-expressing Mnk2 compared to control cells. All samples were analyzed in duplicates (s1; sample 1, s2; sample 2). CB; cytochalasin B, illustrates the background synthesis in 3T3L1, 0; represents the baseline or un-stimulated glucose transport and hence basal lipid synthesis in the cells, while Ins; insulin shows the stimulated glucose transport and the consequent synthesis of glucose to lipid in 3T3L1 cells. The Y-axis displays disintegrations per minutes/mg protein (dpm/mg protein) and the X-axis denotes the aforementioned proteins.

Synthesis of Lipids During Adipogenesis (FIG. 8B)

During the terminal stage of adipogenesis (day 12) cells were analyzed for their ability to metabolize lipids. A modified protocol to the method of Jensen et al (2000), JBC 275, 40148, for lipid synthesis was established. Cells were washed 3 times with PBS prior to serum starvation in Krebs-Ringer-Bicarbonate-Hepes buffer (KRBH; 134 nM NaCl, 3.5 mM KCl, 1.2 mM $KH_2PO_4$, 0.5 mM MgS04, 1.5 mM $CaCl_2$, 5 mM $NaHCO_3$, 1 0 mM Hepes, pH 7.4), supplemented with 0.1% FCS for 2.5 h at 37° C. For insulin-stimulated lipid synthesis, cells were incubated with 1 µM bovine insulin (Sigma; carrier: 0.005 N HCl) for 45 min at 37° C. Basal lipid synthesis was determined with carrier only. $^{14}$C(U)-D-Glucose (NEN Life Sciences) in a final activity of 1 µCi/Well/ml in the presence of 5 mM glucose was added for 30 min at 37° C. For the calculation of background radioactivity, 25 µM Cytochalasin B (Sigma) was used. All assays were performed in duplicate wells. To terminate the reaction, cells were washed 3 times with ice cold PBS, and lysed in 1 ml 0.1 N NaOH. Protein concentration of each well was assessed using the standard Biuret method (Protein assay reagent; Bio-Rad). Total lipids were separated from aqueous phase after overnight extraction in Insta-Fluor scintillation cocktail (Packard Bioscience) followed by scintillation counting.

Our results clearly show that Mnk2 overexpressing cells were less effective at synthesizing lipids from exogenous glucose. Consequently, the levels of insulin stimulated lipid synthesis are significantly lower at day 12 of adipogenesis when compared to control cells (FIG. 8B). The lower lipid levels observed in the experiments above therefore result most likely from a lower lipid synthesis rate and are not the result of an increased turnover of lipid stores.

Figure 8C:
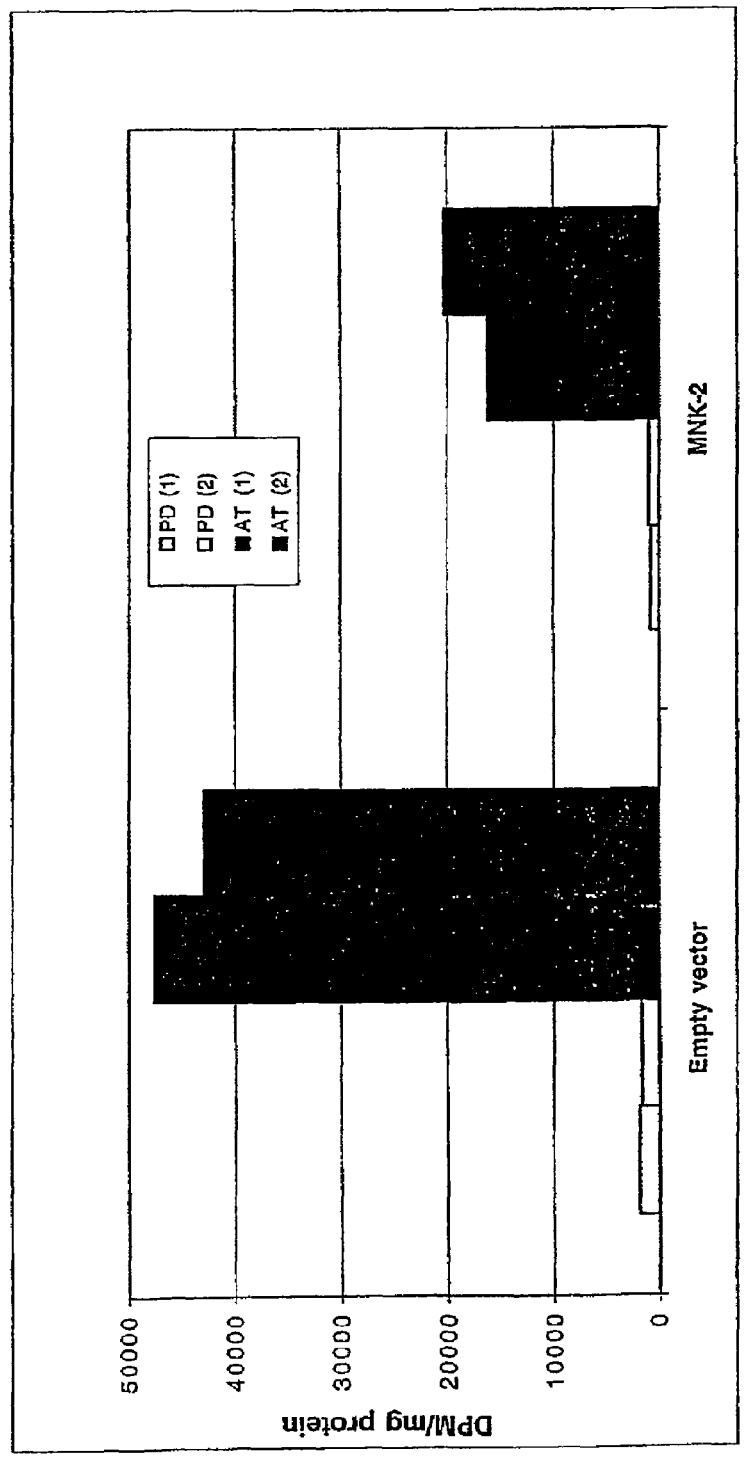
FIG. 8C shows reduction in active transport (AT) of free fatty acids across the plasma membrane of cells over expressing Mnk2 compared to control cells. All samples were analyzed in duplicates (as illustrated by twin bar of identical shadings). PD; passive diffusion illustrated the baseline or non-energy dependent transportation of exogenous fatty acids across the membrane. AT; active transport represents energy dependent transportation of fatty acids across the membrane. The Y-axis shows disintegrations per minutes/mg protein (dpm/mg protein) and the X-axis displays the aforementioned proteins.

Transport and Metabolism of Free Fatty Acids Across During Adipogenesis (FIG. 8C)

During the terminal stage of adipogenesis (D12) cells were analyzed for their ability to transport long chain fatty acid across the plasma membrane. A modified protocol to the method of Abumrad et al (1991) (Proc. Natl. Acad. Sci. USA, 1991: 88; 6008-12) for cellular transportation of fatty acid was established. In summary, cells were washed 3 times with PBS prior to serum starvation. This was followed by incubation in KRBH buffer, supplemented with 0.1% FCS for 2.5 h at 37° C. Uptake of exogenous free fatty acids was initiated by the addition of isotopic media containing non radioactive oleate and ($^3$H)oleate (NEN Life Sciences) complexed to serum albumin in a final activity of 1 µCi/Well/ml in the presence of 5 mM glucose for 30 min at room temperature (RT). For the calculation of passive diffusion (PD) in the absence of active transport (AT) across the plasma membrane 20 mM of phloretin in glucose free media (Sigma) was added for 30 min at room temperature (RT). All assays were performed in duplicate wells. To terminate the active transport 20 mM of phloretin in glucose free media was added to the cells. Cells were lysed in 1 ml 0.1 N NaOH and the protein concentration of each well were assessed using the standard Biuret method (Protein assay reagent; Bio-Rad). Esterified fatty acids were separated from free fatty acids using overnight extraction in Insta-Fluor scintillation cocktail (Packard Bioscience) followed by scintillation counting.

We found that transport of exogenous fatty acids across the plasma membrane of Mnk2 overexpressing cells and hence esterification of these metabolites were considerably lower at day 12 of adipogenesis when compared to control cells (FIG. 8C). Taken together the overexpression of Mnk2 showed an effect on triglyceride metabolism in all three assays we performed in 3T3-L1 cells, making it a potential interesting drug target to treat metabolic disorders.

Example 11

Generation and Analysis of Mnk2 Transgenic Animals (I3-Actin-mMnk2DN)

Generation of the Transgenic Animals

Mouse Mnk2 cDNA was isolated from mouse brown adipose tissue (BAT) using standard protocols as known to those skilled in the art. The cDNA was amplified by RT-PCR using the following primer pair:

```
Mnk2 forward primer (SEQ ID NO: 23):
5' AAG TTG GCC TTC GCG TTA GAG 3'

Mnk2 reverse primer (SEQ ID NO: 24):
5' CGA TAT GTA CAA GGA GCT AG 3'.
```

The resulting Mnk2 cDNA was cloned into pBluescript KS+ (Stratagene) according to standard protocols, resulting in a plasmid referred to as pKS+-mMnk2'. The cDNA of pKS+-mMnk2 c was mutated using site directed mutatagenesis (Stratagene), according to the manufacturer's instructions. Using the Mnk2 top oligo (SEQ ID NO.: 25): 5' CTC CCC CAT CTC CGC ACC AGA GCT GCT CGC CCC GTG TGG GTC AG 3' and the Mnk2 bottom oligo (SEQ ID NO.: 26): 5' CTG ACC CAC ACG GGG CGA GCT CTG GTG CGG AGA TGG GGG AG 3', two point mutations were introduced into the cDNA resulting in amino acid exchanges at position T197 and T202 to A197 and A202 of the Mnk2 cDNA.

The resulting mutated cDNA (referred to as mMnk2DN) was cloned into the EcoRV cloning site of the transgenic expression vector pTG-β-actin-X-hgh-bgh-polyA. The 13-actin-Mnk2DN transgene was microinjected into the male pronucleus of fertilized mouse embryos (preferably strain C57/BL6/CBA F1 (Harlan Winkelmann). Injected embryos were transferred into pseudo-pregnant foster mice. Transgenic founders were detected by PCR analysis using the forward primer (SEQ ID NO.: 27): 5' GCT GCT GGT CCG AGA TGC C 3' and reverse primer (SEQ ID NO.: 28): 5' GGG TCA TGC GCG ATC CCC 3'. Two independent transgenic mouse lines containing the β-actin-Mnk2DN construct were established and kept on a C57/BL6 background. Briefly, founder animals were backcrossed with C57/BL6 mice to generate F1 mice for analysis. Transgenic mice were continuously bred onto the C57/BL6 background.

Figure 10:
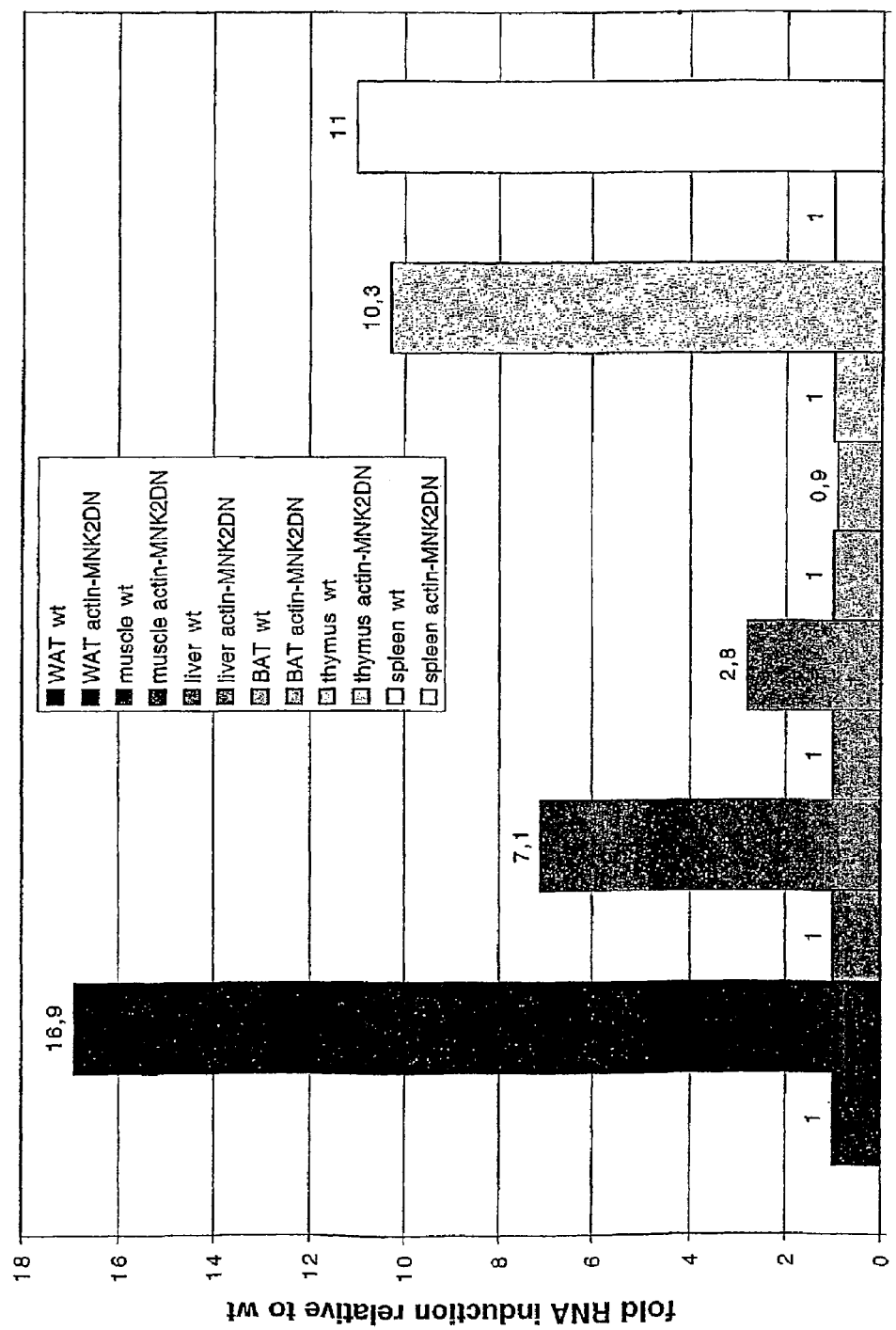
FIG. 10 shows the expression of the ectopic mouse Mnk2 (mMnk2DN) transgene in actin-mMnk2DN transgenic mice. Shown is a Taqman analysis on different tissues isolated from male actin-mMnk2DN transgenic mice and male wild-type littermates. Data are expressed as fold RNA induction relative to the corresponding wild-type (wt) tissue. The number on top of each bar indicates the fold induction relative to the corresponding wt tissue. Shown is a representative experiment.

Expression of the construct in different mouse tissues (FIG. 10) using standard techniques, β-actin-Mnk2DN transgene expression was verified by Taqman analysis using forward primer (SEQ ID NO.: 29): 5' CAG CGT GGT AGT ACA GGA CGT G 3', reverse primer (SEQ ID NO.: 30): 5' TCC CTG TGG GCG ATG C 3' and primer (SEQ ID NO.: 31): 5' CAG TGC CCT GGA CTT CCT GCA TAA CAA 3'. Taqman analysis was performed using a representative panel of mouse tissues.

The expression of the bactin-Mnk2DN transgene was observed in the following tissues: WAT, muscle, liver, kidney, thymus, heart, lung, and spleen. Expression levels of the transgene were 2.8-16.9 fold increased relative to Mnk2 expression in wild-type mice, depending on the tissue analyzed. No Mnk2 transgene expression was detected in BAT tissue (see FIG. 1 0).

Figure 11:
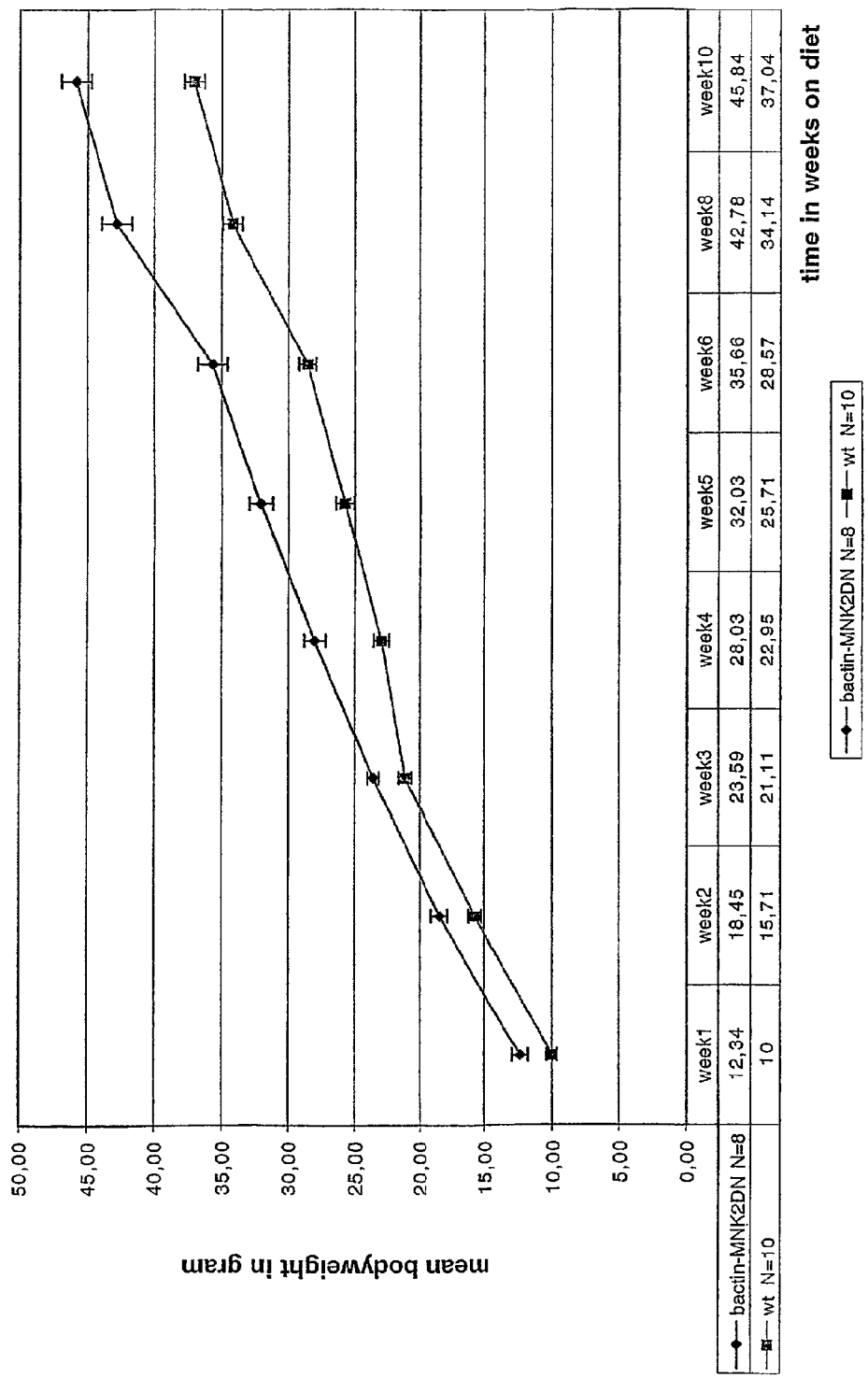
FIG. 11 shows that the ectopic mouse Mnk2 (mMnk2DN) expression in actin-mMnk2DN transgenic mice leads to increased body weight. Shown are growth curves from male bactin-mMnk2DN transgenic mice (♦, upper trace) and male wt littermates (■, lower trace) on high fat diet over a time of 10 weeks. Data are expressed as mean body weight overtime+/−SE. Shown is a representative experiment with N=8 respectively N=10 mice per group.

Analysis of the Bodyweight of the Transgenic Mice (FIG. 11)

After weaning, male β-actin-mMnk2DN transgenic mice and their wild-type (wt) littermates controls were placed in groups of 4 to 5 animals (N=4 up to N=5) on control diet (preferably Altromin C1057 mod control, 4.5% crude fat or high fat diet (preferably Altromin C1057mod. high fat, 23.5% crude fat). Total body weight of the animals was measured weekly over a period of 12-16 weeks. On each diet, mean bodyweight of β-actin-mMnk2DN transgenic mice was clearly increased compared to wildtype littermates on the respective diet. Significant differences in mean bodyweight were first observed around the end of postnatal week 4 on both diets. After 10 weeks on high fat diet, the mean bodyweight of β-actin-mMnk2DN transgenic mice compared to wt littermates was increased by 8.8 g (=23% increase in mean bodyweight relative to wt littermates) (FIG. 11). Similar differences in mean body weight were observed in wt and β-actin-mMnk2DN transgenic mice on control diet (data not shown). Thus, our results clearly show that the ectopic expression of mMnk2DN transgene leads to an increase in bodyweight. The effect appears independently of the diet give, as it can be seen on control diet as well as on high fat diet.

Example 12

Figure 13:
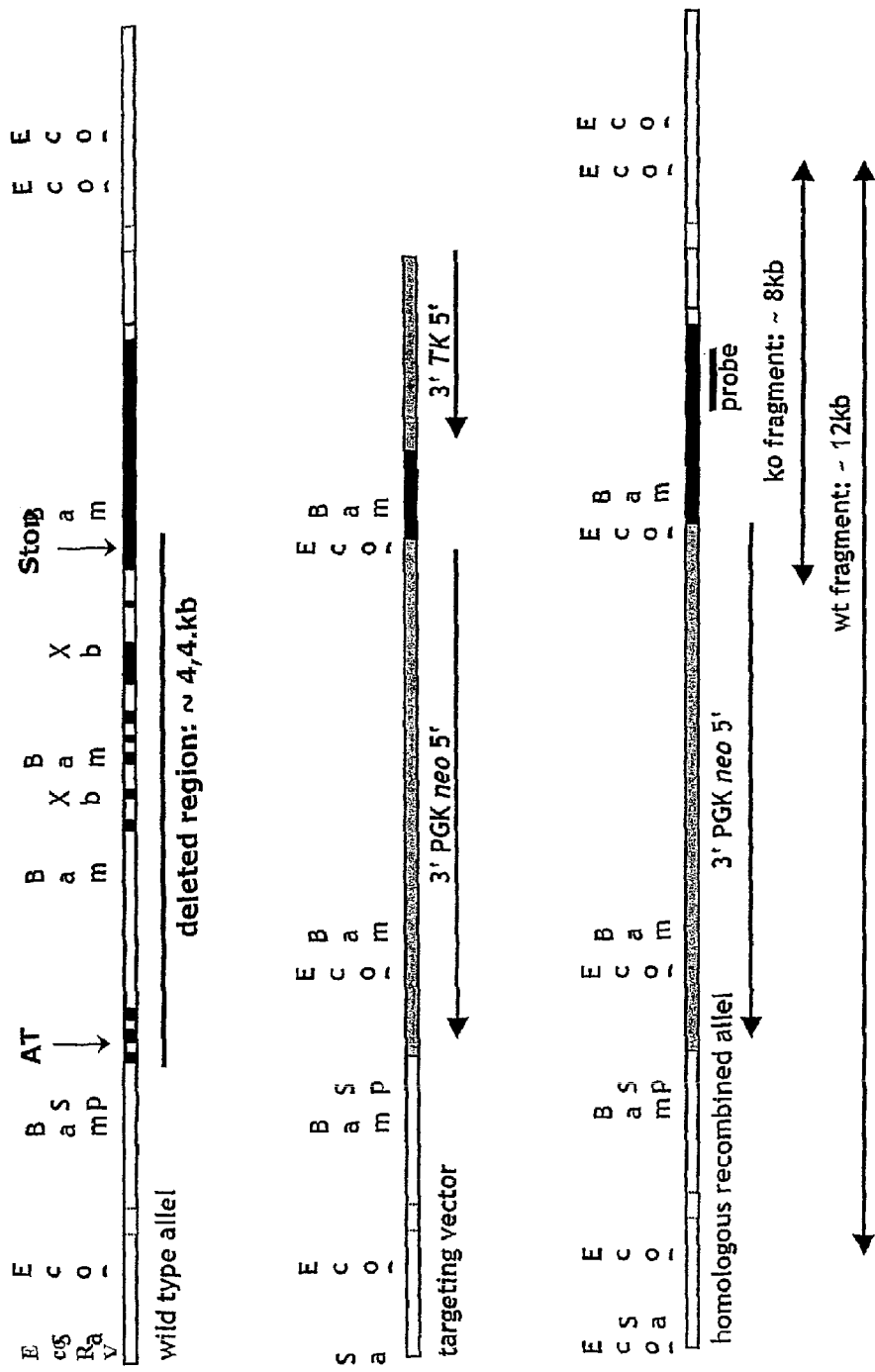
FIG. 13 illustrates the targeted deletion of the mouse Mnk2 gene by homologous recombination. The top line shows the wild type locus of mouse Mnk2, the graphic in the middle shows the targeting vector, and the graphic at the bottom part of the figure illustrates the targeted locus. The exons are shown as black boxes. Restriction sites, translation start site, and stop codon are indicated. The PGK-NEO cassette and the TK cassette are shown as grey boxes. 4.4 kb of genomic region of the mouse Mnk2 gene is replaced by a PGK NEO cassette. The deleted region is indicated. The outside flanking probe used for Southern blot analysis is shown by a black bar. The genomic fragments detected with this probe on EcoR1 digested DNA are shown as arrows. See examples for more detail.

Generation and Analysis of mMnk2−/− Mice (FIG. 12 and FIG. 13)

A 605 base pair probe of the mMnk2 cDNA (GenBank accession number BC010256; position 61-665) was amplified from mouse white adipose tissue (WAT) cDNA by PCR using forward primer (SEQ ID NO.: 32): 5' ACA TCA GCC CAC AGT GTG A 3' and reverse primer (SEQ ID NO.: 33): 5' TCT CCA TTG AGT TTG AT A CCA 3'. This probe was used to screen a 129SV J genomic phage library (obtained from Stratagene). Three independent clones were isolated and subcloned into the NotI cloning site of pBluescript KS+ (Stratagene). These genomic clones were used for restriction mapping and sequencing to characterize the genomic locus of mouse Mnk2 (FIG. 12). A PGK-neomycin cassette was inserted into the locus of mouse Mnk2 replacing 4.4 kb of genomic DNA thereby deleting the complete coding region of mMnk2. Briefly, an 8 kb SpeI-NotI fragment was cloned into the XbaI site of pBluescript KS+ upstream of the PGK-Neomycin cassette, which was inserted into the SmaI site of pBluescript. A 1 kb genomic fragment was amplified by PCR using the following primer pair (non priming nucleotides/attached restriction sites are lower case letters): Mnk2-SA forward primer (SEQ ID NO.: 34): EcoRI 5' cgg aat CCA CTA GCT CCT TGT ACA TAT 3'; Mnk2-SA reverse primer (SEQ ID NO.: 35): ClaI 5' cca tcg atG GAA CTC GTA TTG CAT AGT AG 3'. The resulting fragment was inserted into the EcoRI/ClaI site of pBluescript KS+. As a negative selection marker a thymidine kinase cassette was cloned into ClaI/XhoI site of the targeting construct. (FIG. 13). The construct was linearized by NotI digestion and electroporated into mouse embryonic stem (ES) cells. ES cell clones were selected by G418 and Gancyclovir treatment (preferably 350 µg G418 1 ml and 2 µM Gancyclovir). Out of 600 neomycin resistant colonies, two independent homologous recombined ES cell clones were identified by PCR. The results were confirmed by southern blot analysis with EcoRI digested genomic DNA using a 3' flanking probe (position 2495-3065 mMnk2 cDNA). A single integration event was confirmed by Southern blot analysis of BamHI digested DNA with a Neomycin probe. ES cell clones were aggregated with 8-cell-stage embryos from NMRI mice and developing blastocysts were transferred into pseudo-pregnant mice to generate chimeras. Chimeras were bred with C57/BL6 mice and offsprings were genotyped by PCR using the following primers: Mnk2-ES primer (SEQ ID NO.: 36): 5' AGA CTA GGG AGG AGG GTG GAG GA 3'; Mnk2-KO primer (SEQ ID NO.: 37): 5' GGT GGA TGT GGA ATG TGT GCG A 3'; Mnk2-WT 5' GGG GTG TAG GGG TCT GTT AGG 3'. Heterozygous mice were used for further intercrosses and analyzed.

Example 13

Small Molecule Screening

Compounds which are suitable for the prophylaxis, treatment or diagnosis of Mnk-related metabolic disorders may be identified via a kinase assay, a binding assay or any other suitable assay to measure a function associated with the Mnk polypeptide, a Mnk polypeptide fragment or derivative thereof. This kinase assay may be based on recombinant human Mnk2 (Mnk2a or Mnk2b) or Mnk1 protein and a labelled peptide comprising the eIF4E target sequence, a labelled recombinant eIF4E target sequence or a labelled recombinant eiF4E protein as a substrate. The assay may be a radioactive kinase assay or an assay based on using an anti-phosphoserine antibody which is capable of recognizing eIF4E phosphorylation at Ser209.

For example, the kinases Mnk2a (GenBank Accession Number AF237775 (SEQ ID NO.: 2); see also FIGS. 3D and 3E), Erk2 (GenBank Accession Number M84489, SEQ ID NO.: 84) and a double point mutant of Mek1 (GenBank Accession Number 002750) containing the amino acid substitutions Ser218Asp and Ser222Glu (S218D S222E) were expressed in E. coli and subsequently purified using methods known to those skilled in the art. Preferably, in a kinase reaction of 50 µl, 2.0 µM Mnk2a was incubated with 200 nM Erk2 plus 20 nM Mek1 S218D S222E (labelled lanes 1 to 4 in FIG. 14) or with 50 nM Erk2 plus 2.5 nM Mek1 S218D S222E (labelled lanes 5 to 8 in FIG. 14) in the presence of 1.0 mM ATP, 50 mM Hepes/KOH, mM magnesium chloride and 0.5 mM OTT at 30° C. At the indicated time points (0, 10, 20 and 40 minutes, see FIG. 14), samples were taken from the reaction, diluted in SDS sample buffer containing 50 mM EDTA and separated by SDS polyacrylamide gel electrophoresis (SDS-PAGE). SDS-PAGE separated reaction samples were blotted onto nitrocellulose and probed with an antibody against a phospho-epitope, essential for the activation of Mnk (anti-Phospho-Mnk Thr197/202; Cell Signaling Technology, Inc., Beverly, Mass.). The anti-Phospho-Mnk antibody was detected with a peroxidase-coupled anti rabbit antibody (Sigma-Aldrich, St. Louis, Mo.) as described elsewhere (Harlow and Lane, 1998, Antibodies, Cold Spring Harbor Laboratory Press, NY).

Figure 14:
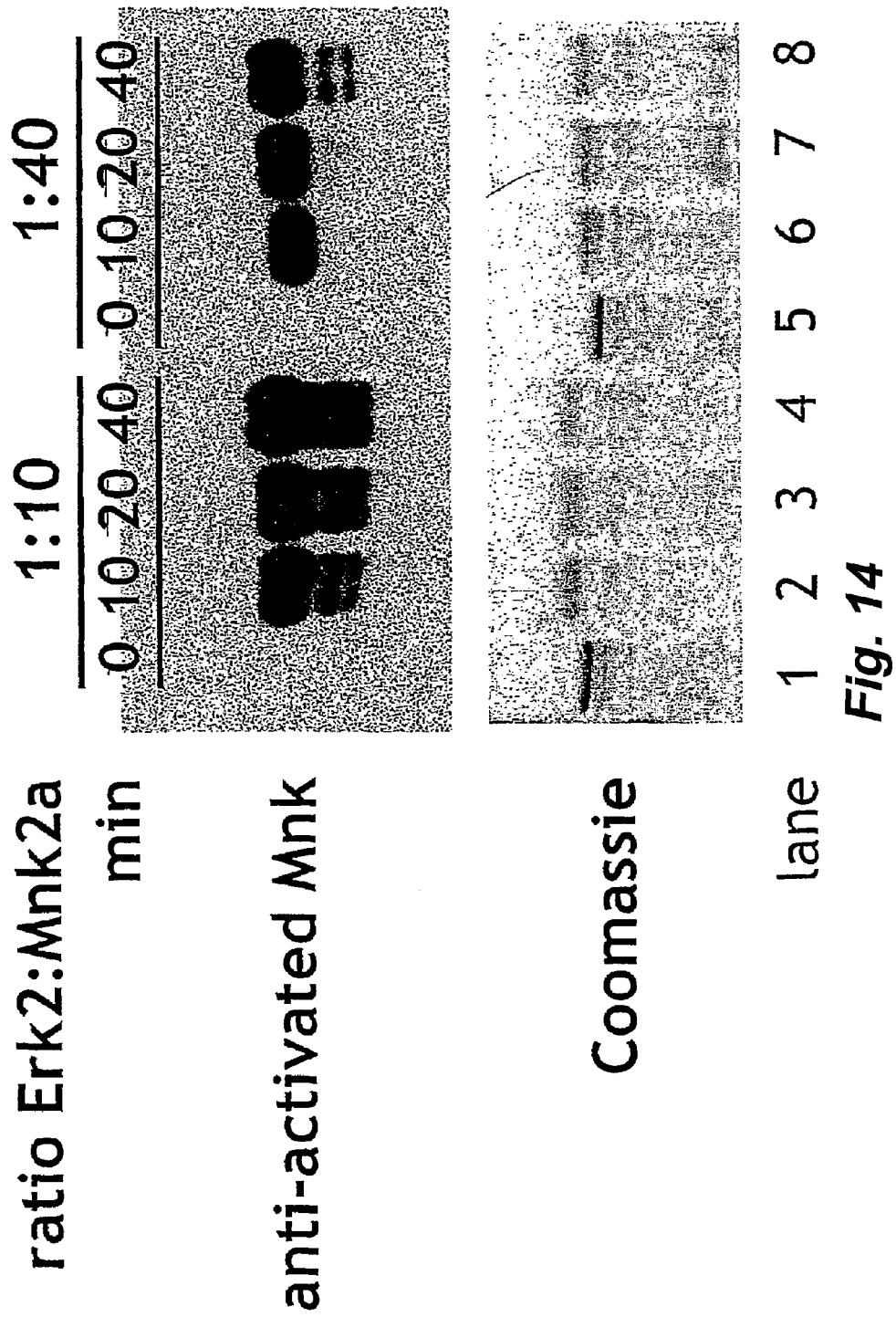
FIG. 14 shows that purified Mnk2a can be activated in vitro with a preparation of the kinases Erk2 and the double point mutant Mek1 S218D S222E.

As the reaction progresses, the activation of Mnk2a can be visualized by Mnks immuno-reactivity with the anti Phospho-Mnk antibody (see upper panel in FIG. 14). In addition, Mnk2a was visualized by Coomassie staining of the gel. Arrows indicate the Coomassie stained Mnk2a as its mobility is retarded with increasing phosphorylation (see lower panel in FIG. 14).

The generation of the phospho-epitope, essential for the activation of Mnk2a, and the high degree of efficiency of this process (as shown by the nearly complete electrophoretic mobility shift) demonstrate the suitability of this approach to produce enzymatically active Mnk2a.

For the validation of the assay, known Mnk inhibitors such as CGP57380 or CGP025088 may be used (see, Knauf et al., 2001, Mol. Cell. Biol. 21:5500, Tschopp et al., 2000, Mol Cell Biol Res Comm 3:205 and Slentz-Kesler et al., 2000, Genomics 69:63). As a negative control, CGP052088 may be used.

Alternatively, the screening may comprise the use of cellular based screening systems, e.g. prokaryotic or eukaryotic cells which overexpress Mnk proteins. Furthermore, transgenic animals capable of overexpressing or underexpressing Mnk2 and/or Mnk1 may be used.

All publications and patents mentioned in the above specification are herein incorporated by reference.

Various modifications and variations of the described method and system of the invention will be apparent to those skilled in the art without departing from the scope and spirit of the invention. Although the invention has been described in connection with specific preferred embodiments, it should be

We claim:

1. A method of screening for a candidate inhibitor of a pancreatic malfunction that decreases the kinase activity of Mitogen Activating Protein Kinase Interacting Kinases Mnk2a or Mnk2b, wherein said kinase activity is associated with type 2 diabetes, said method comprising the steps of:
   (a) identifying an inhibitor of the kinase activity of Mnk2a or Mnk2b by:
   (i) determining a first level of kinase activity of Mnk2a or Mnk2b in the absence of a candidate Mnk2 inhibitor;
   (ii) determining a second level of kinase activity of Mnk2a or Mnk2b in the presence of the Mnk2 candidate inhibitor;
   (iii) comparing the first and the second levels of the kinase activity of the Mnk2a or Mnk2b, wherein if the second level of kinase activity is less than the first level then the candidate inhibitor is identified as an Mnk2 inhibitor; and
   (b) determining if the Mnk2 inhibitor identified from step (iii) increases insulin-stimulated glucose transport and lipid synthesis during adipogenesis of preadipocyte cells, thereby identifying the Mnk2 inhibitor as a candidate for screening as an inhibitor of type 2 diabetes.

2. The method of claim 1, wherein the candidate inhibitor is selected from the group consisting of: a peptide and a small organic compound having a molecular weight of more than 50 Da and less than about 2500 Da.

3. The method of claim 1, wherein a known Mnk inhibitor is used as a control for the candidate inhibitor which decreases the kinase activity of Mnk2a or Mnk2b.

* * * * *

SEQUENCE LISTING

<160> NUMBER OF SEQ ID NOS: 53

<210> SEQ ID NO 1
<211> LENGTH: 1444
<212> TYPE: DNA
<213> ORGANISM: Homo sapiens

<400> SEQUENCE: 1

```
cggtcccctc ccccgctggc ggggcccgga cagaagatgg tgcagaagaa accagccgaa      60
cttcagggtt tccaccgttc gttcaagggg cagaacccct tcgagctggc cttctccta     120
gaccagcccg accacggaga ctctgacttt ggcctgcagt gctcagcccg ccctgacatg    180
cccgccagcc agcccattga catcccggac gccaagaaga ggggcaagaa gaagaagcgc    240
ggccgggcca ccgacagctt ctcgggcagg tttgaagacg tctaccagct gcaggaagat    300
gtgctggggg agggcgctca tgcccgagtg cagacctgca tcaacctgat caccagccag    360
gagtacgccg tcaagatcat tgagaagcag ccaggccaca ttcggagcag ggttttcagg    420
gaggtggaga tgctgtacca gtgccaggga cacaggaacg tcctagagct gattgagttc    480
ttcgaggagg aggaccgctt ctacctggtg tttgagaaga tgcggggagg ctccatcctg    540
agccacatcc acaagcgccg gcacttcaac gagctggagg ccagcgtggt ggtgcaggac    600
gtggccagcg ccttggactt tctgcataac aaaggcatcg cccacaggga cctaaagccg    660
gaaaacatcc tctgtgagca ccccaaccag gtctcccccg tgaagatctg tgacttcgac    720
ctgggcagcg gcatcaaact caacggggac tgctccccta tctccaccc ggagctgctc    780
actccgtgcg gctcggcgga gtacatggcc ccggaggtag tggaggcctt cagcgaggag    840
gctagcatct acgacaagcg ctgcgacctg tggagcctgg gcgtcatctt gtatatccta    900
ctcagcggct acccgcccct cgtgggccgc tgtggcagcg actgcggctg ggaccgcggc    960
gaggcctgcc ctgcctgcca aacatgctg tttgagagca tccaggaggg caagtacgag   1020
ttccccgaca aggactgggc ccacatctcc tgcgctgcca aagacctcat ctccaagctg   1080
ctggtccgtg acgccaagca gaggctgagt gccgcccaag tcctgcagca cccctgggtt   1140
cagggtgcg ccccggagaa caccttgccc actcccatgg tcctgcagag aacagctgt    1200
gccaaagacc tcacgtcctt cgcggctgag gccattgcca tgaaccggca gctggcccag   1260
cacgacgagg acctggctga ggaggaggcc gcggggcagg ccagcccgt cctggtccga   1320
gctacctcac gctgcctgca gctgtctcca ccctcccagt ccaagctggc cagcggcgg   1380
caaagggcca gtctgtcctc ggcccagtg gtcctggtgg agaccacgc ctgaccctcc   1440
catc                                                               1444
```

<210> SEQ ID NO 2
<211> LENGTH: 1285
<212> TYPE: PRT
<213> ORGANISM: Homo sapiens

<400> SEQUENCE: 2

```
Met Glu Thr Val Ala Leu Gly Leu Asn Leu Tyr Ser Leu Tyr Ser Pro
 1               5                  10                  15

Arg Ala Leu Ala Gly Leu Leu Glu Gly Leu Asn Gly Leu Tyr Pro His
                20                  25                  30
```

-continued

Glu His Ile Ser Ala Arg Gly Ser Glu Arg Pro His Glu Leu Tyr Ser
         35                  40                  45

Gly Leu Tyr Gly Leu Asn Ala Ser Asn Pro Arg Pro His Glu Gly Leu
     50                  55                  60

Leu Glu Ala Leu Ala Pro His Glu Ser Glu Arg Leu Glu Ala Ser Pro
65                  70                  75                  80

Gly Leu Asn Pro Arg Ala Ser Pro His Ile Ser Gly Leu Tyr Ala Ser
                 85                  90                  95

Pro Ser Glu Arg Ala Ser Pro Pro His Glu Gly Leu Tyr Leu Glu Gly
             100                 105                 110

Leu Asn Cys Tyr Ser Ser Glu Arg Ala Leu Ala Ala Arg Gly Pro Arg
         115                 120                 125

Ala Ser Pro Met Glu Thr Pro Arg Ala Leu Ala Ser Glu Arg Gly Leu
    130                 135                 140

Asn Pro Arg Ile Leu Glu Ala Ser Pro Ile Leu Glu Pro Arg Ala Ser
145                 150                 155                 160

Pro Ala Leu Ala Leu Tyr Ser Leu Tyr Ser Ala Arg Gly Gly Tyr Leu
                165                 170                 175

Tyr Ser Leu Tyr Ser Leu Tyr Ser Leu Tyr Ser Ala Arg Gly Gly Leu
            180                 185                 190

Tyr Ala Arg Gly Ala Leu Ala Thr His Arg Ala Ser Pro Ser Glu Arg
        195                 200                 205

Pro His Glu Ser Glu Arg Gly Leu Tyr Ala Arg Gly Pro His Glu Gly
    210                 215                 220

Leu Ala Ser Pro Val Ala Leu Thr Tyr Arg Gly Leu Asn Leu Glu Gly
225                 230                 235                 240

Leu Asn Gly Leu Ala Ser Pro Val Ala Leu Leu Glu Gly Leu Tyr Gly
                245                 250                 255

Leu Gly Leu Tyr Ala Leu Ala His Ile Ser Ala Leu Ala Ala Arg Gly
            260                 265                 270

Val Ala Leu Gly Leu Asn Thr His Arg Cys Tyr Ser Ile Leu Glu Ala
        275                 280                 285

Ser Asn Leu Glu Ile Leu Glu Thr His Arg Ser Glu Arg Gly Leu Asn
    290                 295                 300

Gly Leu Thr Tyr Arg Ala Leu Ala Val Ala Leu Leu Tyr Ser Ile Leu
305                 310                 315                 320

Glu Ile Leu Glu Gly Leu Leu Tyr Ser Gly Leu Asn Pro Arg Gly Leu
                325                 330                 335

Tyr His Ile Ser Ile Leu Glu Ala Arg Gly Ser Glu Arg Ala Arg Gly
            340                 345                 350

Val Ala Leu Pro His Glu Ala Arg Gly Gly Leu Val Ala Leu Gly Leu
        355                 360                 365

Met Glu Thr Leu Glu Thr Tyr Arg Gly Leu Asn Cys Tyr Ser Gly Leu
    370                 375                 380

Asn Gly Leu Tyr His Ile Ser Arg Gly Ala Ser Asn Val Ala Leu
385                 390                 395                 400

Leu Glu Gly Leu Leu Glu Ile Leu Glu Gly Leu Pro His Glu Pro His
                405                 410                 415

Glu Gly Leu Gly Leu Gly Leu Ala Ser Pro Ala Arg Gly Pro His Glu
            420                 425                 430

Thr Tyr Arg Leu Glu Val Ala Leu Pro His Glu Gly Leu Leu Tyr Ser
        435                 440                 445

Met Glu Thr Ala Arg Gly Gly Leu Tyr Gly Leu Tyr Ser Glu Arg Ile

```
            450                 455                 460
Leu Glu Leu Glu Ser Glu Arg His Ile Ser Ile Glu His Ile Ser Leu
465                 470                 475                 480

Tyr Ser Ala Arg Gly Ala Arg Gly His Ile Ser Pro His Glu Ala Ser
                485                 490                 495

Asn Gly Leu Leu Glu Gly Leu Ala Leu Ala Ser Glu Arg Val Ala Leu
            500                 505                 510

Val Ala Leu Val Ala Leu Gly Leu Asn Ala Ser Pro Val Ala Leu Ala
        515                 520                 525

Leu Ala Ser Glu Arg Ala Leu Ala Leu Glu Ala Ser Pro Pro His Glu
    530                 535                 540

Leu Glu His Ile Ser Ala Ser Asn Leu Tyr Ser Gly Leu Tyr Ile Leu
545                 550                 555                 560

Glu Ala Leu Ala His Ile Ser Ala Arg Gly Ala Ser Pro Leu Glu Leu
                565                 570                 575

Tyr Ser Pro Arg Gly Leu Ala Ser Asn Ile Leu Glu Leu Glu Cys Tyr
            580                 585                 590

Ser Gly Leu His Ile Ser Pro Arg Ala Ser Asn Gly Leu Asn Val Ala
        595                 600                 605

Leu Ser Glu Arg Pro Arg Val Ala Leu Leu Tyr Ser Ile Leu Glu Cys
    610                 615                 620

Tyr Ser Ala Ser Pro Pro His Glu Ala Ser Pro Leu Glu Gly Leu Tyr
625                 630                 635                 640

Ser Glu Arg Gly Leu Tyr Ile Leu Glu Leu Tyr Ser Leu Glu Ala Ser
                645                 650                 655

Asn Gly Leu Tyr Ala Ser Pro Cys Tyr Ser Ser Glu Arg Pro Arg Ile
            660                 665                 670

Leu Glu Ser Glu Arg Thr His Arg Pro Arg Gly Leu Leu Glu Leu Glu
        675                 680                 685

Thr His Arg Pro Arg Cys Tyr Ser Gly Leu Tyr Ser Glu Arg Ala Leu
    690                 695                 700

Ala Gly Leu Thr Tyr Arg Met Glu Thr Ala Leu Ala Pro Arg Gly Leu
705                 710                 715                 720

Val Ala Leu Val Ala Leu Gly Leu Ala Leu Ala Pro His Glu Ser Glu
                725                 730                 735

Arg Gly Leu Gly Leu Ala Leu Ala Ser Glu Arg Ile Leu Glu Thr Tyr
            740                 745                 750

Arg Ala Ser Pro Leu Tyr Ser Ala Arg Gly Cys Tyr Ser Ala Ser Pro
        755                 760                 765

Leu Glu Thr Arg Pro Ser Glu Arg Leu Glu Gly Leu Tyr Val Ala Leu
    770                 775                 780

Ile Leu Glu Leu Glu Thr Tyr Arg Ile Leu Glu Leu Glu Leu Glu Ser
785                 790                 795                 800

Glu Arg Gly Leu Tyr Thr Tyr Arg Pro Arg Pro Arg Pro His Glu Val
                805                 810                 815

Ala Leu Gly Leu Tyr Ala Arg Gly Cys Tyr Ser Gly Leu Tyr Ser Glu
            820                 825                 830

Arg Ala Ser Pro Cys Tyr Ser Gly Leu Tyr Thr Arg Pro Ala Ser Pro
        835                 840                 845

Ala Arg Gly Gly Leu Tyr Gly Leu Ala Leu Ala Cys Tyr Ser Pro Arg
    850                 855                 860

Ala Leu Ala Cys Tyr Ser Gly Leu Asn Ala Ser Asn Met Glu Thr Leu
865                 870                 875                 880
```

```
Glu Pro His Glu Gly Leu Ser Glu Arg Ile Leu Gly Leu Asn Gly
            885                 890                 895

Leu Gly Leu Tyr Leu Tyr Ser Thr Tyr Arg Gly Leu Pro His Glu Pro
            900                 905                 910

Arg Ala Ser Pro Leu Tyr Ser Ala Ser Pro Thr Arg Pro Ala Leu Ala
            915                 920                 925

His Ile Ser Ile Leu Glu Ser Glu Arg Cys Tyr Ser Ala Leu Ala Ala
            930                 935                 940

Leu Ala Leu Tyr Ser Ala Ser Pro Leu Glu Ile Leu Glu Ser Glu Arg
945                 950                 955                 960

Leu Tyr Ser Leu Glu Leu Glu Val Ala Leu Ala Arg Gly Ala Ser Pro
            965                 970                 975

Ala Leu Ala Leu Tyr Ser Gly Leu Asn Ala Arg Gly Leu Glu Ser Glu
            980                 985                 990

Arg Ala Leu Ala Ala Leu Ala Gly Leu Asn Val Ala Leu Leu Glu Gly
            995                 1000                1005

Leu Asn His Ile Ser Pro Arg Thr Arg Pro Val Ala Leu Gly Leu
            1010                1015                1020

Asn Gly Leu Tyr Cys Tyr Ser Ala Leu Ala Pro Arg Gly Leu Ala
            1025                1030                1035

Ser Asn Thr His Arg Leu Glu Pro Arg Thr His Arg Pro Arg Met
            1040                1045                1050

Glu Thr Val Ala Leu Leu Glu Gly Leu Asn Ala Arg Gly Ala Ser
            1055                1060                1065

Asn Ser Glu Arg Cys Tyr Ser Ala Leu Ala Leu Tyr Ser Ala Ser
            1070                1075                1080

Pro Leu Glu Thr His Arg Ser Glu Arg Pro His Glu Ala Leu Ala
            1085                1090                1095

Ala Leu Ala Gly Leu Ala Leu Ala Ile Leu Glu Ala Leu Ala Met
            1100                1105                1110

Glu Thr Ala Ser Asn Ala Arg Gly Gly Leu Asn Leu Glu Ala Leu
            1115                1120                1125

Ala Gly Leu Asn His Ile Ser Ala Ser Pro Gly Leu Ala Ser Pro
            1130                1135                1140

Leu Glu Ala Leu Ala Gly Leu Gly Leu Gly Leu Ala Leu Ala Ala
            1145                1150                1155

Leu Ala Gly Leu Tyr Gly Leu Asn Gly Leu Tyr Gly Leu Asn Pro
            1160                1165                1170

Arg Val Ala Leu Leu Glu Val Ala Leu Ala Arg Gly Ala Leu Ala
            1175                1180                1185

Thr His Arg Ser Glu Arg Ala Arg Gly Cys Tyr Ser Leu Glu Gly
            1190                1195                1200

Leu Asn Leu Glu Ser Glu Arg Pro Arg Pro Arg Ser Glu Arg Gly
            1205                1210                1215

Leu Asn Ser Glu Arg Leu Tyr Ser Leu Glu Ala Leu Ala Gly Leu
            1220                1225                1230

Asn Ala Arg Gly Ala Arg Gly Gly Leu Asn Ala Arg Gly Ala Leu
            1235                1240                1245

Ala Ser Glu Arg Leu Glu Ser Glu Arg Ser Glu Arg Ala Leu Ala
            1250                1255                1260

Pro Arg Val Ala Leu Val Ala Leu Leu Glu Val Ala Leu Gly Leu
            1265                1270                1275
```

Tyr Ala   Ser Pro His Ile Ser
    1280              1285

<210> SEQ ID NO 3
<211> LENGTH: 1549
<212> TYPE: DNA
<213> ORGANISM: Homo sapiens

<400> SEQUENCE: 3

| | | | | | |
|---|---|---|---|---|---|
| gctggcgggg | cccggacaga | agatggtgca | gaagaaacca | gccgaacttc | agggtttcca | 60 |
| ccgttcgttc | aagggggcaga | acccttcga | gctggccttc | tccctagacc | agcccgacca | 120 |
| cggagactct | gactttggcc | tgcagtgctc | agcccgccct | gacatgcccg | ccagccagcc | 180 |
| cattgacatc | ccggacgcca | agaagagggg | caagaagaag | aagcgcggcc | gggccaccga | 240 |
| cagcttctcg | ggcaggtttg | aagacgtcta | ccagctgcag | gaagatgtgc | tgggggaggg | 300 |
| cgctcatgcc | cgagtgcaga | cctgcatcaa | cctgatcacc | agccaggagt | acgccgtcaa | 360 |
| gatcattgag | aagcagccag | ccacattcg | gagcaggggtt | ttcagggagg | tggagatgct | 420 |
| gtaccagtgc | cagggacaca | ggaacgtcct | agagctgatt | gagttcttcg | aggaggagga | 480 |
| ccgcttctac | ctggtgttg | agaagatgcg | ggaggctcc | atcctgagcc | acatccacaa | 540 |
| gcgccggcac | ttcaacgagc | tggaggccag | cgtggtggtg | caggacgtgg | ccagcgcctt | 600 |
| ggactttctg | cataacaaag | gcatcgccca | cagggaccta | aagccggaaa | acatcctctg | 660 |
| tgagcaccc | aaccaggtct | ccccgtgaa | gatctgtgac | ttcgacctgg | gcagcggcat | 720 |
| caaactcaac | ggggactgct | ccctatctc | caccccggag | ctgctcactc | cgtgcggctc | 780 |
| ggcggagtac | atggccccgg | agttagtgga | ggccttcagc | gaggaggcta | gcatctacga | 840 |
| caagcgctgc | gacctgtgga | gcctgggcgt | catcttgtat | atcctactca | gcggctaccc | 900 |
| gcccttcgtg | ggccgctgtg | gcagcgactg | cggctgggac | cgcggcgagg | cctgccctgc | 960 |
| ctgccagaac | atgctgtttg | agagcatcca | ggagggcaag | tacgagttcc | ccgacaagga | 1020 |
| ctgggcccac | atctcctgcg | ctgccaaaga | cctcatctcc | aagctgctgg | tccgtgacgc | 1080 |
| caagcagagg | ctgagtgccg | cccaagtcct | gcaacacccc | tgggttcagg | ggtgcgcccc | 1140 |
| ggagaacacc | ttgcccactc | ccatggtcct | gcagaggtgg | gacagtcact | cctcctccc | 1200 |
| tccccacccc | tgtcgcatcc | acgtgcgacc | tggaggactg | gtcagaaccg | ttactgtgaa | 1260 |
| tgagtgaaga | tcctggagga | ccctggcccc | aggccagctc | ccatcgctgg | gggacggtga | 1320 |
| acggccatgt | gttaatgtta | cgatgttttt | aaaagacaaa | aaaaaaaaa | aaacctcaaa | 1380 |
| agtttttta | aagtgggga | aaaacatcca | agcactttaa | ttccaatgta | ccaggtgaac | 1440 |
| tgacggagct | cagaagtttt | cctttacacc | aactgtcaat | gccggaattt | tgtattctgt | 1500 |
| tttgtaaaga | tttaataaaa | gtcaaaaaac | ttgcaaaaaa | aaaaaaaaa | | 1549 |

<210> SEQ ID NO 4
<211> LENGTH: 1143
<212> TYPE: PRT
<213> ORGANISM: Homo sapiens

<400> SEQUENCE: 4

Met Glu Thr Val Ala Leu Gly Leu Asn Leu Tyr Ser Leu Tyr Ser Pro
1               5                   10                  15

Arg Ala Leu Ala Gly Leu Leu Glu Gly Leu Asn Gly Leu Tyr Pro His
                20                  25                  30

Glu His Ile Ser Ala Arg Gly Ser Glu Arg Pro His Glu Leu Tyr Ser
            35                  40                  45

```
Gly Leu Tyr Gly Leu Asn Ala Ser Asn Pro Arg Pro His Glu Gly Leu
            50                  55                  60
Leu Glu Ala Leu Ala Pro His Glu Ser Glu Arg Leu Glu Ala Ser Pro
65                  70                  75                  80
Gly Leu Asn Pro Arg Ala Ser Pro His Ile Ser Gly Leu Tyr Ala Ser
                85                  90                  95
Pro Ser Glu Arg Ala Ser Pro Pro His Glu Gly Leu Tyr Leu Glu Gly
               100                 105                 110
Leu Asn Cys Tyr Ser Ser Glu Arg Ala Leu Ala Ala Arg Gly Pro Arg
               115                 120                 125
Ala Ser Pro Met Glu Thr Pro Arg Ala Leu Ala Ser Glu Arg Gly Leu
               130                 135                 140
Asn Pro Arg Ile Leu Glu Ala Ser Pro Ile Glu Pro Arg Ala Ser Pro
145                 150                 155                 160
Ala Leu Ala Leu Tyr Ser Leu Tyr Ser Ala Arg Gly Gly Leu Tyr Leu
                165                 170                 175
Tyr Ser Leu Tyr Ser Leu Tyr Ser Leu Tyr Ser Ala Arg Gly Gly Leu
                180                 185                 190
Tyr Ala Arg Gly Ala Leu Ala Thr His Arg Ala Ser Pro Ser Glu Arg
                195                 200                 205
Pro His Glu Ser Glu Arg Gly Tyr Ala Arg Gly Pro His Glu Gly Leu
               210                 215                 220
Ala Ser Pro Val Ala Leu Thr Tyr Arg Gly Leu Asn Leu Glu Gly Leu
225                 230                 235                 240
Asn Gly Leu Ala Ser Pro Val Ala Leu Leu Glu Gly Leu Tyr Gly Leu
                245                 250                 255
Gly Leu Tyr Ala Leu Ala His Ile Ser Ala Leu Ala Ala Arg Gly Val
                260                 265                 270
Ala Leu Gly Leu Asn Thr His Arg Cys Tyr Ser Ile Leu Glu Ala Ser
                275                 280                 285
Asn Leu Glu Ile Leu Glu Thr His Arg Ser Glu Arg Gly Leu Asn Gly
                290                 295                 300
Leu Thr Tyr Arg Ala Leu Ala Val Ala Leu Leu Tyr Ser Ile Leu Glu
305                 310                 315                 320
Ile Leu Glu Gly Leu Leu Tyr Ser Gly Leu Asn Pro Arg Gly Leu Tyr
                325                 330                 335
His Ile Ser Ile Leu Glu Ala Arg Gly Ser Glu Arg Ala Arg Gly Val
                340                 345                 350
Ala Leu Pro His Glu Ala Arg Gly Gly Leu Val Ala Leu Gly Leu Met
                355                 360                 365
Glu Thr Leu Glu Thr Tyr Arg Gly Leu Asn Cys Tyr Ser Gly Leu Asn
                370                 375                 380
Gly Leu Tyr His Ile Ser Ala Arg Gly Ala Ser Asn Val Ala Leu Leu
385                 390                 395                 400
Glu Gly Leu Leu Glu Ile Leu Glu Gly Leu Pro His Glu Pro His Glu
                405                 410                 415
Gly Leu Gly Leu Gly Leu Ala Ser Pro Ala Arg Gly Pro His Glu Thr
                420                 425                 430
Tyr Arg Leu Glu Val Ala Leu Pro His Glu Gly Leu Leu Tyr Ser Met
                435                 440                 445
Glu Thr Ala Arg Gly Gly Leu Tyr Gly Leu Tyr Ser Glu Arg Ile Leu
450                 455                 460
```

-continued

```
Glu Leu Glu Ser Glu Arg His Ile Ser Ile Leu Glu His Ile Ser Leu
465                 470                 475                 480

Tyr Ser Ala Arg Gly Ala Arg Gly His Ile Ser Pro His Glu Ala Ser
            485                 490                 495

Asn Gly Leu Leu Glu Gly Leu Ala Leu Ala Ser Glu Arg Val Ala Leu
        500                 505                 510

Val Ala Leu Val Ala Leu Gly Leu Asn Ala Ser Pro Val Ala Leu Ala
        515                 520                 525

Leu Ala Ser Glu Arg Ala Leu Ala Leu Glu Ala Ser Pro Pro His Glu
        530                 535                 540

Leu Glu His Ile Ser Ala Ser Asn Leu Tyr Ser Gly Leu Tyr Ile Leu
545                 550                 555                 560

Glu Ala Leu Ala His Ile Ser Ala Arg Gly Ala Ser Pro Leu Glu Leu
                565                 570                 575

Tyr Ser Pro Arg Gly Leu Ala Ser Asn Ile Leu Glu Leu Glu Cys Tyr
            580                 585                 590

Ser Gly Leu His Ile Ser Arg Ala Ser Asn Gly Leu Asn Val Ala Leu
        595                 600                 605

Ser Glu Arg Pro Arg Val Ala Leu Leu Tyr Ser Ile Leu Glu Cys Tyr
        610                 615                 620

Ser Ala Ser Pro Pro His Glu Ala Ser Pro Leu Glu Gly Leu Tyr Ser
625                 630                 635                 640

Glu Arg Gly Leu Tyr Ile Leu Glu Leu Tyr Ser Leu Glu Ala Ser Asn
                645                 650                 655

Gly Leu Tyr Ala Ser Pro Cys Tyr Ser Ser Glu Arg Pro Arg Ile Leu
            660                 665                 670

Glu Ser Glu Arg Thr His Arg Pro Arg Gly Leu Leu Glu Leu Glu Thr
        675                 680                 685

His Arg Pro Arg Cys Tyr Ser Gly Leu Tyr Ser Glu Arg Ala Leu Ala
        690                 695                 700

Gly Leu Thr Tyr Arg Met Glu Thr Ala Leu Ala Pro Arg Gly Leu Val
705                 710                 715                 720

Ala Leu Val Ala Leu Gly Leu Ala Leu Ala Pro His Glu Ser Glu Arg
            725                 730                 735

Gly Leu Gly Leu Ala Leu Ala Glu Arg Ile Leu Glu Thr Tyr Arg Ala
            740                 745                 750

Ser Pro Leu Tyr Ser Ala Arg Gly Cys Tyr Ser Ala Ser Pro Leu Glu
        755                 760                 765

Thr Arg Pro Ser Glu Arg Leu Glu Gly Leu Tyr Val Ala Leu Ile Leu
770                 775                 780

Glu Leu Glu Thr Tyr Arg Ile Leu Glu Leu Glu Leu Glu Ser Glu Arg
785                 790                 795                 800

Gly Leu Tyr Thr Tyr Arg Pro Arg Pro Arg Pro His Glu Val Ala Leu
            805                 810                 815

Gly Leu Tyr Ala Arg Gly Cys Tyr Ser Gly Leu Tyr Ser Glu Arg Ala
        820                 825                 830

Ser Pro Cys Tyr Ser Gly Leu Tyr Thr Arg Pro Ala Ser Pro Ala Arg
        835                 840                 845

Gly Gly Leu Tyr Gly Leu Ala Leu Ala Cys Tyr Ser Pro Arg Ala Leu
        850                 855                 860

Ala Cys Tyr Ser Gly Leu Asn Ala Ser Asn Met Glu Thr Leu Glu Pro
865                 870                 875                 880

His Glu Gly Leu Ser Glu Arg Ile Leu Glu Gly Leu Asn Gly Leu Gly
```

```
                    885               890              895
Leu Tyr Leu Tyr Ser Thr Tyr Arg Gly Leu Pro His Glu Pro Arg Ala
                900              905              910
Ser Pro Leu Tyr Ser Ala Ser Pro Thr Arg Pro Ala Leu Ala His Ile
            915              920              925
Ser Ile Leu Glu Ser Glu Arg Cys Tyr Ser Ala Leu Ala Ala Leu Ala
        930              935              940
Leu Tyr Ser Ala Ser Pro Leu Glu Ile Leu Glu Ser Glu Arg Leu Tyr
945              950              955              960
Ser Leu Glu Leu Glu Val Ala Leu Ala Arg Gly Ala Ser Pro Ala Leu
                965              970              975
Ala Leu Tyr Ser Gly Leu Asn Ala Arg Gly Leu Glu Ser Glu Arg Ala
                980              985              990
Leu Ala Ala Leu Ala Gly Leu Asn Val Ala Leu Leu Glu Gly Leu Asn
            995              1000             1005
His Ile Ser Pro Arg Thr Arg Pro Val Ala Leu Gly Leu Asn Gly
        1010             1015             1020
Leu Tyr Cys Tyr Ser Ala Leu Ala Pro Arg Gly Leu Ala Ser Asn
        1025             1030             1035
Thr His Arg Leu Glu Pro Arg Thr His Arg Pro Arg Met Glu Thr
        1040             1045             1050
Val Ala Leu Leu Glu Gly Leu Asn Ala Arg Gly Thr Arg Pro Ala
        1055             1060             1065
Ser Pro Ser Glu Arg His Ile Ser Pro His Glu Leu Glu Leu Glu
        1070             1075             1080
Pro Arg Pro Arg His Ile Ser Pro Arg Cys Tyr Ser Ala Arg Gly
        1085             1090             1095
Ile Leu Glu His Ile Ser Val Ala Leu Ala Arg Gly Pro Arg Gly
        1100             1105             1110
Leu Tyr Gly Leu Tyr Leu Glu Val Ala Leu Ala Arg Gly Thr His
        1115             1120             1125
Arg Val Ala Leu Thr His Arg Val Ala Leu Ala Ser Asn Gly Leu
        1130             1135             1140

<210> SEQ ID NO 5
<211> LENGTH: 2745
<212> TYPE: DNA
<213> ORGANISM: Homo sapiens

<400> SEQUENCE: 5
ggcacgaggg cgaccgctcc ccggcgggag ccagcgaagg tttccatgtc agaggccgat    60
ggagaactga agattgccac ctacgcacaa aggccattga cacttcgt gtagctggaa     120 gacaccaact tcctgacagg agctttattt catttgggat ttcaagttta cagatggtat   180
cttctcaaaa gttggaaaaa cctatagaga tgggcagtag cgaaccccctt cccatcgcag   240 atggtgacag gaggaggaag aagaagcgga ggggccgggc cactgactcc ttgccaggaa    300
agtttgaaga tatgtacaag ctgaccctctg aattgcttgg agagggagcc tatgccaaag   360
ttcaaggtgc cgtgagccta cagaatggca aagagtatgc cgtcaaaatc atcgagaaac    420
aagcagggca cagtcggagt agggtgtttc gagaggtgga cgctgtatat cagtgtcagg    480
gaaacaagaa catttggag ctgattgagt tctttgaaga tgacacaagg ttttacttgg     540
tctttgagaa attgcaagga ggttccatct tagcccacat ccagaagcaa aagcacttca    600
atgagcgaga agccagccga gtggtgcggg acgttgctgc tgcccttgac ttcctgcata    660
```

```
ccaaagacaa agtctctctc tgtcacctag gctggagtgc tatggcgcca tcagggctca    720
ctgcagcccc aacctccctg ggctccagtg atcctcccac ctcagcctcc caagtagctg    780
ggactacagg cattgctcat cgtgatctga accagaaaaa tatattgtgt gaatctccag    840
aaaaggtgtc tccagtgaaa atctgtgact ttgacttggg cagtgggatg aaactgaaca    900
actcctgtac ccccataacc acaccagagc tgaccacccc atgtggctct gcagaataca    960
tggcccctga ggtagtggag gtcttcacgg accaggccac attctacgac aagcgctgtg   1020
acctgtggag cctgggcgtg gtcctctaca tcatgctgag tggctaccca ccttcgtgg    1080
gtcactgcgg ggccgactgt ggctgggacc ggggcgaggt ctgcagggtg tgccagaaca   1140
agctgtttga aagcatccag gaaggcaagt atgagtttcc tgacaaggac tgggcacaca   1200
tctccagtga agccaaagac ctcatctcca agctcctggt gcgagatgca aagcagagac   1260
ttagcgccgc ccaagttctg cagcacccat gggtgcaggg gcaagctcca gaaaagggac   1320
tccccacgcc gcaagtcctc cagaggaaca gcagcacaat ggacctgacg ctcttcgcag   1380
ctgaggccat cgcccttaac cgccagctat ctcagcacga agagaacgaa ctagcagagg   1440
agccagaggc actagctgat ggcctctgct ccatgaagct ttcccctccc tgcaagtcac   1500
gcctggcccg gagacgggcc ctggcccagg caggccgtgg tgaagacagg agcccgccca   1560
cagcactctg aaatgctcca gtcacacctt ataggcccta ggcctggcca ggcattgtcc   1620
cctggaaacc tgtgtggcta agtctgctg agcaggcagc agcctctgct ctgtggctcc    1680
attcaggctt tttcatctac gaaggccctg aggttcccat caaccccat ttccctaggg    1740
tcctggagga aaaagctttt tccaaagggg ttgtctttga aaggaaagc aatcacttct    1800
cactttgcat aattgcctgc agcaggaaca tctcttcact gggctccacc tgctcacccg   1860
cctgcagatc tgggatccag cctgctctca ccgctgtagc tgtggcggct ggggctgcag   1920
cctgcaggga gaaggaagaa gcatcagttg acagaggctg ccgacacgtg cctcttccct   1980
ctcttctctg tcaccctcct ctggcggtcc ttccaccttc ctctgtcctc cggatgtcct   2040
cttttgcccgt cttctcccett ggctgagcaa agccatcccc tcaattcagg gaagggcaag   2100
gagccttcct cattcaggaa atcaaatcag tcttccggtc tgcagcacgg aaaagcacat   2160
aatctttctt tgctgtgact gaaatgtatc cctcgtttat catcccctt gtttgtgatt    2220
gctgctaaag tcagtagtat cgttttttta aaaaaaagt ttggtgtttt taaccatgct    2280
gttccagcaa agatgatacc ttaaactccc actgcaagcc catgaacttc ccagagagtg   2340
gaacggcttg ctcttctttc tagaatgtcc atgcacttgg gttttaatca gcagttccct   2400
attattctga ttttaagctg ttcctgtgat gaacttagag acagcatcgg tgtctgctgc   2460
tgtgtcccca ggtcttgtgt gggtggcaca gatctgggca gttagatagt gctctgtgcc   2520
taaggtgaag ccacactagg gtgaagcctc acttccctgt ttgagcaatg cagtgcctgc   2580
tgcccgtgtg catgaaggta cagccattca gataagtgga actattgagt tacataaaga   2640
aaatagattt gcatttgtca ggcagacgtt tatacaacac cacggtgctt ttatacattg   2700
tgcttatttt aataaaactg aaattctaaa aaaaaaaaa aaaaa                    2745
```

<210> SEQ ID NO 6
<211> LENGTH: 1283
<212> TYPE: PRT
<213> ORGANISM: Homo sapiens

<400> SEQUENCE: 6

```
Met Glu Thr Val Ala Leu Ser Glu Arg Ser Glu Arg Gly Leu Asn Leu
1               5                   10                  15

Tyr Ser Leu Glu Gly Leu Leu Tyr Ser Pro Arg Ile Leu Glu Gly Met
            20                  25                  30

Glu Thr Gly Leu Tyr Ser Glu Arg Ser Glu Arg Gly Leu Pro Arg Leu
                35                  40                  45

Glu Pro Arg Ile Leu Glu Ala Leu Ala Ala Ser Pro Gly Leu Tyr Ala
50                  55                  60

Ser Pro Ala Arg Gly Ala Arg Gly Ala Arg Gly Leu Tyr Ser Leu Tyr
65                  70                  75                  80

Ser Leu Tyr Ser Ala Arg Gly Ala Arg Gly Leu Tyr Ala Arg Gly
                85                  90                  95

Ala Leu Ala Thr His Arg Ala Ser Pro Ser Glu Arg Leu Glu Pro Arg
                100                 105                 110

Gly Leu Tyr Leu Tyr Ser Pro His Glu Gly Leu Ala Ser Pro Met Glu
                115                 120                 125

Thr Thr Tyr Arg Leu Tyr Ser Leu Glu Thr His Arg Ser Glu Arg Gly
                130                 135                 140

Leu Leu Glu Leu Glu Gly Leu Tyr Gly Leu Gly Leu Tyr Ala Leu Ala
145                 150                 155                 160

Thr Tyr Arg Ala Leu Ala Leu Tyr Ser Val Ala Leu Gly Leu Asn Gly
                165                 170                 175

Leu Tyr Ala Leu Ala Val Ala Leu Ser Glu Arg Leu Glu Gly Leu Asn
                180                 185                 190

Ala Ser Asn Gly Leu Tyr Leu Tyr Ser Gly Leu Thr Tyr Arg Ala Leu
                195                 200                 205

Ala Val Ala Leu Leu Tyr Ser Ile Leu Glu Ile Leu Glu Gly Leu Leu
                210                 215                 220

Tyr Ser Gly Leu Asn Ala Leu Ala Gly Leu Tyr His Ile Ser Ser Glu
225                 230                 235                 240

Arg Ala Arg Gly Ser Glu Arg Ala Arg Gly Val Ala Leu Pro His Glu
                245                 250                 255

Ala Arg Gly Gly Leu Val Ala Leu Gly Leu Thr His Arg Leu Glu Thr
                260                 265                 270

Tyr Arg Gly Leu Asn Cys Tyr Ser Gly Leu Asn Gly Leu Tyr Ala Ser
                275                 280                 285

Asn Leu Tyr Ser Ala Ser Asn Ile Leu Glu Leu Glu Gly Leu Leu Glu
                290                 295                 300

Ile Leu Glu Gly Leu Pro His Glu Pro His Glu Gly Leu Ala Ser Pro
305                 310                 315                 320

Ala Ser Pro Thr His Arg Ala Arg Gly Pro His Glu Thr Tyr Arg Leu
                325                 330                 335

Glu Val Ala Leu Pro His Glu Gly Leu Leu Tyr Ser Leu Glu Gly Leu
                340                 345                 350

Asn Gly Leu Tyr Gly Leu Tyr Ser Glu Arg Ile Leu Glu Leu Glu Ala
                355                 360                 365

Leu Ala His Ile Ser Ile Leu Glu Gly Leu Asn Leu Tyr Ser Gly Leu
                370                 375                 380

Asn Leu Tyr Ser His Ile Ser Pro His Glu Ala Ser Asn Gly Leu Ala
385                 390                 395                 400

Arg Gly Gly Leu Ala Leu Ala Ser Glu Arg Ala Arg Gly Val Ala Leu
                405                 410                 415

Val Ala Leu Ala Arg Gly Ala Ser Pro Val Ala Leu Ala Leu Ala Ala
```

```
                420                425                430
Leu Ala Ala Leu Ala Leu Glu Ala Ser Pro Pro His Glu Leu Glu His
            435                440                445
Ile Ser Thr His Arg Leu Tyr Ser Ala Ser Pro Leu Tyr Ser Val Ala
            450                455                460
Leu Ser Glu Arg Leu Glu Cys Tyr Ser His Ile Ser Leu Glu Gly Leu
465                470                475                480
Tyr Thr Arg Pro Ser Glu Arg Ala Leu Ala Met Glu Thr Ala Leu Ala
            485                490                495
Pro Arg Ser Glu Arg Gly Leu Tyr Leu Glu Thr His Arg Ala Leu Ala
            500                505                510
Ala Leu Ala Pro Arg Thr His Arg Ser Glu Arg Leu Glu Gly Leu Tyr
            515                520                525
Ser Glu Arg Ser Glu Arg Ala Ser Pro Pro Arg Pro Arg Thr His Arg
            530                535                540
Ser Glu Arg Ala Leu Ala Ser Glu Arg Gly Leu Asn Val Ala Leu Ala
545                550                555                560
Leu Ala Gly Leu Tyr Thr His Arg Thr His Arg Gly Leu Tyr Ile Leu
            565                570                575
Glu Ala Leu Ala His Ile Ser Ala Arg Gly Ala Ser Pro Leu Glu Leu
            580                585                590
Tyr Ser Pro Arg Gly Leu Ala Ser Asn Ile Leu Glu Leu Glu Cys Tyr
            595                600                605
Ser Gly Leu Ser Glu Arg Pro Arg Gly Leu Leu Tyr Ser Val Ala Leu
            610                615                620
Ser Glu Arg Pro Arg Val Ala Leu Leu Tyr Ser Ile Leu Glu Cys Tyr
625                630                635                640
Ser Ala Ser Pro Pro His Glu Ala Ser Pro Leu Glu Gly Leu Tyr Ser
            645                650                655
Glu Arg Gly Leu Tyr Met Glu Thr Leu Tyr Ser Leu Glu Ala Ser Asn
            660                665                670
Ala Ser Asn Ser Glu Arg Cys Tyr Ser Thr His Arg Pro Arg Ile Leu
            675                680                685
Glu Thr His Arg Thr His Arg Pro Arg Gly Leu Leu Glu Thr His Arg
            690                695                700
Thr His Arg Pro Arg Cys Tyr Ser Gly Leu Tyr Ser Glu Arg Ala Leu
705                710                715                720
Ala Gly Leu Thr Tyr Arg Met Glu Thr Ala Leu Ala Pro Arg Gly Leu
            725                730                735
Val Ala Leu Val Ala Leu Gly Leu Val Ala Leu Pro His Glu Thr His
            740                745                750
Arg Ala Ser Pro Gly Leu Asn Ala Leu Ala Thr His Arg Pro His Glu
            755                760                765
Thr Tyr Arg Ala Ser Pro Leu Tyr Ser Ala Arg Gly Cys Tyr Ser Ala
            770                775                780
Ser Pro Leu Glu Thr Arg Pro Ser Glu Arg Leu Glu Gly Leu Tyr Val
785                790                795                800
Ala Leu Val Ala Leu Leu Glu Thr Tyr Arg Ile Leu Glu Met Glu Thr
            805                810                815
Leu Glu Ser Glu Arg Gly Leu Tyr Thr Tyr Arg Pro Arg Pro Arg Pro
            820                825                830
His Glu Val Ala Leu Gly Leu Tyr His Ile Ser Cys Tyr Ser Gly Leu
            835                840                845
```

-continued

```
Tyr Ala Leu Ala Ala Ser Pro Cys Tyr Ser Gly Leu Tyr Thr Arg Pro
850                 855                 860

Ala Ser Pro Ala Arg Gly Gly Leu Tyr Gly Leu Val Ala Leu Cys Tyr
865                 870                 875                 880

Ser Ala Arg Gly Val Ala Leu Cys Tyr Ser Gly Leu Asn Ala Ser Asn
                885                 890                 895

Leu Tyr Ser Leu Glu Pro His Glu Gly Leu Ser Glu Arg Ile Leu Glu
            900                 905                 910

Gly Leu Asn Gly Leu Gly Leu Tyr Leu Tyr Ser Thr Tyr Arg Gly Leu
                915                 920                 925

Pro His Glu Pro Arg Ala Ser Pro Leu Tyr Ser Ala Ser Pro Thr Arg
930                 935                 940

Pro Ala Leu Ala His Ile Ser Ile Leu Glu Ser Glu Arg Ser Glu Arg
945                 950                 955                 960

Gly Leu Ala Leu Ala Leu Tyr Ser Ala Ser Pro Leu Glu Ile Leu Glu
                965                 970                 975

Ser Glu Arg Leu Tyr Ser Leu Glu Leu Glu Val Ala Leu Ala Arg Gly
            980                 985                 990

Ala Ser Pro Ala Leu Ala Leu Tyr Ser Gly Leu Asn Ala Arg Gly Leu
            995                 1000                1005

Glu Ser Glu Arg Ala Leu Ala Ala Leu Ala Gly Leu Asn Val Ala
        1010                1015                1020

Leu Leu Glu Gly Leu Asn His Ile Ser Pro Arg Thr Arg Pro Val
        1025                1030                1035

Ala Leu Gly Leu Asn Gly Leu Tyr Gly Leu Asn Ala Leu Ala Pro
        1040                1045                1050

Arg Gly Leu Leu Tyr Ser Gly Leu Tyr Leu Glu Pro Arg Thr His
        1055                1060                1065

Arg Pro Arg Gly Leu Asn Val Ala Leu Leu Glu Gly Leu Asn Ala
        1070                1075                1080

Arg Gly Ala Ser Asn Ser Glu Arg Ser Glu Arg Thr His Arg Met
        1085                1090                1095

Glu Thr Ala Ser Pro Leu Glu Thr His Arg Leu Glu Pro His Glu
        1100                1105                1110

Ala Leu Ala Ala Leu Ala Gly Leu Ala Leu Ala Ile Leu Glu Ala
        1115                1120                1125

Leu Ala Leu Glu Ala Ser Asn Ala Arg Gly Gly Leu Asn Leu Glu
        1130                1135                1140

Ser Glu Arg Gly Leu Asn His Ile Ser Gly Leu Gly Leu Ala Ser
        1145                1150                1155

Asn Gly Leu Leu Glu Ala Leu Ala Gly Leu Gly Leu Pro Arg Gly
        1160                1165                1170

Leu Ala Leu Ala Leu Glu Ala Leu Ala Ala Ser Pro Gly Leu Tyr
        1175                1180                1185

Leu Glu Cys Tyr Ser Ser Glu Arg Met Glu Thr Leu Tyr Ser Leu
        1190                1195                1200

Glu Ser Glu Arg Pro Arg Pro Arg Cys Tyr Ser Leu Tyr Ser Ser
        1205                1210                1215

Glu Arg Ala Arg Gly Leu Glu Ala Leu Ala Ala Arg Gly Ala Arg
        1220                1225                1230

Gly Ala Arg Gly Ala Leu Ala Leu Glu Ala Leu Ala Gly Leu Asn
        1235                1240                1245
```

-continued

```
Ala Leu Ala Gly Leu Tyr Ala Arg Gly Gly Leu Tyr Gly Leu Ala
    1250                1255                1260

Ser Pro Ala Arg Gly Ser Glu Arg Pro Arg Pro Arg Thr His Arg
    1265                1270                1275

Ala Leu Ala Leu Glu
    1280

<210> SEQ ID NO 7
<211> LENGTH: 1253
<212> TYPE: DNA
<213> ORGANISM: Drosophila melanogaster
<220> FEATURE:
<221> NAME/KEY: misc_feature
<222> LOCATION: (5)..(5)
<223> OTHER INFORMATION: n is a, c, g, or t

<400> SEQUENCE: 7
cgagnaagtg ttactatcta aacacatttc aaacaattct taacaaacaa ttccaaacat      60
acaattccac ttaccactta ccgaccaaat tacgagttta caatggacaa agctgaacgc     120
gactactggc atcttcgatc cttggaaatc gaagaggagc cgcgatttcc gccaacaaac     180
gtcgctgatc cactaaccgc acgcaatctg ttccagctct acgtcaacac cttcattgga     240
gccaatctgg ccgagtcgtg tgttttccca ttggacgtgg ccaagacccg gatgcaggta     300
gatggcgagc aggccaagaa gacgggtaaa gcgatgccaa ctttccgtgc aactcttacc     360
aacatgatcc gagtggaggg attcaagtcg ctctacgccg gcttctcggc aatggtgacc     420
cgaaacttta tcttcaactc gttacgtgtt gttctctacg acgttttccg gcgccctttt     480
ctctaccaga acgaacggaa cgaggaagtg ctcaagatct catggcgcgt gggatgcagc     540
ttcaccgcag gctgcattgc ccaggcactg gccaatccct tgacatcgt caaggtgcga     600 atgcagacgg aaggacgccg ccgccagctg ggctatgatg tgcgggtgaa cagcatggtg     660
caggccttcg tggacatcta ccgccgtggc ggactgccca gtatgtggaa gggtgtaggg     720
cccagctgca tgcgtgcctg cctgatgacg accggcgatg tgggcagtta cgatatcagt     780
aagcgcacct tcaagcgcct gctggacttg gaggaaggcc tgccactgcg tttcgtgtct     840
tccatgtgcg ccggactaac ggcatccgtg ctcagcacgc cggcgaacgt gatcaagtcg     900
cggatgatga accagccggt gaacgagagc ggcaagaatc tgtactacaa gaactccctc     960
gactgcatta ggaagctggt cagggaggag ggtgtcctca cgttgtataa gggcctcatg    1020
cccacttggt ttcgcctggg accgttctca gtgctctttt ggctgtccgt cgagcagctg    1080
cgtcagtgga aaggccagag tggattttag gagcaaacta tcaatcttac tatcgtattt    1140
tgtatgtctt ttaacacgca ataaaaaggg tgcaagtcaa accatctatt atacatatta    1200
taaatataac tttaatccca aaaaaaaaaa aaaaaactcg tgccgaattc gat            1253

<210> SEQ ID NO 8
<211> LENGTH: 937
<212> TYPE: PRT
<213> ORGANISM: Drosophila melanogaster

<400> SEQUENCE: 8

Met Glu Thr Ala Ser Pro Leu Tyr Ser Ala Leu Ala Gly Leu Ala Arg
1               5                   10                  15

Gly Ala Ser Pro Thr Tyr Arg Thr Arg Pro His Ile Ser Leu Glu Ala
            20                  25                  30

Arg Gly Ser Glu Arg Leu Glu Gly Leu Ile Leu Glu Gly Leu Gly Leu
        35                  40                  45
```

```
Gly Leu Pro Arg Ala Arg Gly Pro His Glu Pro Arg Pro Arg Thr His
         50                  55                  60
Arg Ala Ser Asn Val Ala Leu Ala Leu Ala Ala Ser Pro Pro Arg Leu
 65                  70                  75                  80
Glu Thr His Arg Ala Leu Ala Ala Arg Gly Ala Ser Asn Leu Glu Pro
                 85                  90                  95
His Glu Gly Leu Asn Leu Glu Thr Tyr Arg Val Ala Leu Ala Ser Asn
             100                 105                 110
Thr His Arg Pro His Glu Ile Leu Glu Gly Leu Tyr Ala Leu Ala Ala
             115                 120                 125
Ser Asn Leu Glu Ala Leu Ala Gly Leu Ser Glu Arg Cys Tyr Ser Val
130                 135                 140
Ala Leu Pro His Glu Pro Arg Leu Glu Ala Ser Pro Val Ala Leu Ala
145                 150                 155                 160
Leu Ala Leu Tyr Ser Thr His Arg Ala Arg Gly Met Glu Thr Gly Leu
                 165                 170                 175
Asn Val Ala Leu Ala Ser Pro Gly Leu Tyr Gly Leu Gly Leu Asn Ala
                 180                 185                 190
Leu Ala Leu Tyr Ser Leu Tyr Ser Thr His Arg Gly Leu Tyr Leu Tyr
                 195                 200                 205
Ser Ala Leu Ala Met Glu Thr Pro Arg Thr His Arg Pro His Glu Ala
210                 215                 220
Arg Gly Ala Leu Ala Thr His Arg Leu Glu Thr His Arg Ala Ser Asn
225                 230                 235                 240
Met Glu Thr Ile Leu Glu Ala Arg Gly Val Ala Leu Gly Leu Gly Leu
                 245                 250                 255
Tyr Pro His Glu Leu Tyr Ser Ser Glu Arg Leu Glu Thr Tyr Arg Ala
                 260                 265                 270
Leu Ala Gly Leu Tyr Pro His Glu Ser Glu Arg Ala Leu Ala Met Glu
                 275                 280                 285
Thr Val Ala Leu Thr His Arg Ala Arg Gly Ala Ser Asn Pro His Glu
                 290                 295                 300
Ile Leu Glu Pro His Glu Ala Ser Asn Ser Glu Arg Leu Glu Ala Arg
305                 310                 315                 320
Gly Val Ala Leu Val Ala Leu Leu Glu Thr Tyr Arg Ala Ser Pro Val
                 325                 330                 335
Ala Leu Pro His Glu Ala Arg Gly Ala Arg Gly Pro Arg Pro His Glu
                 340                 345                 350
Leu Glu Thr Tyr Arg Gly Leu Asn Ala Ser Asn Gly Leu Ala Arg Gly
                 355                 360                 365
Ala Ser Asn Gly Leu Gly Leu Val Ala Leu Leu Glu Leu Tyr Ser Ile
370                 375                 380
Leu Glu Thr Tyr Arg Met Glu Thr Ala Leu Ala Leu Glu Gly Leu Tyr
385                 390                 395                 400
Cys Tyr Ser Ser Glu Arg Pro His Glu Thr His Arg Ala Leu Ala Gly
                 405                 410                 415
Leu Tyr Cys Tyr Ser Ile Leu Glu Ala Leu Ala Gly Leu Asn Ala Leu
                 420                 425                 430
Ala Leu Glu Ala Leu Ala Ala Ser Asn Pro Arg Pro His Glu Ala Ser
                 435                 440                 445
Pro Ile Leu Glu Val Ala Leu Leu Tyr Ser Val Ala Leu Ala Arg Gly
450                 455                 460
```

```
Met Glu Thr Gly Leu Asn Thr His Arg Gly Leu Gly Leu Tyr Ala Arg
465                 470                 475                 480

Gly Ala Arg Gly Ala Arg Gly Gly Leu Asn Leu Glu Gly Leu Tyr Thr
                485                 490                 495

Tyr Arg Ala Ser Pro Val Ala Leu Ala Arg Gly Val Ala Leu Ala Ser
                500                 505                 510

Asn Ser Glu Arg Met Glu Thr Val Ala Leu Gly Leu Asn Ala Leu Ala
            515                 520                 525

Pro His Glu Val Ala Leu Ala Ser Pro Ile Leu Glu Thr Tyr Arg Ala
        530                 535                 540

Arg Gly Ala Arg Gly Gly Leu Tyr Gly Leu Tyr Leu Glu Pro Arg Ser
545                 550                 555                 560

Glu Arg Met Glu Thr Thr Arg Pro Leu Tyr Ser Gly Leu Tyr Val Ala
                565                 570                 575

Leu Gly Leu Tyr Pro Arg Ser Glu Arg Cys Tyr Ser Met Glu Thr Ala
                580                 585                 590

Arg Gly Ala Leu Ala Cys Tyr Ser Leu Glu Met Glu Thr Thr His Arg
            595                 600                 605

Thr His Arg Gly Leu Tyr Ala Ser Pro Val Ala Leu Gly Leu Tyr Ser
        610                 615                 620

Glu Arg Thr Tyr Arg Ala Ser Pro Ile Leu Glu Ser Glu Arg Leu Tyr
625                 630                 635                 640

Ser Ala Arg Gly Thr His Arg Pro His Glu Leu Tyr Ser Ala Arg Gly
                645                 650                 655

Leu Glu Leu Glu Ala Ser Pro Leu Glu Gly Leu Gly Leu Gly Leu Tyr
            660                 665                 670

Leu Glu Pro Arg Leu Glu Ala Arg Gly Pro His Glu Val Ala Leu Ser
        675                 680                 685

Glu Arg Ser Glu Arg Met Glu Thr Cys Tyr Ser Ala Leu Ala Gly Leu
        690                 695                 700

Tyr Leu Glu Thr His Arg Ala Leu Ala Ser Glu Arg Val Ala Leu Leu
705                 710                 715                 720

Glu Ser Glu Arg Thr His Arg Pro Arg Ala Leu Ala Ala Ser Asn Val
                725                 730                 735

Ala Leu Ile Leu Glu Leu Tyr Ser Ser Glu Arg Ala Arg Gly Met Glu
            740                 745                 750

Thr Met Glu Thr Ala Ser Asn Gly Leu Asn Pro Arg Val Ala Leu Ala
        755                 760                 765

Ser Asn Gly Leu Ser Glu Arg Gly Leu Tyr Leu Tyr Ser Ala Ser Asn
    770                 775                 780

Leu Glu Thr Tyr Arg Thr Tyr Arg Leu Tyr Ser Ala Ser Asn Ser Glu
785                 790                 795                 800

Arg Leu Glu Ala Ser Pro Cys Tyr Ser Ile Leu Glu Ala Arg Gly Leu
                805                 810                 815

Tyr Ser Leu Glu Val Ala Leu Ala Arg Gly Gly Leu Gly Leu Gly Leu
            820                 825                 830

Tyr Val Ala Leu Leu Glu Thr His Arg Leu Glu Thr Tyr Arg Leu Tyr
        835                 840                 845

Ser Gly Leu Tyr Leu Glu Met Glu Thr Pro Arg Thr His Arg Thr Arg
        850                 855                 860

Pro Pro His Glu Ala Arg Gly Leu Glu Gly Leu Tyr Pro Arg Pro His
865                 870                 875                 880

Glu Ser Glu Arg Val Ala Leu Leu Glu Pro His Glu Thr Arg Pro Leu
```

```
                      885               890                895
Glu Ser Glu Arg Val Ala Leu Gly Leu Gly Leu Asn Leu Glu Ala Arg
            900                 905                 910

Gly Gly Leu Asn Thr Arg Pro Leu Tyr Ser Gly Leu Tyr Gly Leu Asn
        915                 920                 925

Ser Glu Arg Gly Leu Tyr Pro His Glu
    930                 935

<210> SEQ ID NO 9
<211> LENGTH: 24
<212> TYPE: DNA
<213> ORGANISM: Drosophila melanogaster

<400> SEQUENCE: 9
ctaaacaaac aattccaaac atag                                          24

<210> SEQ ID NO 10
<211> LENGTH: 24
<212> TYPE: DNA
<213> ORGANISM: Drosophila melanogaster

<400> SEQUENCE: 10
aaaagacata gaaaatacga tagt                                          24

<210> SEQ ID NO 11
<211> LENGTH: 18
<212> TYPE: DNA
<213> ORGANISM: Mus musculus

<400> SEQUENCE: 11
gctgagggcc tctgctcc                                                 18

<210> SEQ ID NO 12
<211> LENGTH: 16
<212> TYPE: DNA
<213> ORGANISM: Mus musculus

<400> SEQUENCE: 12
tcgccttcga gccagg                                                   16

<210> SEQ ID NO 13
<211> LENGTH: 27
<212> TYPE: DNA
<213> ORGANISM: Mus musculus

<400> SEQUENCE: 13
tgaagctgtc ccctccatcc aaatctc                                       27

<210> SEQ ID NO 14
<211> LENGTH: 19
<212> TYPE: DNA
<213> ORGANISM: Mus musculus

<400> SEQUENCE: 14
tgcacttgat tgaccccga                                                19

<210> SEQ ID NO 15
<211> LENGTH: 22
<212> TYPE: DNA
<213> ORGANISM: Mus musculus

<400> SEQUENCE: 15
```
tttctgattg tcaaccctcc aa                                              22

<210> SEQ ID NO 16
<211> LENGTH: 24
<212> TYPE: DNA
<213> ORGANISM: Mus musculus

<400> SEQUENCE: 16
ccccatcatc cacctgcagt gtcc                                            24

<210> SEQ ID NO 17
<211> LENGTH: 23
<212> TYPE: DNA
<213> ORGANISM: Homo sapiens

<400> SEQUENCE: 17
ccatctcccc ctctgtacat agg                                             23

<210> SEQ ID NO 18
<211> LENGTH: 19
<212> TYPE: DNA
<213> ORGANISM: Homo sapiens

<400> SEQUENCE: 18
ccggctggcg atagcttaa                                                  19

<210> SEQ ID NO 19
<211> LENGTH: 26
<212> TYPE: DNA
<213> ORGANISM: Homo sapiens

<400> SEQUENCE: 19
cacccgtccc ccaatcaaat taaagg                                          26

<210> SEQ ID NO 20
<211> LENGTH: 26
<212> TYPE: DNA
<213> ORGANISM: Homo sapiens

<400> SEQUENCE: 20
ttactgtgaa tgagtgaaga tcctgg                                          26

<210> SEQ ID NO 21
<211> LENGTH: 16
<212> TYPE: DNA
<213> ORGANISM: Homo sapiens

<400> SEQUENCE: 21
atggcgttca ccgtcc                                                     16

<210> SEQ ID NO 22
<211> LENGTH: 21
<212> TYPE: DNA
<213> ORGANISM: Homo sapiens

<400> SEQUENCE: 22
ccaggccagc tcccatcgct g                                               21

<210> SEQ ID NO 23
<211> LENGTH: 21
<212> TYPE: DNA
<213> ORGANISM: Mus musculus

<400> SEQUENCE: 23
aagttggcct tcgcgttaga c                                              21

<210> SEQ ID NO 24
<211> LENGTH: 20
<212> TYPE: DNA
<213> ORGANISM: Mus musculus

<400> SEQUENCE: 24
cgatatgtac aaggagctag                                                20

<210> SEQ ID NO 25
<211> LENGTH: 44
<212> TYPE: DNA
<213> ORGANISM: Mus musculus

<400> SEQUENCE: 25
ctcccccatc tccgcaccag agctgctcgc cccgtgtggg tcag                     44

<210> SEQ ID NO 26
<211> LENGTH: 41
<212> TYPE: DNA
<213> ORGANISM: Mus musculus

<400> SEQUENCE: 26
ctgacccaca cggggcgagc tctggtgcgg agatggggga g                        41

<210> SEQ ID NO 27
<211> LENGTH: 19
<212> TYPE: DNA
<213> ORGANISM: Mus musculus

<400> SEQUENCE: 27
gctgctggtc cgagatgcc                                                 19

<210> SEQ ID NO 28
<211> LENGTH: 18
<212> TYPE: DNA
<213> ORGANISM: Mus musculus

<400> SEQUENCE: 28
gggtcatgcg cgatcccc                                                  18

<210> SEQ ID NO 29
<211> LENGTH: 22
<212> TYPE: DNA
<213> ORGANISM: Mus musculus

<400> SEQUENCE: 29
cagcgtggta gtacaggacg tg                                             22

<210> SEQ ID NO 30
<211> LENGTH: 16
<212> TYPE: DNA
<213> ORGANISM: Mus musculus

<400> SEQUENCE: 30
tccctgtggg cgatgc                                                    16

<210> SEQ ID NO 31
<211> LENGTH: 28
<212> TYPE: DNA
<213> ORGANISM: Mus musculus -continued

```
<400> SEQUENCE: 31
cagtgccctg gacttccctg cataacaa                                         28

<210> SEQ ID NO 32
<211> LENGTH: 19
<212> TYPE: DNA
<213> ORGANISM: Mus musculus

<400> SEQUENCE: 32
acatcagccc acagtgtga                                                   19

<210> SEQ ID NO 33
<211> LENGTH: 21
<212> TYPE: DNA
<213> ORGANISM: Mus musculus

<400> SEQUENCE: 33
tctccattga gtttgatacc a                                                21

<210> SEQ ID NO 34
<211> LENGTH: 27
<212> TYPE: DNA
<213> ORGANISM: Mus musculus

<400> SEQUENCE: 34
cggaatccac tagctccttg tacatat                                          27

<210> SEQ ID NO 35
<211> LENGTH: 29
<212> TYPE: DNA
<213> ORGANISM: Mus musculus

<400> SEQUENCE: 35
ccatcgatgg aactcgtatt gcatagtag                                        29

<210> SEQ ID NO 36
<211> LENGTH: 23
<212> TYPE: DNA
<213> ORGANISM: Mus musculus

<400> SEQUENCE: 36
agactaggga ggagggtgga gga                                              23

<210> SEQ ID NO 37
<211> LENGTH: 22
<212> TYPE: DNA
<213> ORGANISM: Mus musculus

<400> SEQUENCE: 37
ggtggatgtg gaatgtgtgc ga                                               22

<210> SEQ ID NO 38
<211> LENGTH: 21
<212> TYPE: DNA
<213> ORGANISM: Mus musculus

<400> SEQUENCE: 38
ggggtgtagg ggtctgttag g                                                21

<210> SEQ ID NO 39
<211> LENGTH: 1166
<212> TYPE: PRT
<213> ORGANISM: Homo sapiens
```

<400> SEQUENCE: 39

```
Met Glu Thr Val Ala Leu Ser Glu Arg Ser Glu Arg Gly Leu Asn Leu
1               5                   10                  15

Tyr Ser Leu Glu Gly Leu Leu Tyr Ser Pro Arg Ile Leu Glu Gly Leu
                20                  25                  30

Met Glu Thr Gly Leu Tyr Ser Glu Arg Ser Glu Arg Gly Pro Arg Leu
                35                  40                  45

Glu Pro Arg Ile Leu Glu Ala Leu Ala Ala Ser Pro Gly Leu Tyr Ala
            50                  55                  60

Ser Pro Ala Arg Gly Ala Arg Gly Ala Arg Gly Leu Tyr Ser Leu Tyr
65                  70                  75                  80

Ser Leu Tyr Ser Ala Arg Gly Ala Arg Gly Gly Leu Tyr Ala Arg Gly
                85                  90                  95

Ala Leu Ala Thr His Arg Ala Ser Pro Ser Glu Arg Leu Glu Pro Arg
                100                 105                 110

Gly Leu Tyr Leu Tyr Ser Pro His Glu Gly Leu Ala Ser Pro Met Glu
                115                 120                 125

Thr Thr Tyr Arg Leu Tyr Ser Leu Glu Thr His Arg Ser Glu Arg Gly
                130                 135                 140

Leu Leu Glu Leu Glu Gly Leu Tyr Gly Leu Gly Leu Tyr Ala Leu Ala
145                 150                 155                 160

Thr Tyr Arg Ala Leu Ala Leu Tyr Ser Val Ala Leu Gly Leu Asn Gly
                165                 170                 175

Leu Tyr Ala Leu Ala Val Ala Leu Ser Glu Arg Leu Glu Gly Leu Asn
                180                 185                 190

Ala Ser Asn Gly Leu Tyr Leu Tyr Ser Gly Leu Thr Tyr Arg Ala Leu
                195                 200                 205

Ala Val Ala Leu Leu Tyr Ser Ile Leu Glu Ile Leu Glu Gly Leu Leu
                210                 215                 220

Tyr Ser Gly Leu Asn Ala Leu Ala Gly Leu Tyr His Ile Ser Ser Glu
225                 230                 235                 240

Arg Ala Arg Gly Ser Glu Arg Ala Arg Gly Val Ala Leu Pro His Glu
                245                 250                 255

Ala Arg Gly Gly Leu Val Ala Leu Gly Leu Thr His Arg Leu Glu Thr
                260                 265                 270

Tyr Arg Gly Leu Asn Cys Tyr Ser Gly Leu Asn Gly Leu Tyr Ala Ser
                275                 280                 285

Asn Leu Tyr Ser Ala Ser Asn Ile Leu Glu Leu Glu Gly Leu Leu Glu
                290                 295                 300

Ile Leu Glu Gly Leu Pro His Glu Pro His Glu Gly Leu Ala Ser Pro
305                 310                 315                 320

Ala Ser Pro Thr His Arg Ala Arg Gly Pro His Glu Thr Tyr Arg Leu
                325                 330                 335

Glu Val Ala Leu Pro His Glu Gly Leu Tyr Ser Leu Glu Gly Leu Asn
                340                 345                 350

Gly Leu Tyr Gly Leu Tyr Ser Glu Arg Ile Glu Leu Glu Ala Leu Ala
                355                 360                 365

His Ile Ser Ile Leu Glu Gly Leu Asn Leu Tyr Ser Gly Leu Asn Leu
                370                 375                 380

Tyr Ser His Ile Ser Pro His Glu Ala Ser Asn Gly Leu Ala Arg Gly
385                 390                 395                 400

Gly Leu Ala Leu Ala Ser Glu Arg Ala Arg Gly Val Ala Leu Val Ala
```

```
                     405                 410                 415
Leu Ala Arg Gly Ala Ser Pro Val Ala Leu Ala Ala Leu Ala
                420                 425                 430
Ala Leu Ala Leu Glu Ala Ser Pro Pro His Glu Leu Glu His Ile Ser
                435                 440                 445
Thr His Arg Leu Tyr Ser Gly Leu Tyr Ile Leu Glu Ala Leu Ala His
    450                 455                 460
Ile Ser Ala Arg Gly Ala Ser Pro Leu Glu Leu Tyr Ser Pro Arg Gly
465                 470                 475                 480
Leu Ala Ser Asn Ile Leu Glu Leu Glu Cys Tyr Ser Gly Leu Ser Glu
                485                 490                 495
Arg Pro Arg Gly Leu Leu Tyr Ser Val Ala Leu Ser Glu Arg Pro Arg
                500                 505                 510
Val Ala Leu Leu Tyr Ser Ile Leu Glu Cys Tyr Ser Ala Ser Pro Pro
                515                 520                 525
His Glu Ala Ser Pro Leu Glu Gly Leu Tyr Ser Glu Arg Gly Leu Tyr
                530                 535                 540
Met Glu Thr Leu Tyr Ser Leu Glu Ala Ser Asn Ala Ser Asn Ser Glu
545                 550                 555                 560
Arg Cys Tyr Ser Thr His Arg Pro Arg Ile Leu Glu Thr His Arg Thr
                565                 570                 575
His Arg Pro Arg Gly Leu Leu Glu Thr His Arg Thr His Arg Pro Arg
                580                 585                 590
Cys Tyr Ser Gly Leu Tyr Ser Glu Arg Ala Leu Ala Gly Leu Thr Tyr
                595                 600                 605
Arg Met Glu Thr Ala Leu Ala Pro Arg Gly Leu Val Ala Leu Val Ala
                610                 615                 620
Leu Gly Leu Val Ala Leu Pro His Glu Thr His Arg Ala Ser Pro Gly
625                 630                 635                 640
Leu Asn Ala Leu Ala Thr His Arg Pro His Glu Thr Tyr Arg Ala Ser
                645                 650                 655
Pro Leu Tyr Ser Ala Arg Gly Cys Tyr Ser Ala Ser Pro Leu Glu Thr
                660                 665                 670
Arg Pro Ser Glu Arg Leu Glu Gly Leu Tyr Val Ala Leu Val Ala Leu
                675                 680                 685
Leu Glu Thr Tyr Arg Ile Leu Glu Met Glu Thr Leu Glu Ser Glu Arg
                690                 695                 700
Gly Leu Tyr Thr Tyr Arg Pro Arg Pro Arg Pro His Glu Val Ala Leu
705                 710                 715                 720
Gly Leu Tyr His Ile Ser Cys Tyr Ser Gly Leu Tyr Ala Leu Ala Ala
                725                 730                 735
Ser Pro Cys Tyr Ser Gly Leu Tyr Thr Arg Pro Ala Ser Pro Ala Arg
                740                 745                 750
Gly Gly Leu Tyr Gly Leu Val Ala Leu Cys Tyr Ser Ala Arg Gly Val
                755                 760                 765
Ala Leu Cys Tyr Ser Gly Leu Asn Ala Ser Asn Leu Tyr Ser Leu Glu
                770                 775                 780
Pro His Glu Gly Leu Ser Glu Arg Ile Leu Glu Gly Leu Asn Gly Leu
785                 790                 795                 800
Gly Leu Tyr Leu Tyr Ser Thr Tyr Arg Gly Leu Pro His Glu Pro Arg
                805                 810                 815
Ala Ser Pro Leu Tyr Ser Ala Ser Pro Thr Arg Pro Ala Leu Ala His
                820                 825                 830
```

```
Ile Ser Ile Leu Glu Ser Glu Arg Ser Glu Arg Gly Leu Ala Leu Ala
        835                 840                 845

Leu Tyr Ser Ala Ser Pro Leu Glu Ile Leu Glu Ser Glu Arg Leu Tyr
    850                 855                 860

Ser Leu Glu Leu Glu Val Ala Leu Ala Arg Gly Ala Ser Pro Ala Leu
865                 870                 875                 880

Ala Leu Tyr Ser Gly Leu Asn Ala Arg Gly Leu Glu Ser Glu Arg Ala
                885                 890                 895

Leu Ala Ala Leu Ala Gly Leu Asn Val Ala Leu Leu Glu Gly Leu Asn
                900                 905                 910

His Ile Ser Pro Arg Thr Arg Pro Val Ala Leu Gly Leu Asn Gly Leu
                915                 920                 925

Tyr Gly Leu Asn Ala Leu Ala Pro Arg Gly Leu Leu Tyr Ser Gly Leu
            930                 935                 940

Tyr Leu Glu Pro Arg Thr His Arg Pro Arg Gly Leu Asn Val Ala Leu
945                 950                 955                 960

Leu Glu Gly Leu Asn Ala Arg Gly Ala Ser Asn Ser Glu Arg Ser Glu
                965                 970                 975

Arg Thr His Arg Met Glu Thr Ala Ser Pro Leu Glu Thr His Arg Leu
            980                 985                 990

Glu Pro His Glu Ala Leu Ala Ala Leu Ala Gly Leu Ala Leu Ala Ile
            995                 1000                1005

Leu Glu Ala Leu Ala Leu Glu Ala Ser Asn Ala Arg Gly Gly Leu
        1010            1015            1020

Asn Leu Glu Ser Glu Arg Gly Leu Asn His Ile Ser Gly Leu Gly
        1025            1030            1035

Leu Ala Ser Asn Gly Leu Leu Glu Ala Leu Ala Gly Leu Gly Leu
        1040            1045            1050

Pro Arg Gly Leu Ala Leu Ala Leu Glu Ala Leu Ala Ala Ser Pro
        1055            1060            1065

Gly Leu Tyr Leu Glu Cys Tyr Ser Ser Glu Arg Met Glu Thr Leu
        1070            1075            1080

Tyr Ser Leu Glu Ser Glu Arg Pro Arg Pro Arg Cys Tyr Ser Leu
        1085            1090            1095

Tyr Ser Ser Glu Arg Ala Arg Gly Leu Glu Ala Leu Ala Ala Arg
        1100            1105            1110

Gly Ala Arg Gly Ala Arg Gly Ala Leu Ala Leu Glu Ala Leu Ala
        1115            1120            1125

Gly Leu Asn Ala Leu Ala Gly Leu Tyr Ala Arg Gly Gly Leu Tyr
        1130            1135            1140

Gly Leu Ala Ser Pro Ala Arg Gly Ser Glu Arg Pro Arg Pro Arg
        1145            1150            1155

Thr His Arg Ala Leu Ala Leu Glu
        1160            1165

<210> SEQ ID NO 40
<211> LENGTH: 3167
<212> TYPE: PRT
<213> ORGANISM: Drosophila melanogaster

<400> SEQUENCE: 40

Met Glu Thr Val Ala Leu Gly Leu Pro Arg Leu Tyr Ser Ser Glu Arg
1               5                   10                  15

Gly Leu Tyr Thr His Arg Ala Leu Ala Ala Leu Ala Ser Glu Arg Ala
```

```
                20                  25                  30
Leu Ala Ala Leu Ala Ala Leu Ala Ala Leu Ala Leu Tyr Ser Ala Leu
            35                  40                  45
Ala Ser Glu Arg Ala Ser Asn Ala Ser Asn Ala Ser Asn Ala Ser Asn
50                  55                  60
Ala Ser Asn Ala Ser Asn His Ile Ser Pro Arg Ala Arg Gly Gly Leu
65                  70                  75                  80
Tyr Ser Glu Arg Gly Leu Tyr Ala Ser Pro Ser Glu Arg Gly Leu Tyr
                85                  90                  95
Ile Leu Glu Ala Arg Gly Ser Glu Arg Gly Leu Tyr Ser Glu Arg Gly
            100                 105                 110
Leu Tyr Ile Leu Glu Ser Glu Arg Cys Tyr Ser Ser Glu Arg Ala Ser
            115                 120                 125
Asn Thr His Arg Ala Ser Pro Ala Ser Asn Ser Glu Arg Cys Tyr Ser
            130                 135                 140
Ser Glu Arg Gly Leu Asn Ser Glu Arg Gly Leu Asn Ser Glu Arg Ala
145                 150                 155                 160
Ser Pro Gly Leu Tyr Gly Leu Asn Ala Ser Asn Gly Leu Leu Glu Thr
                165                 170                 175
His Arg Ala Arg Gly Thr Tyr Arg Ser Glu Arg Ser Glu Arg Gly Leu
            180                 185                 190
Ala Ser Pro Val Ala Leu Ser Glu Arg Gly Leu Tyr Ala Ser Asn Gly
            195                 200                 205
Leu Ser Glu Arg Ser Glu Arg Gly Leu Ala Leu Ala Pro Arg Ala Ser
            210                 215                 220
Asn Met Glu Thr Thr His Arg Gly Leu Val Ala Leu Gly Leu Ala Arg
225                 230                 235                 240
Gly Gly Leu Asn Ala Leu Ala Gly Leu Leu Glu Ala Ser Asn Ala Arg
                245                 250                 255
Gly His Ile Ser Leu Tyr Ser Gly Leu Gly Leu Met Glu Thr Gly Leu
                260                 265                 270
Asn Leu Tyr Ser Leu Tyr Ser Ala Arg Gly Ala Arg Gly Leu Tyr Ser
            275                 280                 285
Leu Tyr Ser Ala Arg Gly Ile Leu Glu Ser Glu Arg Ser Glu Arg Ser
            290                 295                 300
Glu Arg Leu Glu His Ile Ser Ser Glu Arg Ser Glu Arg Thr His Arg
305                 310                 315                 320
Pro His Glu Gly Leu Asn Gly Leu Leu Glu Thr Tyr Arg Leu Tyr Ser
                325                 330                 335
Leu Glu Thr His Arg Gly Leu Tyr Gly Leu Ile Leu Glu Leu Glu Gly
            340                 345                 350
Leu Tyr Gly Leu Gly Leu Tyr Ala Leu Ala Thr Tyr Arg Ala Leu Ala
            355                 360                 365
Ser Glu Arg Val Ala Leu Gly Leu Asn Thr His Arg Cys Tyr Ser Val
            370                 375                 380
Ala Leu Ala Ser Asn Ile Leu Glu Thr Tyr Arg Thr His Arg Ala Ser
385                 390                 395                 400
Pro Leu Glu Gly Leu Thr Tyr Arg Ala Leu Ala Val Ala Leu Leu Tyr
                405                 410                 415
Ser Val Ala Leu Ile Leu Glu Ala Ser Pro Leu Tyr Ser Ile Leu Glu
            420                 425                 430
Pro Arg Gly Leu Tyr His Ile Ser Ala Leu Ala Ala Arg Gly Ala Leu
            435                 440                 445
```

```
Ala Ala Arg Gly Val Ala Leu Pro His Glu Ala Arg Gly Gly Leu Val
    450                 455                 460

Ala Leu Gly Leu Thr His Arg Pro His Glu His Ile Ser His Ile Ser
465                 470                 475                 480

Cys Tyr Ser Gly Leu Asn Gly Leu Tyr His Ile Ser Leu Glu Gly Leu
                485                 490                 495

Tyr Ile Leu Glu Leu Glu Gly Leu Asn Leu Glu Ile Leu Glu Gly Leu
                500                 505                 510

Pro His Glu Pro His Glu Gly Leu Ala Ser Pro Ala Ser Pro Leu Tyr
            515                 520                 525

Ser Leu Tyr Ser Pro His Glu Thr Tyr Arg Leu Glu Val Ala Leu Pro
530                 535                 540

His Glu Gly Leu Leu Tyr Ser Ile Leu Glu Ala Ser Asn Gly Leu Tyr
545                 550                 555                 560

Gly Leu Tyr Pro Arg Leu Glu Leu Glu Ser Glu Arg Ala Arg Gly Ile
                565                 570                 575

Leu Glu Gly Leu Asn Gly Leu His Ile Ser Ile Leu Glu Cys Tyr Ser
                580                 585                 590

Pro His Glu Ser Glu Arg Gly Leu His Ile Ser Gly Leu Pro Arg Ser
            595                 600                 605

Glu Arg Gly Leu Asn Ile Leu Glu Ile Leu Glu Leu Tyr Ser Gly Leu
610                 615                 620

Ile Leu Glu Ala Leu Ala Ser Glu Arg Gly Leu Tyr Leu Glu Ala Ser
625                 630                 635                 640

Pro Pro His Glu Leu Glu His Ile Ser Leu Tyr Ser Leu Tyr Ser Gly
                645                 650                 655

Leu Tyr Ile Leu Glu Ala Leu Ala His Ile Ser Ala Arg Gly Ala Ser
                660                 665                 670

Pro Leu Glu Leu Tyr Ser Pro Arg Gly Leu Ala Ser Asn Ile Leu Glu
            675                 680                 685

Leu Glu Cys Tyr Ser Val Ala Leu Leu Tyr Ser Thr His Arg Ala Ser
            690                 695                 700

Pro Ser Glu Arg Leu Glu Cys Tyr Ser Pro Arg Ile Leu Glu Leu Tyr
705                 710                 715                 720

Ser Ile Leu Glu Cys Tyr Ser Ala Ser Pro His Glu Ala Ser Pro
                725                 730                 735

Leu Glu Gly Leu Tyr Ser Glu Arg Gly Leu Tyr Ile Leu Glu Leu Tyr
                740                 745                 750

Ser Pro His Glu Thr His Arg Thr His Arg Ala Ser Pro Ile Leu Glu
            755                 760                 765

Ser Glu Arg Ser Glu Arg Pro Arg Ala Leu Ala Ala Leu Ala Thr His
770                 775                 780

Arg Pro Arg Gly Leu Asn Leu Glu Leu Glu Thr His Arg Pro Arg Val
785                 790                 795                 800

Ala Leu Gly Leu Tyr Ser Glu Arg Ala Leu Ala Gly Leu Pro His Glu
                805                 810                 815

Met Glu Thr Ala Leu Ala Pro Arg Gly Leu Val Ala Leu Val Ala Leu
            820                 825                 830

Ala Ser Pro Leu Glu Pro His Glu Val Ala Leu Gly Leu Tyr Gly Leu
            835                 840                 845

Ala Leu Ala His Ile Ser Thr Tyr Arg Thr Tyr Arg Ala Ser Pro Leu
850                 855                 860
```

```
Tyr Ser Ala Arg Gly Cys Tyr Ser Ala Ser Pro Leu Glu Thr Arg Pro
865                 870                 875                 880

Ser Glu Arg Leu Glu Gly Leu Tyr Val Ala Leu Ile Leu Glu Ala Leu
            885                 890                 895

Ala Thr Tyr Arg Ile Leu Glu Leu Glu Leu Glu Cys Tyr Ser Gly Leu
            900                 905                 910

Tyr Thr Tyr Arg Pro Arg Pro Arg Pro His Glu Ser Glu Arg Gly Leu
            915                 920                 925

Tyr Ala Ser Asn Cys Tyr Ser Gly Leu Tyr Gly Leu Ala Ser Pro Cys
930                 935                 940

Tyr Ser Gly Tyr Thr Arg Pro Ala Ser Asn Ala Arg Gly Gly Leu Tyr
945                 950                 955                 960

Gly Leu Ala Ser Asn Cys Tyr Ser Ala Arg Gly Thr His Arg Cys Tyr
            965                 970                 975

Ser Gly Leu Asn Gly Leu Leu Glu Leu Glu Pro His Glu Gly Leu Ser
            980                 985                 990

Glu Arg Ile Leu Glu Gly Leu Asn Gly Leu Gly Leu Tyr His Ile Ser
            995                 1000                1005

Pro His Glu Ser Glu Arg Pro His Glu Pro Arg Gly Leu Ala Leu
    1010                1015                1020

Ala Gly Leu Thr Arg Pro His Ile Ser Ala Ser Pro Val Ala Leu
    1025                1030                1035

Ser Glu Arg Ala Ser Pro Gly Leu Ala Leu Ala Leu Tyr Ser Ala
    1040                1045                1050

Ser Pro Leu Glu Ile Leu Glu Ser Glu Arg Ala Ser Asn Leu Glu
    1055                1060                1065

Leu Glu Val Ala Leu Leu Tyr Ser Leu Tyr Ser Ala Leu Ala Ser
    1070                1075                1080

Glu Arg Ala Ser Asn Ala Arg Gly Leu Glu Ser Glu Arg Ala Leu
    1085                1090                1095

Ala Gly Leu Ala Leu Ala Val Ala Leu Leu Glu Ala Ser Asn His
    1100                1105                1110

Ile Ser Pro Arg Thr Arg Pro Ile Leu Glu Ala Arg Gly Met Glu
    1115                1120                1125

Thr Cys Tyr Ser Gly Leu Gly Leu Asn Gly Leu Pro Arg Pro Arg
    1130                1135                1140

Ala Leu Ala Ser Glu Arg Leu Tyr Ser His Ile Ser Gly Leu Tyr
    1145                1150                1155

Ala Arg Gly Ala Arg Gly His Ile Ser Leu Tyr Ser Ala Leu Ala
    1160                1165                1170

Leu Glu Gly Leu Asn Thr His Arg Pro Arg Ser Glu Arg Ala Ser
    1175                1180                1185

Asn Ile Leu Glu Ala Arg Gly Ala Arg Gly Ala Ser Asn His Ile
    1190                1195                1200

Ser Gly Leu Asn Ser Glu Arg Ala Leu Ala Ala Arg Gly Gly Leu
    1205                1210                1215

Ile Leu Glu Ser Glu Arg Gly Leu Asn Pro His Glu Ala Leu Ala
    1220                1225                1230

Gly Leu Ser Glu Arg Ala Leu Ala Met Glu Thr Ala Leu Ala Val
    1235                1240                1245

Ala Leu Leu Tyr Ser Ala Arg Gly Val Ala Leu Val Ala Leu Leu
    1250                1255                1260

Glu Gly Leu Asn His Ile Ser Pro His Glu Ser Glu Arg Met Glu
```

-continued

```
            1265                1270                1275
Thr Ala Arg Gly Thr Tyr Arg Ala Ser Pro Thr Tyr Arg Met Glu
            1280                1285                1290
Thr Leu Tyr Ser Gly Leu Ala Arg Gly Pro Arg Ala Ser Asn Ile
            1295                1300                1305
Leu Glu Thr Tyr Arg Gly Leu Asn Pro Arg Ser Glu Arg Gly Leu
            1310                1315                1320
Asn Ala Leu Ala Thr Tyr Arg Met Glu Thr Ala Ser Pro Ala Leu
            1325                1330                1335
Ala Thr Tyr Arg Ser Glu Arg Ala Ser Pro Gly Leu Ala Ser Asn
            1340                1345                1350
Thr Tyr Arg Ala Ser Asn Pro Arg Leu Tyr Ser Pro Arg Pro Arg
            1355                1360                1365
Gly Leu Tyr His Ile Ser Thr Tyr Arg Thr His Arg Ala Arg Gly
            1370                1375                1380
Ala Ser Asn Ala Arg Gly Ser Glu Arg Gly Leu Asn Ala Arg Gly
            1385                1390                1395
Ala Ser Asn Pro Arg Ala Leu Ala Ser Glu Arg Ser Glu Arg Leu
            1400                1405                1410
Glu Cys Tyr Ser Gly Leu Tyr Thr Tyr Arg Gly Leu Tyr Gly Leu
            1415                1420                1425
Tyr Ala Arg Gly Met Glu Thr Ser Glu Arg Ser Glu Arg Met Glu
            1430                1435                1440
Thr His Ile Ser Gly Leu Tyr Gly Leu Asn Ala Arg Gly Ala Leu
            1445                1450                1455
Ala Ala Ser Asn Ser Glu Arg Ala Arg Gly Ala Arg Gly Ser Glu
            1460                1465                1470
Arg Ser Glu Arg Ala Arg Gly Ala Ser Asn Ala Leu Ala Ser Glu
            1475                1480                1485
Arg Ala Arg Gly Ala Ser Asn Ala Leu Ala Ser Glu Arg Ala Leu
            1490                1495                1500
Ala Ile Leu Glu Thr Tyr Arg Pro Arg Ala Ser Asn Ser Glu Arg
            1505                1510                1515
Gly Leu Tyr Gly Leu Tyr Pro His Glu Leu Tyr Ser Thr His Arg
            1520                1525                1530
Leu Glu Ala Ser Asn Val Ala Leu His Ile Ser Gly Leu Gly Leu
            1535                1540                1545
Ala Ser Pro Ala Ser Pro Ala Ser Pro Ala Ser Pro Gly Leu Gly
            1550                1555                1560
Leu Tyr Leu Glu Gly Leu Ala Leu Ala Pro His Glu Gly Leu Tyr
            1565                1570                1575
His Ile Ser Ile Leu Glu Ala Ser Pro Ala Ser Pro Ala Ser Pro
            1580                1585                1590
Ala Ser Pro Gly Leu Thr Arg Pro Ser Glu Arg Ala Arg Gly Ser
            1595                1600                1605
Glu Arg Ala Arg Gly Ala Arg Gly Gly Leu Thr Tyr Arg Gly Leu
            1610                1615                1620
Asn Gly Leu Asn Gly Leu Asn Cys Tyr Ser Gly Leu Thr His Arg
            1625                1630                1635
Leu Glu Gly Leu Tyr Gly Leu Ala Ser Pro Ala Arg Gly Pro His
            1640                1645                1650
Glu Ala Arg Gly Ala Arg Gly Gly Leu Asn Ser Glu Arg Gly Leu
            1655                1660                1665
```

```
Tyr Ser Glu Arg Gly Leu Gly Leu Tyr Ala Ser Pro Gly Leu Val
    1670            1675                1680

Ala Leu Gly Leu Ala Ser Pro Ala Ser Pro Gly Leu Ala Ser Pro
    1685            1690                1695

Gly Leu Tyr Gly Leu Ala Ser Asn Gly Leu Ala Ser Pro Thr Tyr
    1700            1705                1710

Arg Gly Leu Asn His Ile Ser Thr Tyr Arg Leu Tyr Ser His Ile
    1715            1720                1725

Ser Thr Tyr Arg Thr Arg Pro Ala Arg Gly Gly Leu Leu Glu Ala
    1730            1735                1740

Ser Pro Gly Leu Gly Leu Gly Leu Gly Leu Tyr Ala Ser Pro Ala
    1745            1750                1755

Ser Pro Thr Tyr Arg Leu Glu Thr Tyr Arg Gly Leu Gly Leu Asn
    1760            1765                1770

Gly Leu Asn Gly Leu Asn Ala Arg Gly Val Ala Leu Ala Ser Pro
    1775            1780                1785

Ala Ser Pro Leu Tyr Ser Pro His Glu Gly Leu Tyr Gly Leu Gly
    1790            1795                1800

Leu Gly Leu Pro His Glu Gly Leu Ala Ser Pro Gly Leu Pro Arg
    1805            1810                1815

Leu Tyr Ser Gly Leu Gly Leu Thr His Arg Gly Leu Asn Ala Leu
    1820            1825                1830

Ala Ala Ser Pro Ala Ser Asn Leu Glu Leu Tyr Ser Leu Glu Ser
    1835            1840                1845

Glu Arg Leu Tyr Ser Ala Leu Ala Thr Tyr Arg Val Ala Leu Gly
    1850            1855                1860

Leu Gly Leu Asn Val Ala Leu Gly Leu Tyr Gly Leu Thr His Arg
    1865            1870                1875

Ala Ser Asn Val Ala Leu Gly Leu Leu Tyr Ser Ser Glu Arg Leu
    1880            1885                1890

Tyr Ser Pro Arg Gly Leu Asn Ala Ser Pro Ala Ser Pro Ala Ser
    1895            1900                1905

Asn Gly Leu Tyr Gly Leu Tyr Thr Tyr Arg Ile Leu Glu Ala Arg
    1910            1915                1920

Gly Gly Leu Ala Ser Pro Leu Glu Ile Leu Glu Met Glu Thr Ala
    1925            1930                1935

Ser Pro Ala Ser Asn Met Glu Thr Ala Ser Pro Met Glu Thr Leu
    1940            1945                1950

Tyr Ser Leu Tyr Ser Ala Ser Asn Thr His Arg Gly Leu Asn Gly
    1955            1960                1965

Leu Asn Ser Glu Arg Gly Leu Pro His Glu Ala Leu Ala Leu Tyr
    1970            1975                1980

Ser Leu Glu Thr His Arg Ile Leu Glu Met Glu Thr Ala Arg Gly
    1985            1990                1995

Ala Ser Asn Ala Ser Pro Ala Leu Ala Gly Leu Asn Thr His Arg
    2000            2005                2010

Gly Leu Gly Leu Ala Ser Asn Leu Tyr Ser Ile Leu Glu Met Glu
    2015            2020                2025

Thr Gly Leu Asn Gly Leu Asn Gly Leu Asn Ala Ser Pro Gly Leu
    2030            2035                2040

Gly Leu Leu Tyr Ser Leu Tyr Ser Gly Leu Ala Ser Pro Leu Tyr
    2045            2050                2055
```

-continued

Ser Gly Leu Asn Gly Leu Asn Ala Ser Pro Ala Ser Pro Val Ala
    2060                2065            2070

Leu Ala Ser Pro Gly Leu Tyr Ala Leu Ala Leu Tyr Ser Leu Tyr
    2075                2080            2085

Ser Gly Leu Asn Gly Leu Tyr Pro Arg Ser Glu Arg Ser Glu Arg
    2090                2095            2100

Ala Ser Pro Ile Leu Glu Ser Glu Arg Ala Leu Ala Thr His Arg
    2105                2110            2115

Thr His Arg Ile Leu Glu Thr His Arg Ala Ser Pro Ala Ser Asn
    2120                2125            2130

Ala Ser Asn Leu Tyr Ser Leu Glu Gly Leu Asn Thr His Arg Pro
    2135                2140            2145

Arg Val Ala Leu Met Glu Thr Thr His Arg Thr His Arg Thr His
    2150                2155            2160

Arg His Ile Ser Ile Leu Glu Ala Ser Asn Ala Ser Asn Thr Arg
    2165                2170            2175

Pro Gly Leu Asn Thr His Arg Gly Leu Tyr Ala Ser Pro Ala Leu
    2180                2185            2190

Ala Ile Leu Glu Gly Leu Ala Ser Pro Ala Ser Pro Ala Ser Pro
    2195                2200            2205

Val Ala Leu Leu Tyr Ser Leu Glu Leu Glu Ala Ser Pro Ser Glu
    2210                2215            2220

Arg Ile Leu Glu Ser Glu Arg Ala Ser Pro Leu Glu Ala Ser Asn
    2225                2230            2235

Gly Leu Leu Tyr Ser Leu Glu Pro Arg Gly Leu Ile Leu Glu Thr
    2240                2245            2250

Tyr Arg Gly Leu Thr His Arg Ala Leu Ala Ala Ser Asn Ile Leu
    2255                2260            2265

Glu Val Ala Leu Val Ala Leu Ala Ser Asn Ser Glu Arg Ala Leu
    2270                2275            2280

Ala Ala Leu Ala Val Ala Leu Pro Arg Ala Leu Ala Ala Leu Ala
    2285                2290            2295

Ser Glu Arg Thr His Arg Pro Arg Ala Leu Ala Ala Leu Ala Ser
    2300                2305            2310

Glu Arg Ala Leu Ala Thr His Arg Ala Arg Gly Pro Arg Pro Arg
    2315                2320            2325

Thr His Arg Ala Ser Pro Ala Ser Asn Pro Arg Gly Leu Gly Leu
    2330                2335            2340

Ala Ser Pro Ala Ser Pro Ser Glu Arg Ala Ser Asn Val Ala Leu
    2345                2350            2355

Thr His Arg Leu Tyr Ser Pro Arg Thr His Arg Thr His Arg Thr
    2360                2365            2370

His Arg Ala Leu Ala Gly Leu Gly Leu Tyr Thr His Arg Thr His
    2375                2380            2385

Arg Met Glu Thr Gly Leu Asn Thr His Arg Thr His Arg Pro His
    2390                2395            2400

Glu Gly Leu Tyr Met Glu Thr Ser Glu Arg Ala Leu Ala Gly Leu
    2405                2410            2415

Gly Leu Gly Leu Leu Tyr Ser Pro Arg Val Ala Leu Ala Leu Ala
    2420                2425            2430

Leu Glu Ser Glu Arg His Ile Ser Thr His Arg Ala Leu Ala Gly
    2435                2440            2445

Leu Tyr His Ile Ser His Ile Ser Ser Glu Arg Leu Tyr Ser Thr

```
                    2450                    2455                    2460
His Arg Gly Leu Tyr Ala Arg Gly Thr His Arg Val Ala Leu Ala
    2465                    2470                    2475
Ser Asn Pro His Glu Ala Leu Ala Pro Arg Ala Ser Pro Ala Leu
    2480                    2485                    2490
Ala Thr Tyr Arg Gly Leu Asn Ala Ser Asn Ala Ser Pro Gly Leu
    2495                    2500                    2505
Ala Ser Pro Ala Leu Ala Ala Ser Pro Ile Leu Glu Ala Ser Pro
    2510                    2515                    2520
Gly Leu Ala Ser Pro Ala Ser Pro Ala Ser Pro Thr Tyr Arg Ala
    2525                    2530                    2535
Ser Pro Ala Ser Pro Gly Leu Gly Leu Ala Ser Asn Leu Glu His
    2540                    2545                    2550
Ile Ser Gly Leu His Ile Ser Ser Glu Arg Leu Tyr Ser Gly Leu
    2555                    2560                    2565
Asn Gly Leu Asn Leu Glu Pro Arg Ser Glu Arg Ala Ser Asn Ala
    2570                    2575                    2580
Leu Ala Thr Tyr Arg Thr His Arg Ala Arg Gly Leu Tyr Ser Gly
    2585                    2590                    2595
Leu Asn Ala Arg Gly Gly Leu Asn Gly Leu Asn His Ile Ser Gly
    2600                    2605                    2610
Leu Asn Ala Arg Gly Thr Tyr Arg Ile Leu Glu Val Ala Leu Pro
    2615                    2620                    2625
Arg Ala Arg Gly Thr Tyr Arg Gly Leu Asn Leu Glu Ala Leu Ala
    2630                    2635                    2640
Ala Ser Pro Gly Leu Asn Val Ala Leu Pro Arg Gly Leu Asn Ala
    2645                    2650                    2655
Arg Gly Gly Leu Asn His Ile Ser Thr His Arg Gly Leu Ala Ser
    2660                    2665                    2670
Asn Thr Arg Pro Ala Arg Gly Thr Tyr Arg Ala Arg Gly Thr His
    2675                    2680                    2685
Arg His Ile Ser His Ile Ser Ser Glu Arg Gly Leu Asn Gly Leu
    2690                    2695                    2700
Gly Leu Asn Gly Leu Asn Pro Arg Thr His Arg Ala Leu Ala Ala
    2705                    2710                    2715
Ser Pro Thr Tyr Arg Ala Arg Gly Leu Tyr Ser Thr Tyr Arg Ala
    2720                    2725                    2730
Arg Gly Pro Arg Pro Arg Pro His Glu Ser Glu Arg Thr His Arg
    2735                    2740                    2745
Gly Leu Tyr Gly Leu Tyr Gly Leu Tyr Gly Leu Tyr Gly Leu Tyr
    2750                    2755                    2760
His Ile Ser His Ile Ser Gly Leu Tyr Ala Ser Asn Leu Glu Gly
    2765                    2770                    2775
Leu Asn Ala Arg Gly Ala Ser Asn Thr Tyr Arg Leu Glu Gly Leu
    2780                    2785                    2790
Tyr Ser Glu Arg Pro His Glu Ser Glu Arg His Ile Ser Ser Glu
    2795                    2800                    2805
Arg Gly Leu Tyr Gly Leu Tyr Ala Leu Ala Ala Leu Ala Gly Leu
    2810                    2815                    2820
Tyr Thr Tyr Arg Leu Tyr Ser Ile Leu Glu Ala Ser Asn Ser Glu
    2825                    2830                    2835
Arg Pro Arg Pro Arg Cys Tyr Ser Val Ala Leu Gly Leu Asn Ala
    2840                    2845                    2850
```

-continued

Arg Gly Ala Arg Gly Ile Leu Glu Met Glu Thr Ala Ser Pro Ala
            2855                2860                2865

Leu Ala Pro Arg Met Glu Thr Pro Arg Pro Arg Ala Leu Ala Gly
    2870                2875                2880

Leu Tyr Ser Glu Arg Ser Glu Arg Gly Leu Tyr Ser Glu Arg Ala
    2885                2890                2895

Ser Pro Gly Leu Gly Leu Asn Ser Glu Arg Thr Tyr Arg Ala Leu
    2900                2905                2910

Ala Ala Arg Gly Ser Glu Arg Cys Tyr Ser His Ile Ser Ala Ser
    2915                2920                2925

Asn Ala Arg Gly Ser Glu Arg Ser Glu Arg Gly Leu Tyr Ser Glu
    2930                2935                2940

Arg Gly Leu Tyr Ala Arg Gly Pro His Glu Gly Leu Leu Glu Pro
    2945                2950                2955

Arg Ala Ser Pro Met Glu Thr Pro Arg Met Glu Thr Gly Leu Asn
    2960                2965                2970

Pro Arg Pro Arg Ser Glu Arg Gly Leu Tyr Ser Glu Arg Gly Leu
    2975                2980                2985

Tyr Ser Glu Arg Ala Leu Ala Ile Glu Ala Arg Gly Ala Ser Asn
    2990                2995                3000

Thr Arg Pro Gly Leu Tyr Met Glu Thr Ala Ser Asn Gly Leu Asn
    3005                3010                3015

Gly Leu Tyr Gly Leu Tyr Gly Leu Asn Ala Arg Gly Val Ala Leu
    3020                3025                3030

Gly Leu Asn Ala Leu Ala His Ile Ser Leu Glu Gly Leu Asn Ala
    3035                3040                3045

Leu Ala Ala Arg Gly Ile Glu Gly Leu Tyr Leu Glu Ser Glu Arg
    3050                3055                3060

Pro Arg Ala Arg Gly His Ile Ser Gly Leu Tyr Gly Leu Tyr Ser
    3065                3070                3075

Glu Arg Ala Arg Gly Leu Asn Ala Ser Pro Pro Arg Gly Leu
    3080                3085                3090

Gly Leu Asn Gly Leu Asn Gly Leu Asn Pro Arg Ala Leu Ala Gly
    3095                3100                3105

Asn Leu Glu Pro Arg Pro Arg Ser Glu Arg Gly Leu Ser Glu Arg
    3110                3115                3120

Val Ala Leu Leu Glu Leu Glu Gly Leu Asn Ala Ser Asn Ala Ser
    3125                3130                3135

Pro Leu Glu Ser Glu Arg Gly Leu Val Ala Leu Ala Arg Gly Gly
    3140                3145                3150

Leu Tyr Ser Glu Arg Thr His Arg Val Ala Leu Ala Ser Pro
    3155                3160                3165

<210> SEQ ID NO 41
<211> LENGTH: 1199
<212> TYPE: PRT
<213> ORGANISM: Homo sapiens

<400> SEQUENCE: 41

Ala Arg Gly Ala Arg Gly Leu Glu Ala Arg Gly Gly Leu Asn Gly Leu
1               5                   10                  15

Asn Gly Leu Asn Ala Arg Gly Ala Leu Ala Leu Glu Ala Arg Gly Ala
            20                  25                  30

Leu Ala Gly Leu Tyr His Ile Ser Ala Arg Gly Gly Leu Asn Thr Arg

```
                35                  40                  45
Pro Leu Glu Ala Arg Gly Met Glu Thr Val Ala Leu Gly Leu Asn Leu
 50                  55                  60

Tyr Ser Leu Tyr Ser Pro Arg Ala Leu Ala Gly Leu Leu Glu Gly Leu
 65                  70                  75                  80

Asn Gly Leu Tyr Pro His Glu His Ile Ser Ala Arg Gly Ser Glu Arg
                 85                  90                  95

Pro His Glu Leu Tyr Ser Gly Leu Tyr Gly Leu Asn Ala Ser Asn Pro
                100                 105                 110

Arg Pro His Glu Gly Leu Leu Glu Ala Leu Ala Pro His Glu Ser Glu
            115                 120                 125

Arg Leu Glu Ala Ser Pro Gly Leu Asn Pro Arg Ala Ser Pro His Ile
            130                 135                 140

Ser Gly Leu Tyr Ala Ser Pro Ser Glu Arg Ala Ser Pro His Glu
145                 150                 155                 160

Gly Leu Tyr Leu Glu Gly Leu Asn Cys Tyr Ser Ser Glu Arg Ala Leu
                165                 170                 175

Ala Ala Arg Gly Pro Arg Ala Ser Pro Met Glu Thr Pro Arg Ala Leu
            180                 185                 190

Ala Ser Glu Arg Gly Leu Asn Pro Arg Ile Leu Glu Ala Ser Pro Ile
            195                 200                 205

Leu Glu Pro Arg Ala Ser Pro Ala Leu Ala Leu Tyr Ser Leu Tyr Ser
210                 215                 220

Ala Arg Gly Gly Leu Tyr Leu Tyr Ser Leu Tyr Ser Leu Tyr Ser Leu
225                 230                 235                 240

Tyr Ser Ala Arg Gly Gly Leu Tyr Ala Arg Gly Ala Leu Ala Thr His
                245                 250                 255

Arg Ala Ser Pro Ser Glu Arg Pro His Glu Ser Glu Arg Gly Leu Tyr
            260                 265                 270

Ala Arg Gly Pro His Glu Gly Leu Ala Ser Pro Val Ala Leu Thr Tyr
            275                 280                 285

Arg Gly Leu Asn Leu Glu Gly Leu Asn Gly Leu Ala Ser Pro Val Ala
290                 295                 300

Leu Leu Glu Gly Leu Tyr Gly Leu Gly Leu Tyr Ala Leu Ala His Ile
305                 310                 315                 320

Ser Ala Leu Ala Ala Arg Gly Val Ala Leu Gly Leu Asn Thr His Arg
                325                 330                 335

Cys Tyr Ser Ile Leu Glu Ala Ser Asn Leu Glu Ile Leu Glu Thr His
                340                 345                 350

Arg Ser Glu Arg Gly Leu Asn Gly Leu Thr Tyr Arg Ala Leu Ala Val
            355                 360                 365

Ala Leu Leu Tyr Ser Ile Leu Glu Ile Leu Glu Gly Leu Tyr Ser Gly
            370                 375                 380

Leu Asn Pro Arg Gly Leu Tyr His Ile Ser Ile Leu Glu Ala Arg Gly
385                 390                 395                 400

Ser Glu Arg Ala Arg Gly Val Ala Leu Pro His Glu Ala Arg Gly Gly
                405                 410                 415

Leu Val Ala Leu Gly Leu Met Glu Thr Leu Glu Thr Tyr Arg Gly Leu
            420                 425                 430

Asn Cys Tyr Ser Gly Leu Asn Gly Leu Tyr His Ile Ser Ala Arg Gly
            435                 440                 445

Ala Ser Asn Val Ala Leu Leu Glu Gly Leu Leu Glu Ile Leu Glu Gly
450                 455                 460
```

```
Leu Pro His Glu Pro His Glu Gly Leu Gly Leu Gly Leu Ala Ser Pro
465                 470                 475                 480

Ala Arg Gly Pro His Glu Thr Tyr Arg Leu Glu Val Ala Leu Pro His
                485                 490                 495

Glu Gly Leu Leu Tyr Ser Met Glu Thr Ala Arg Gly Gly Leu Tyr Gly
            500                 505                 510

Leu Tyr Ser Glu Arg Ile Leu Glu Leu Glu Ser Glu Arg His Ile Ser
            515                 520                 525

Ile Leu Glu His Ile Ser Leu Tyr Ser Ala Arg Gly Ala Arg Gly His
530                 535                 540

Ile Ser Pro His Glu Ala Ser Asn Gly Leu Leu Glu Gly Leu Ala Leu
545                 550                 555                 560

Ala Ser Glu Arg Val Ala Leu Val Ala Leu Val Ala Leu Gly Leu Asn
                565                 570                 575

Ala Ser Pro Val Ala Leu Ala Leu Ala Ser Glu Arg Ala Leu Ala Leu
            580                 585                 590

Glu Ala Ser Pro Pro His Glu Leu Glu His Ile Ser Ala Ser Asn Leu
            595                 600                 605

Tyr Ser Gly Leu Tyr Ile Leu Glu Ala Leu Ala His Ile Ser Ala Arg
610                 615                 620

Gly Ala Ser Pro Leu Glu Leu Tyr Ser Pro Arg Gly Leu Ala Ser Asn
625                 630                 635                 640

Ile Leu Glu Leu Glu Cys Tyr Ser Gly Leu His Ile Ser Pro Arg Ala
                645                 650                 655

Ser Asn Gly Leu Asn Val Ala Leu Ser Glu Arg Pro Arg Val Ala Leu
            660                 665                 670

Leu Tyr Ser Ile Leu Glu Cys Tyr Ser Ala Ser Pro Pro His Glu Ala
            675                 680                 685

Ser Pro Leu Glu Gly Leu Tyr Ser Glu Arg Gly Leu Tyr Ile Leu Glu
            690                 695                 700

Leu Tyr Ser Leu Glu Ala Ser Asn Gly Leu Tyr Ala Ser Pro Cys Tyr
705                 710                 715                 720

Ser Ser Glu Arg Pro Arg Ile Leu Glu Ser Arg Thr His Arg Pro
                725                 730                 735

Arg Gly Leu Leu Glu Leu Glu Thr His Arg Pro Arg Cys Tyr Ser Gly
                740                 745                 750

Leu Tyr Ser Glu Arg Ala Leu Ala Gly Leu Thr Tyr Arg Met Glu Thr
            755                 760                 765

Ala Leu Ala Pro Arg Gly Leu Leu Glu Val Ala Leu Gly Leu Ala Leu
            770                 775                 780

Ala Pro His Glu Ser Glu Arg Gly Leu Gly Leu Ala Leu Ala Ser Glu
785                 790                 795                 800

Arg Ile Leu Glu Thr Tyr Arg Ala Ser Pro Leu Tyr Ser Ala Arg Gly
                805                 810                 815

Cys Tyr Ser Ala Ser Pro Leu Glu Thr Arg Pro Ser Glu Arg Leu Glu
            820                 825                 830

Gly Leu Tyr Val Ala Leu Ile Leu Glu Leu Glu Thr Tyr Arg Ile Leu
            835                 840                 845

Glu Leu Glu Leu Glu Ser Glu Arg Gly Leu Tyr Thr Tyr Arg Pro Arg
            850                 855                 860

Pro Arg Pro His Glu Val Ala Leu Gly Leu Tyr Ala Arg Gly Cys Tyr
865                 870                 875                 880
```

Ser Gly Leu Tyr Ser Glu Arg Ala Ser Pro Cys Tyr Ser Gly Leu Tyr
            885                 890                 895

Thr Arg Pro Ala Ser Pro Ala Arg Gly Gly Leu Tyr Gly Leu Ala Leu
        900                 905                 910

Ala Cys Tyr Ser Pro Arg Ala Leu Ala Cys Tyr Ser Gly Leu Asn Ala
        915                 920                 925

Ser Asn Met Glu Thr Leu Glu Pro His Glu Gly Leu Ser Glu Arg Ile
930                 935                 940

Leu Glu Gly Leu Asn Gly Leu Gly Leu Tyr Leu Tyr Ser Thr Tyr Arg
945                 950                 955                 960

Gly Leu Pro His Glu Pro Arg Ala Ser Pro Leu Tyr Ser Ala Ser Pro
            965                 970                 975

Thr Arg Pro Ala Leu Ala His Ile Ser Ile Leu Glu Ser Glu Arg Cys
        980                 985                 990

Tyr Ser Ala Leu Ala Ala Leu Ala Leu Tyr Ser Ala Ser Pro Leu Glu
        995                 1000                1005

Ile Leu Glu Ser Glu Arg Leu Tyr Ser Leu Glu Leu Glu Val Ala
    1010                1015                1020

Leu Ala Arg Gly Ala Ser Pro Ala Leu Ala Leu Tyr Ser Gly Leu
    1025                1030                1035

Asn Ala Arg Gly Leu Glu Ser Glu Arg Ala Leu Ala Ala Leu Ala
    1040                1045                1050

Gly Leu Asn Val Ala Leu Leu Glu Gly Leu Asn His Ile Ser Pro
    1055                1060                1065

Arg Thr Arg Pro Val Ala Leu Gly Leu Asn Gly Leu Tyr Cys Tyr
    1070                1075                1080

Ser Ala Leu Ala Pro Arg Gly Leu Ala Ser Asn Thr His Arg Leu
    1085                1090                1095

Glu Pro Arg Thr His Arg Pro Arg Met Glu Thr Val Ala Leu Leu
    1100                1105                1110

Glu Gly Leu Asn Ala Arg Gly Thr Arg Pro Ala Ser Pro Ser Glu
    1115                1120                1125

Arg His Ile Ser Pro His Glu Leu Glu Leu Glu Pro Arg Pro Arg
    1130                1135                1140

His Ile Ser Pro Arg Cys Tyr Ser Ala Arg Gly Ile Leu Glu His
    1145                1150                1155

Ile Ser Val Ala Leu Ala Arg Gly Pro Arg Gly Leu Tyr Gly Leu
    1160                1165                1170

Tyr Leu Glu Val Ala Leu Ala Arg Gly Thr His Arg Val Ala Leu
    1175                1180                1185

Thr His Arg Val Ala Leu Ala Ser Asn Gly Leu
    1190                1195

<210> SEQ ID NO 42
<211> LENGTH: 48
<212> TYPE: DNA
<213> ORGANISM: Mus musculus

<400> SEQUENCE: 42
ccttagacct cggcccagca cagggaagcc cgacctggtg agccccca           48

<210> SEQ ID NO 43
<211> LENGTH: 48
<212> TYPE: DNA
<213> ORGANISM: Mus musculus

```
<400> SEQUENCE: 43
ctcttctcta cagacatgcc ttccgcaggt tcgaaggtga gctgcaga                    48

<210> SEQ ID NO 44
<211> LENGTH: 48
<212> TYPE: DNA
<213> ORGANISM: Mus musculus

<400> SEQUENCE: 44
ctcgcattcc agatgtctat cagctatgct gtcaagagct ggggtctg                    48

<210> SEQ ID NO 45
<211> LENGTH: 48
<212> TYPE: DNA
<213> ORGANISM: Mus musculus

<400> SEQUENCE: 45
cctacattgt agatcattga gaagcaggga cataggtaag gtggcctg                    48

<210> SEQ ID NO 46
<211> LENGTH: 49
<212> TYPE: DNA
<213> ORGANISM: Mus musculus

<400> SEQUENCE: 46
tcccaactca ggaatgttct agaagaagat gcgtggcggt aggtactgg                   49

<210> SEQ ID NO 47
<211> LENGTH: 48
<212> TYPE: DNA
<213> ORGANISM: Nus musculus

<400> SEQUENCE: 47
ctggcctgca caggatccat cctagcataa caaaggtgtg gcagggac                    48

<210> SEQ ID NO 48
<211> LENGTH: 48
<212> TYPE: DNA
<213> ORGANISM: Mus musculus

<400> SEQUENCE: 48
cacctcacta ggcatcgccc acagccccaa ccaggtgagg ctgcctga                    48

<210> SEQ ID NO 49
<211> LENGTH: 48
<212> TYPE: DNA
<213> ORGANISM: Mus musculus

<400> SEQUENCE: 49
ccattcccag gtctcgccag tgaagctgct caccccggtg agggcagt                    48

<210> SEQ ID NO 50
<211> LENGTH: 48
<212> TYPE: DNA
<213> ORGANISM: Mus musculus

<400> SEQUENCE: 50
ccctgcccca cagtgtgggt cagctgggtg caggggtaa gccttggg                     48

<210> SEQ ID NO 51
<211> LENGTH: 48
<212> TYPE: DNA
<213> ORGANISM: Mus musculus
```

```
<400> SEQUENCE: 51
gacttcttac agtgtgcccc agagttggtt ctgcagaggt gaggcctg                    48

<210> SEQ ID NO 52
<211> LENGTH: 48
<212> TYPE: DNA
<213> ORGANISM: Mus musculus

<400> SEQUENCE: 52
catcctatcc ccaggaacag ctgtgtcatt taaaaatttc tgtgcagt                    48

<210> SEQ ID NO 53
<211> LENGTH: 34
<212> TYPE: DNA
<213> ORGANISM: Mus musculus

<400> SEQUENCE: 53
aaacacaagc ctaaaaaaaa aaacaagcat gggg                                   34
```